US012590718B2

(12) United States Patent
Serenari et al.

(10) Patent No.: US 12,590,718 B2
(45) Date of Patent: Mar. 31, 2026

(54) AIR CONDITIONING SYSTEMS FOR ROOMS

(71) Applicant: STE Srl, San Lazzaro di Savena (IT)

(72) Inventors: Stefano Serenari, San Lazzaro di Savena (IT); Federico Serenari, San Lazzaro di Savena (IT)

( * ) Notice: Subject to any disclaimer, the term of this patent is extended or adjusted under 35 U.S.C. 154(b) by 351 days.

(21) Appl. No.: 18/555,759

(22) PCT Filed: Apr. 21, 2022

(86) PCT No.: PCT/IB2022/053731
§ 371 (c)(1),
(2) Date: Oct. 17, 2023

(87) PCT Pub. No.: WO2022/224185
PCT Pub. Date: Oct. 27, 2022

(65) Prior Publication Data
US 2024/0210048 A1 Jun. 27, 2024

(30) Foreign Application Priority Data
Apr. 21, 2021 (IT) ......................... 102021000010184

(51) Int. Cl.
*F24F 3/16* (2021.01)
*A61L 9/20* (2006.01)
(Continued)

(52) U.S. Cl.
CPC ................ *F24F 3/16* (2013.01); *A61L 9/205* (2013.01); *F24F 8/22* (2021.01); *F24F 11/74* (2018.01);
(Continued)

(58) Field of Classification Search
CPC .. F24F 13/16; F24F 13/10; F24F 13/08; F24F 13/14; F24F 13/06; F24F 13/24;
(Continued)

(56) References Cited

U.S. PATENT DOCUMENTS 3,200,734 A 8/1965 Burns et al.
2006/0211362 A1* 9/2006 Levy ....................... F24F 7/007
454/186

(Continued)

FOREIGN PATENT DOCUMENTS

CN 204535005 8/2015
CN 105910216 8/2016
(Continued)

*Primary Examiner* — William C Doerrler
(74) *Attorney, Agent, or Firm* — Themis Law

(57) ABSTRACT

An air conditioning system serving a room to be treated using a source of conditioned air includes one or more multifunction apparatuses, which are equipped with a plenum, one or more air supply ducts to feed the plenum through one or more inlet openings, and a terminal element for interfacing the one or more multifunction apparatuses to enable the passage of the conditioned air and exchange heat by irradiation and/or convection with the room to be treated. The multifunction apparatuses are arranged into the room to be treated with a vertical or horizontal extension and include regulation systems for varying the distribution of conditioned air in the one or more multifunction apparatuses between the vertical and/or horizontal internal portions of the apparatuses.

25 Claims, 45 Drawing Sheets

(51) Int. Cl.

| | | |
|---|---|---|
| *F24F 8/22* | (2021.01) | |
| *F24F 11/74* | (2018.01) | |
| *F24F 13/10* | (2006.01) | |
| *F24F 13/24* | (2006.01) | |

(52) U.S. Cl.
CPC .............. *F24F 13/10* (2013.01); *F24F 13/24* (2013.01); *A61L 2209/16* (2013.01); *F24F 2013/245* (2013.01); *F24F 2221/02* (2013.01)

(58) Field of Classification Search
CPC .......... F24F 8/22; F24F 5/0017; F24F 5/0089; F24F 3/056; F24F 3/16; F24F 11/74; F24F 2221/02; F24F 2221/54; F24F 2013/245; F24F 2003/0446; A61L 9/205; A61L 2209/16
See application file for complete search history.

(56) References Cited

U.S. PATENT DOCUMENTS

| | | | | |
|---|---|---|---|---|
| 2019/0145642 A1 * | 5/2019 | Heigl | ...................... | F24F 13/10 454/239 |
| 2020/0003450 A1 | 1/2020 | Surminski et al. | | |

FOREIGN PATENT DOCUMENTS

| | | | | |
|---|---|---|---|---|
| EP | 0106449 | 4/1984 | | |
| EP | 0106449 A1 * | 4/1984 | ............ | F24F 13/072 |
| EP | 2354687 | 8/2011 | | |
| EP | 3499139 A1 * | 6/2019 | .......... | F24F 13/0227 |
| GB | 2099034 | 12/1982 | | |
| JP | H0359343 | 3/1991 | | |
| WO | WO-2006051609 A1 * | 5/2006 | ................ | F24F 7/10 |

* cited by examiner

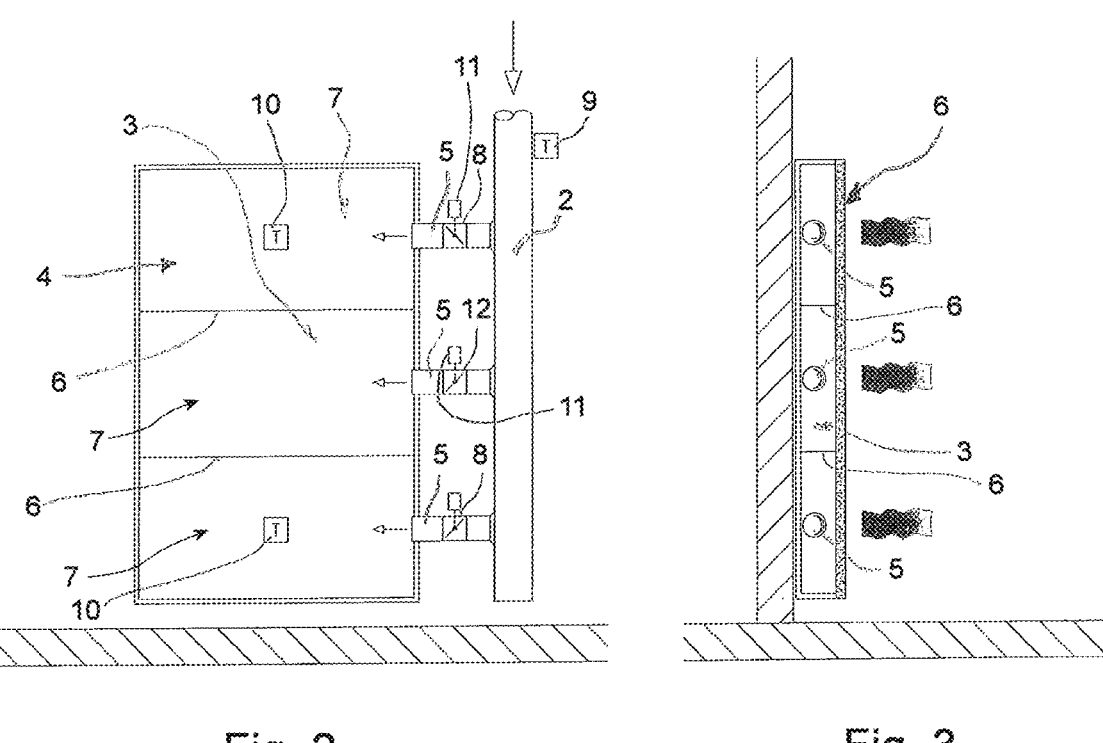
Fig, 2
Fig. 3
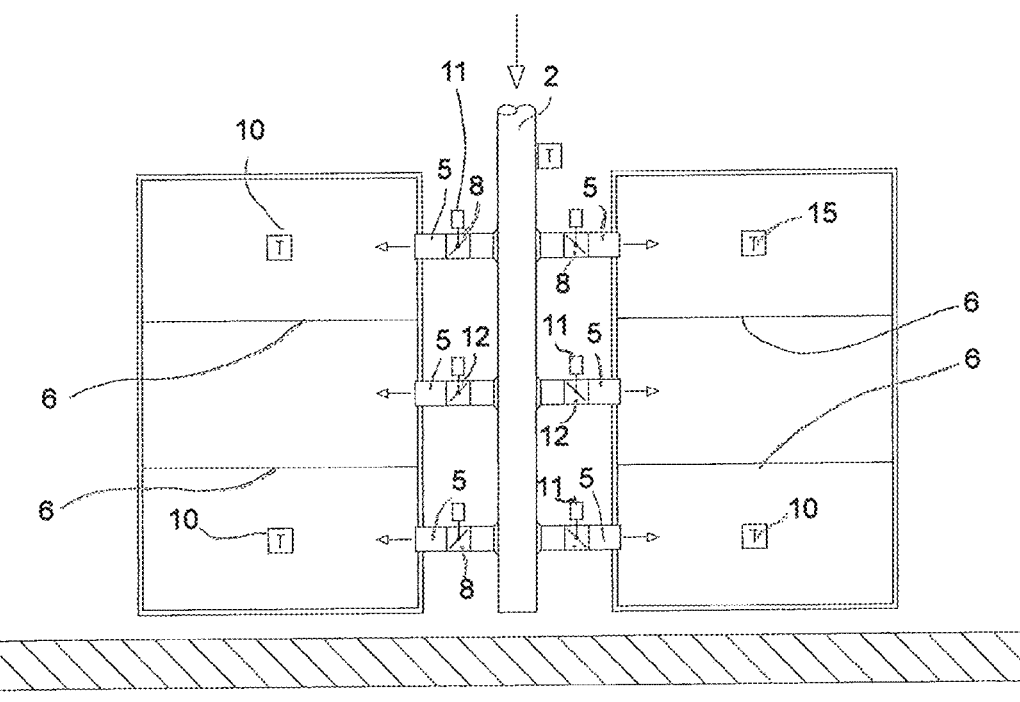
Fig. 4

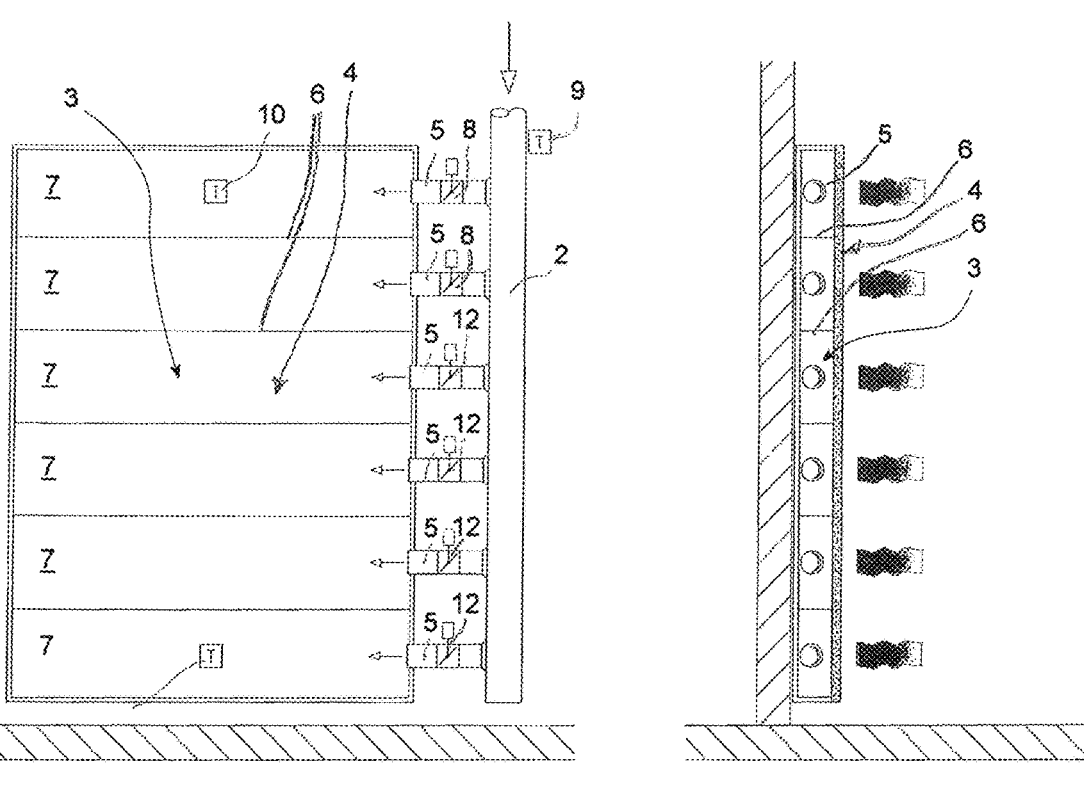
Fig. 5                              Fig. 6
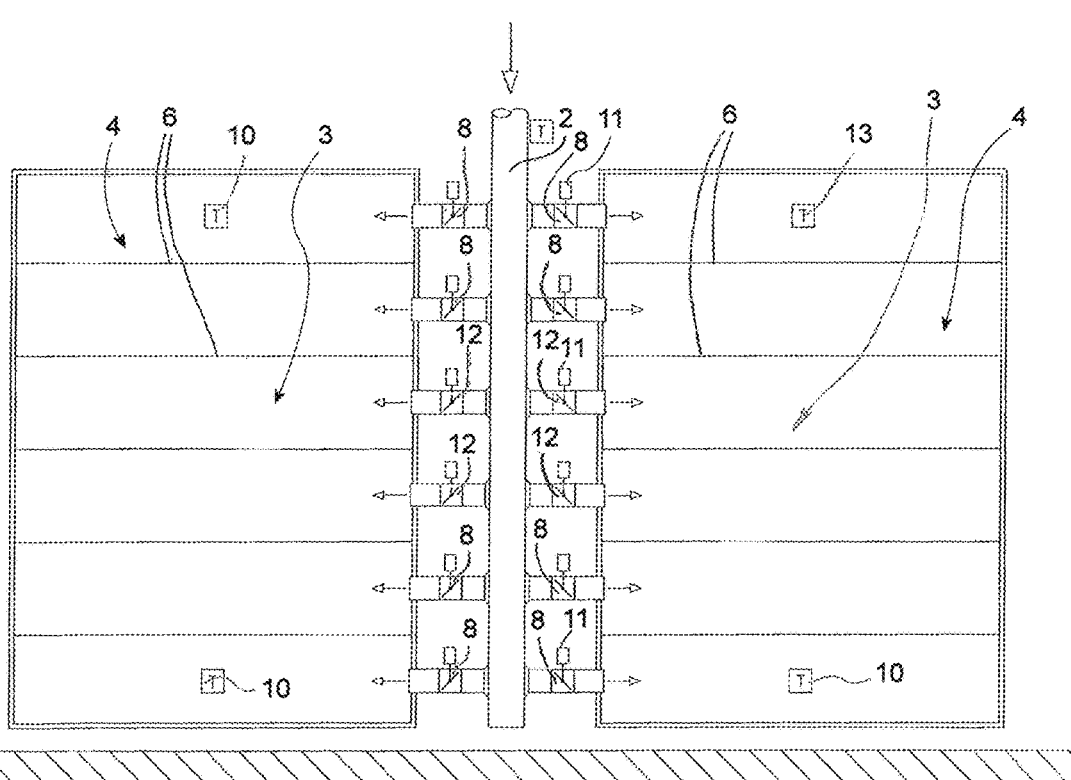
Fig. 7

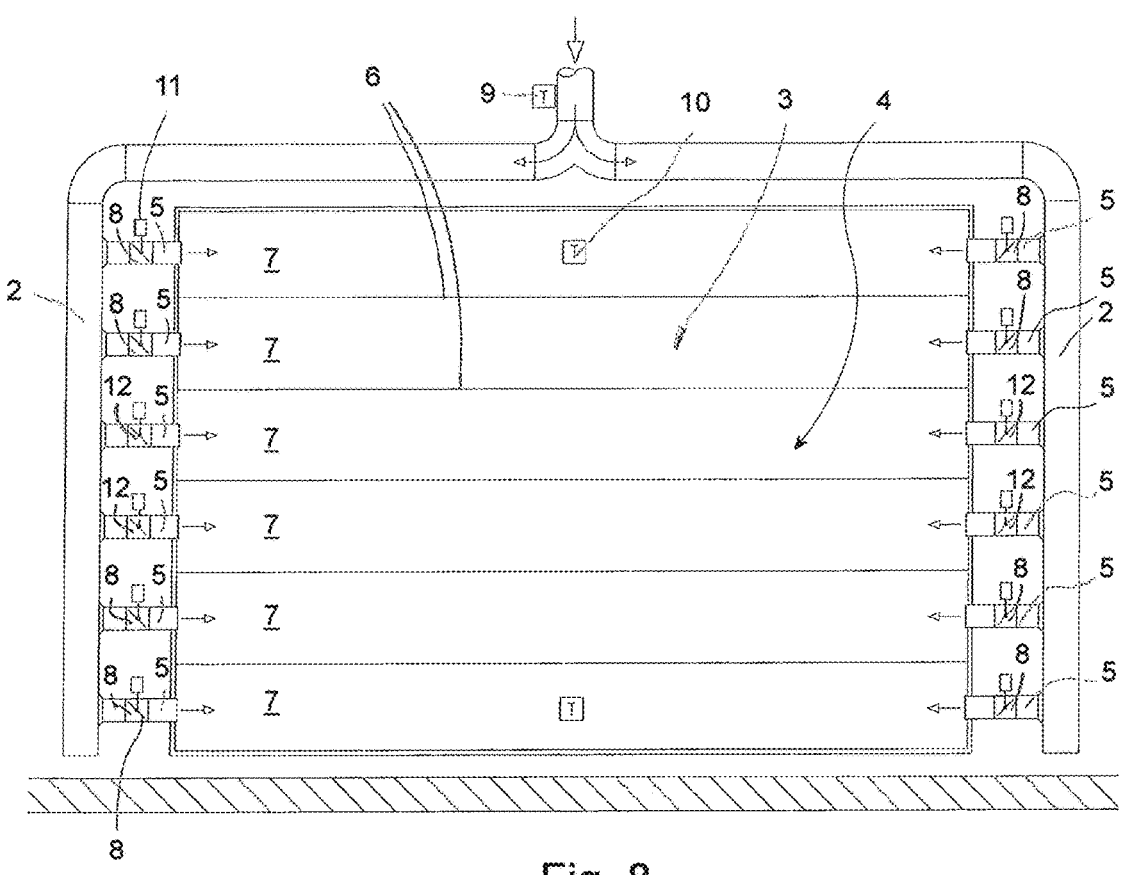
Fig. 8
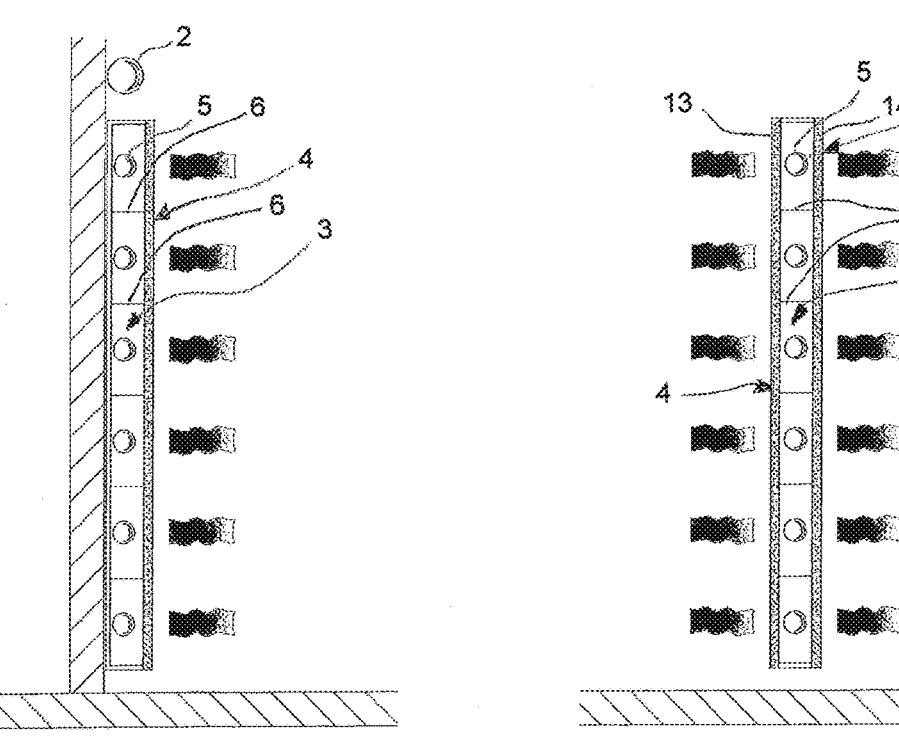
Fig. 9                           Fig. 10

SECTION I-I

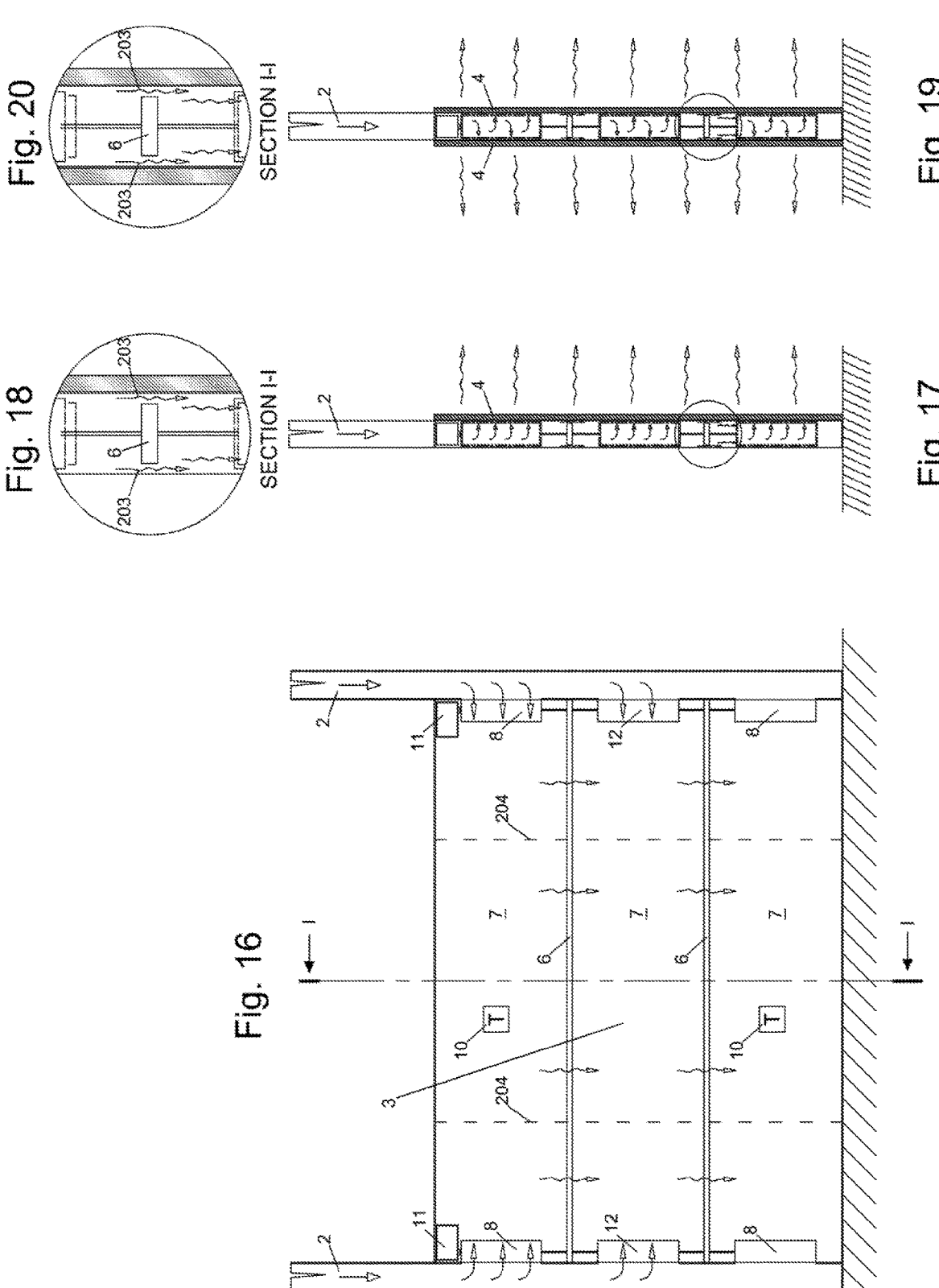

SECTION I-I

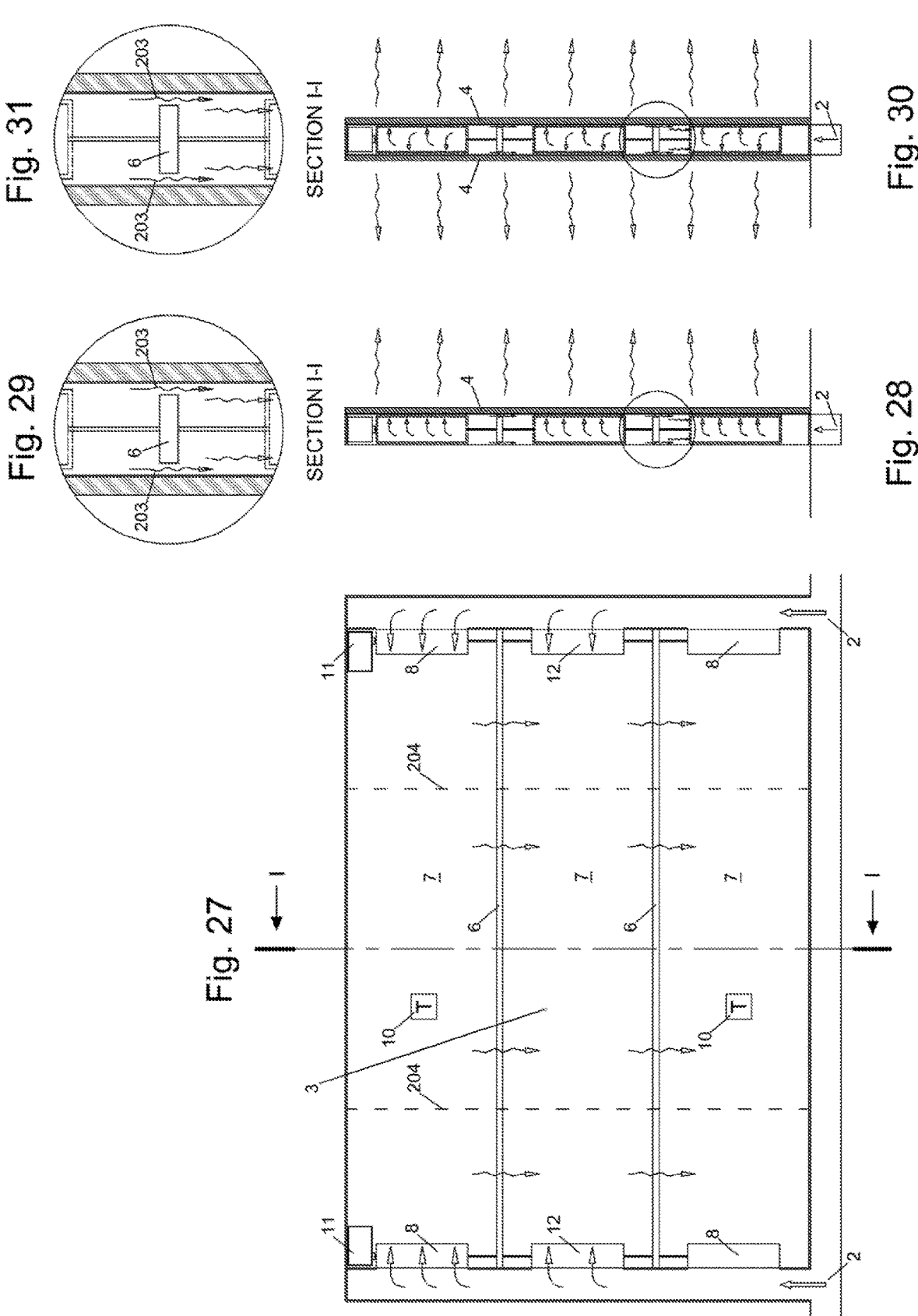

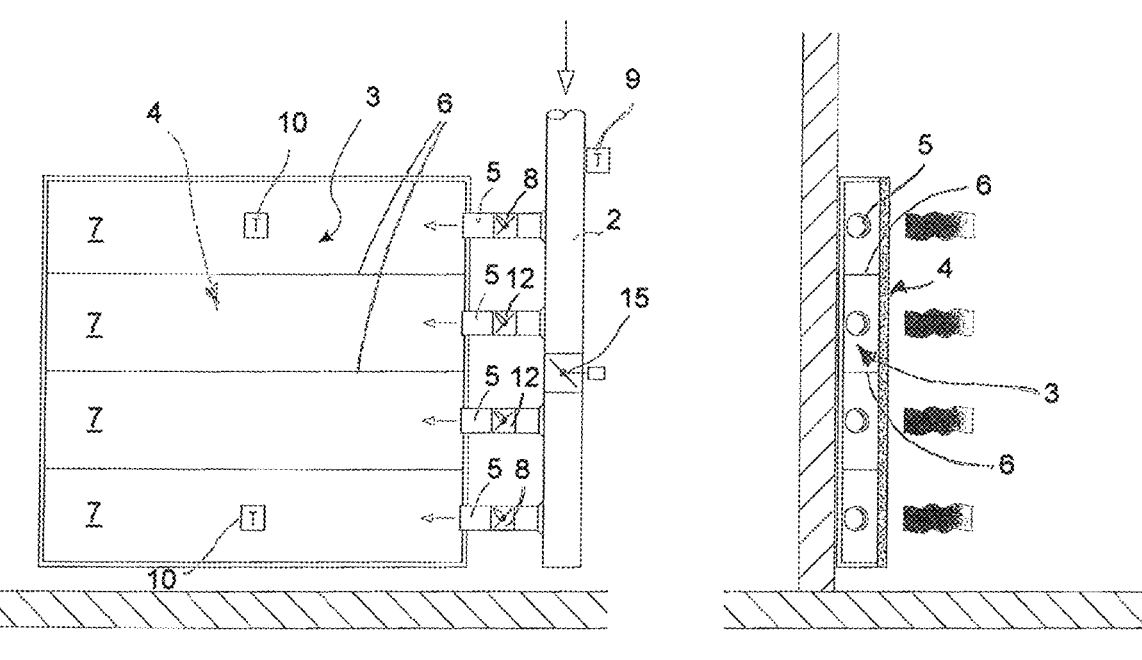
Fig. 33                                Fig. 34
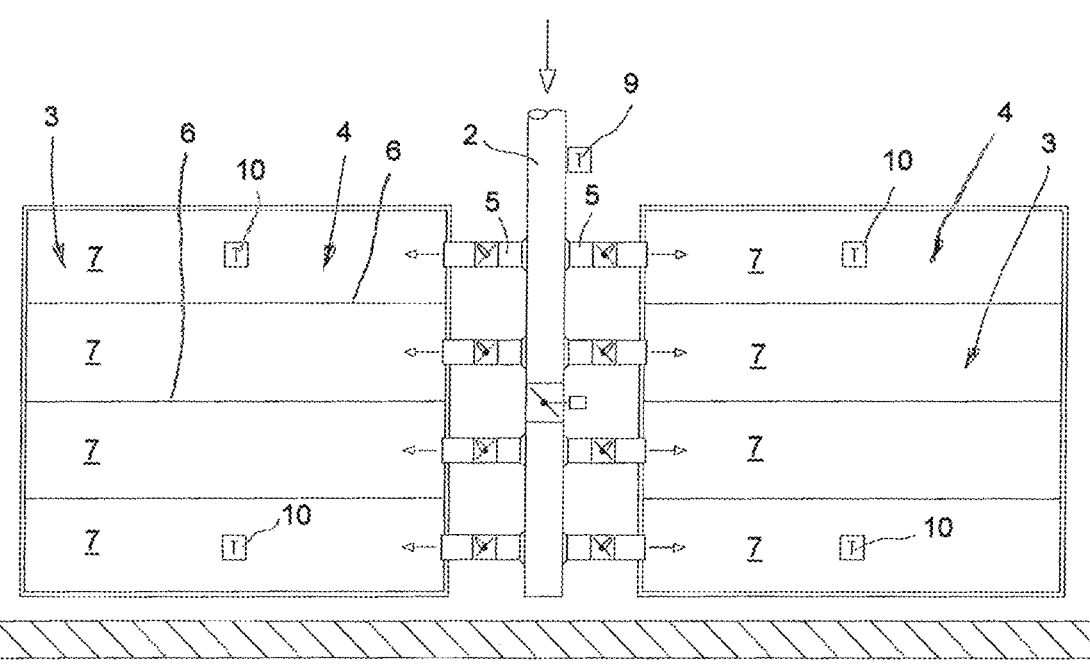
Fig. 35

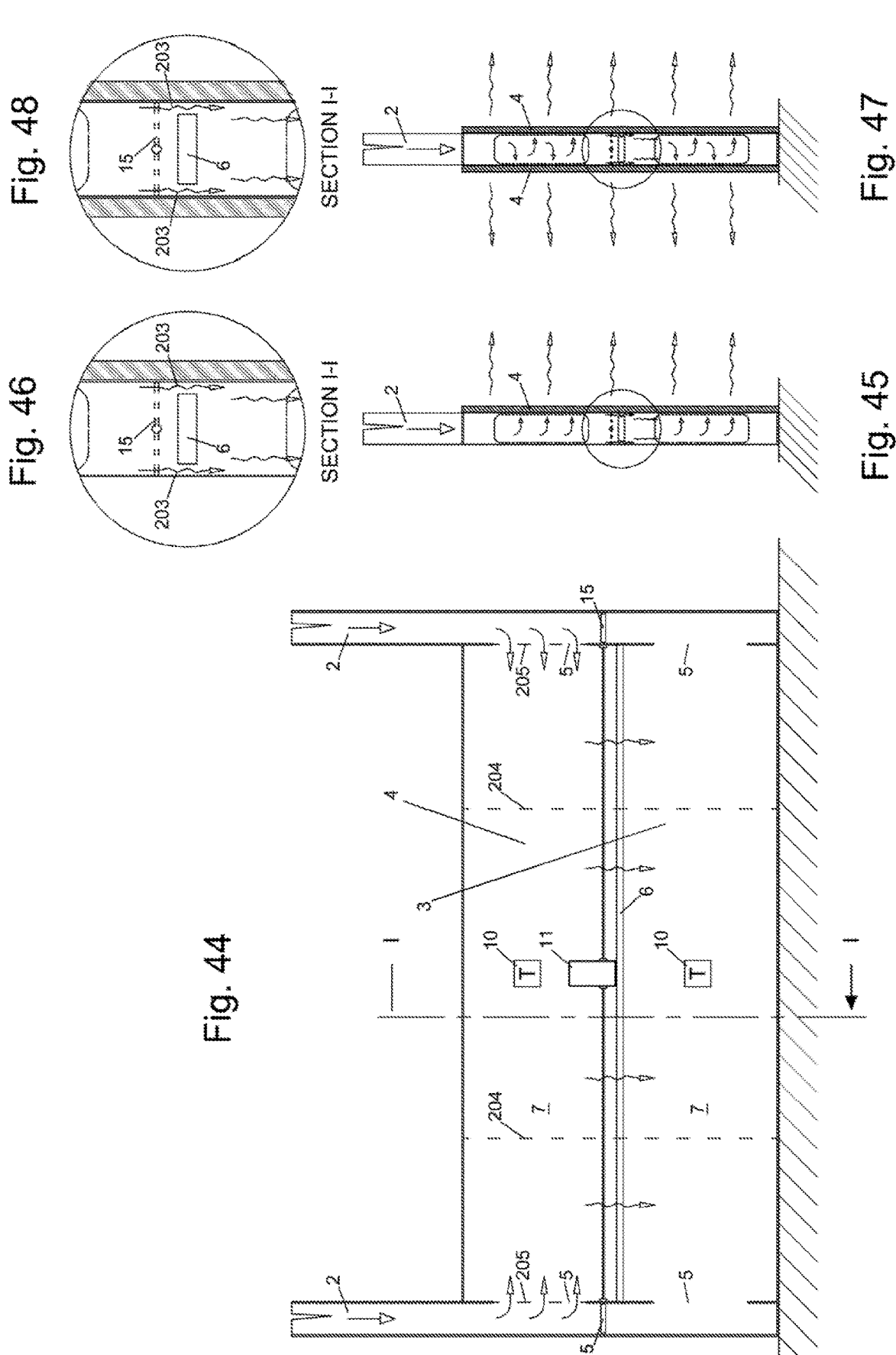

SECTION I-I

Section A—A

Section A—A

Section A—A

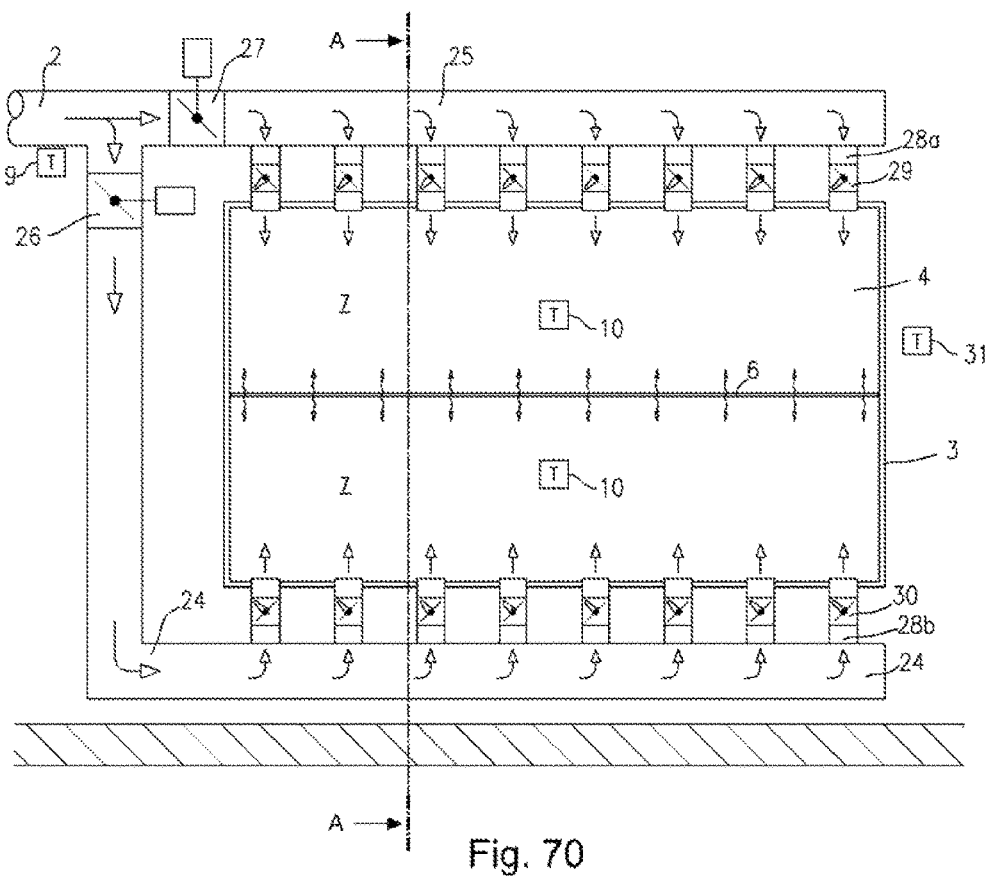
Fig. 70
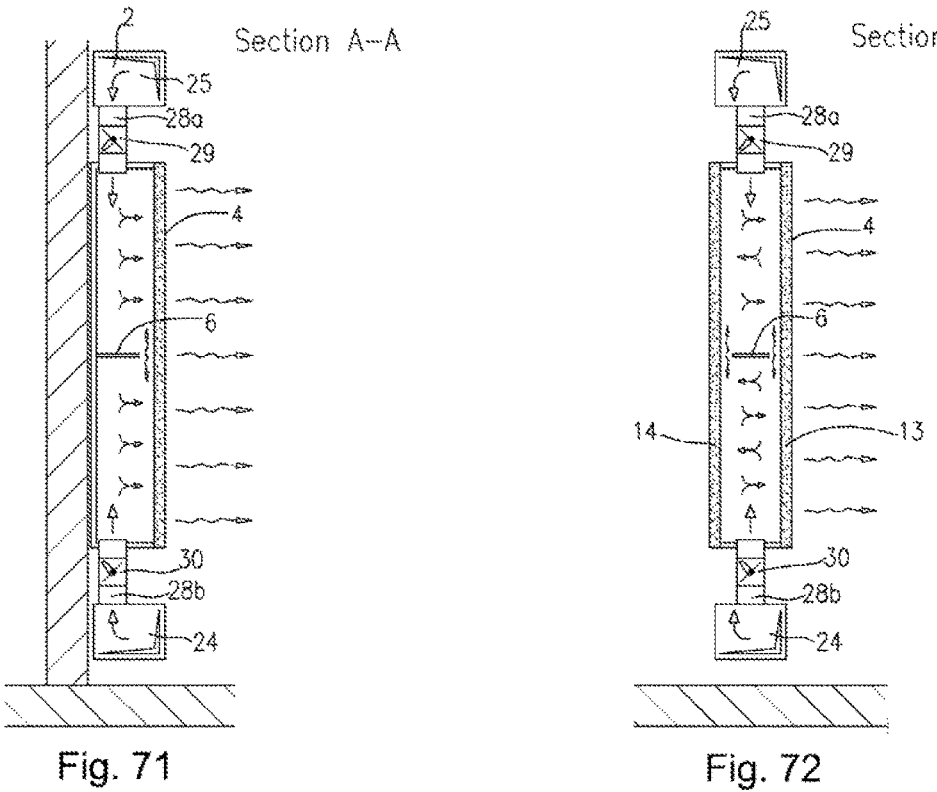
Fig. 71                              Fig. 72

Section A-A

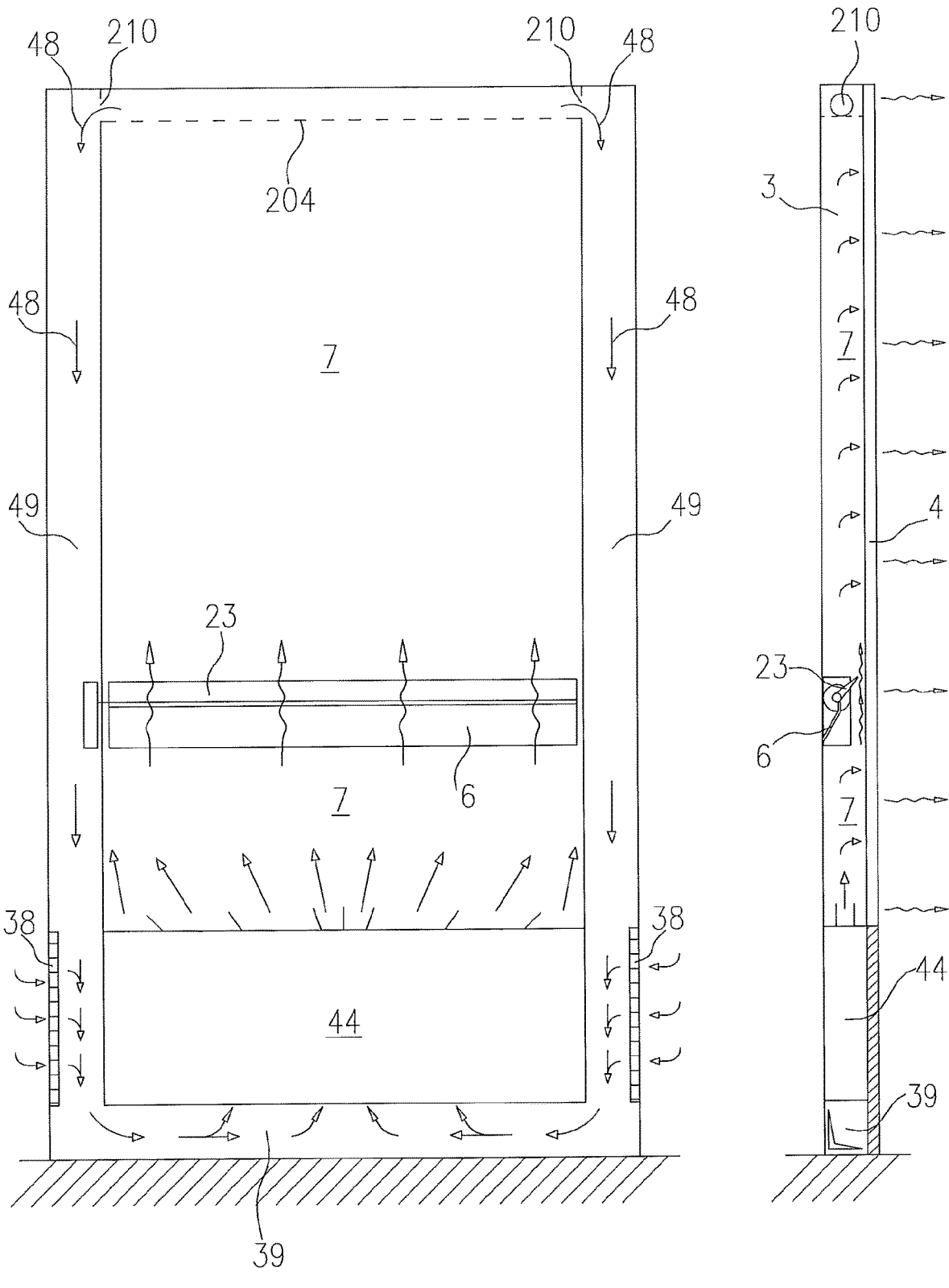
Fig. 100                    Fig. 101

AIR CONDITIONING SYSTEMS FOR ROOMS

1) TECHNICAL FIELD OF THE INVENTION

The present invention relates to air conditioning systems which can be used in all seasons, for air change, to achieve the healthiness of indoor rooms, improving the comfort and health of their occupants. Furthermore, the aforesaid air conditioning systems can also have acoustic absorption features, customisable aesthetic aspects, and a lighting device for the room in which they are installed.

2) Acronyms and Terminology Adopted

In the following descriptions, the following acronyms or terminology will be used, which are specified below:

HVAC, acronym for Heating, Ventilation and Air Conditioning;

air conditioning, understood as the set of processes that can be achieved with systems more universally called HVAC, which can therefore comprise, in addition to temperature control, also control the of humidity and the renewal/quality/healthiness of the air, of indoor rooms in the various seasons of the year;

AHU, acronym for air handling unit;

FCU, acronym for fan coil unit, or fan coil;

aeraulic duct, is a duct or conduit for the delivery and/or suction of air, in our case for air conditioning;

pressure drop, i.e., static pressure loss due to continuous and localised air motion resistances in the aeraulic system considered;

air permeable, referring to surfaces, panels, structures, etc., means an element that allows the passage of air due to porosity or the presence of perforations, which allow the passage of air;

hydronic, referring to panels, or to a system, indicates that a fluid containing water or with similar features is used;

direct expansion, referring to a system, indicates that the refrigerant fluid from the refrigeration unit/heat pump is used directly;

energy-efficient systems of the LTH—HTC type, acronym for low temperature heating—high temperature cooling, i.e., characterised by a small difference in temperature (more or less) with respect to the temperature of the room to be treated;

TABS-type systems, acronym for Thermally Active Building System, radiant component systems that exploit the thermal inertia of building structures to accumulate energy and obtain a thermal flywheel effect.

3) State of the Art and Problems to be Solved

Among the known systems frequently used for air conditioning with room air change, we find the so-called air HVAC systems, where in essence the control of all micro-climatic quantities such as temperature, relative humidity, purity and air velocity is carried out through the use of air treated by special air handling units (AHU) or fan coil units (FCU), carried by a system of distribution channels and introduced into the room by diffusion terminals, which can be of various types, located in the rooms to be treated.

For the purposes of air conditioning with air change in indoor rooms, air systems are the simplest and most effective to implement, however they are not free of defects, with the main defects described below.

An intrinsic defect of air systems is the relatively intense air currents that form both near the air outlet terminals and in general in the conditioned area and which, especially when the system is running in cooling, can cause discomfort and malaise to the people present in the room. Another defect is that in order to be able to affect the volume of the treated room, the air diffusion terminals must introduce air with swirling movements at high speed to obtain inductive mixing effects and have a throw, i.e., a sufficiently long range, which can be noisy.

A rather critical condition of the air systems is when they operate in heating. A typical defect that occurs during heating is the stratification of hot air that tends to form in the height of the room, which can cause:

discomfort to the occupants due to the sensation of cold feet and warm face;

ventilation inefficiency in relation to the renewal of the room air, due to the transit of the air in the upper part of the room, not occupied by people, with a consequent tendency to be re-sucked by the air intake of the system without having adequately removed the stale air from the occupied area, which therefore remains polluted;

energy inefficiency, due to the vertical thermal gradient that causes a greater unnecessary heating of the upper part of the rooms, not occupied by people.

3.1) Hybrid Air Conditioning Systems

In order to overcome the aforesaid problems, so-called hybrid systems are often built nowadays, consisting of several systems that work in combination, especially in the context of energy-efficient systems of the LTH—HTC type.

Among these, one of the most frequently used consists of a radiant panel system provided with water-fed coils, often located on the ceiling to have a good efficiency even in cooling, integrated by an air system that provides controlled mechanical ventilation for air change, summer dehumidification and possible winter humidification, as well as a possible thermal integration if the radiant panels, in limit conditions, fail to meet the necessary sensitive thermal needs.

However, the aforesaid hybrid systems, consisting of two or more systems that must integrate with each other, also with the related logic and automations, as well as a construction configuration, involve system complications and increased costs for both construction and operation and maintenance. Furthermore, the radiant panel system with water coils is characterised by a series of potential problems of hydraulic circulation due to the possible biological and algae formations typical of low-temperature heating systems, which can also obstruct the small diameter pipes of the coils, the manifolds and the calibration valves of the circuits, as well as potential difficulties in venting the air inside the coils, which thus require a high water passage speed therein for dragging the air to the venting points. For this reason and for heat exchange needs, the hydraulic circuits feeding such coils are typically sized with a temperature difference of the water between the back and forth of the circuit of only three degrees centigrade, against a temperature difference nowadays generally used to size a hydraulic circuit per handling unit of an air system of six degrees centigrade and above. It follows that the water flow rate for a circuit with radiant panels is at least twice that necessary for an air system, leading to an increase in energy consumption due to the high flow rates and head necessary for the pumping system.

Another negative aspect of water-based radiant panels is that the coils are made almost exclusively of plastic materials and on average about 20 metres of plastic pipes are used for each m$^2$ of radiant panel. From an ecological point of view, it should be considered that the pipes inside the radiant panels, in addition to being built with plastic materials, in almost all cases are difficult to separate for recyclability at the end of life, as they are usually incorporated and strongly glued within plasterboard or other types of panels.

3.2) all-Air Conditioning Systems

The complications set out above and others, related to the aforesaid hybrid systems, suggest that the ideal system would be an air system without a further water-based radiant panel system, i.e., an all-air system, which solves, however, the main problems related to the air systems already explained at the beginning of chapter 3).

To overcome the problem of annoying air currents, several solutions have been studied and patented over time.

3.2.1) Vertical-Extension Displacement Systems.

CN105910216A

In patent application CN105910216A, an air distribution element is described, placed near the side walls of a house, consisting of an air supply channel for air conditioning and air change of the room and a terminal element for the relative diffusion of air in the room, in order to obtain an effective, comfortable and healthy air change and conditioning also from the point of view of $CO_2$ concentration.

The duct feeds a rear chamber about 40-60 mm thick, which is divided vertically by longitudinal baffles positioned at 40-200 mm from each other and by partitions placed at 10-30 mm from the perforated panels.

In section B-B, the partitions have interruptions along their vertical path to allow the passage of conditioned air from the rear chamber to a front chamber, which has horizontal closures to separate in height the vertical air ducts feeding the perforated panels that introduce air into the room.

The function of the vertical baffles is to capture the incoming air from the air conditioning supply channel and direct it downwards, while the partitions and ducts separated in height, form paths to distribute the air evenly over the entire surface of the perforated panels.

Said partitioning walls and vertical and horizontal partitions are therefore fixed distribution systems necessary to distribute the incoming air uniformly from the air supply duct, along the entire surface of the perforated panels that introduce the air into the room.

As explained below, the adoption of fixed calibration means involves critical issues due to the non-adaptability of the system to changes in flow rates and conditioned air temperatures.

CN204535005U

Utility model CN204535005U discloses an air change device basically consisting of an outer cylindrical shell with a mesh surface, fed from above by a conditioned air supply duct and operating as an air diffusion terminal.

The device comprises a regulation apparatus therein with ring-shaped throttling plates to adjust the air flow and a panel, which can be lifted by means of a fixed pulley along a vertical guide rod, to adjust the air deflection in the lower part only.

According to CN204535005U, such a regulation apparatus allows for arbitrary regulation, within specific limits, of the direction of the resulting flow of the conditioned air exiting the outer surface of the shell.

The device of CN204535005U is not provided with divisions into internal partitions and air distribution variation systems as the relative temperature varies, which allow the supply air to be introduced mainly or exclusively into the lower part of the diffuser, a function which is instead necessary for correct operation even in heating.

The utility model CN204535005U is part of the type of displacement systems and therefore suffers from the criticalities of these systems presented later, in addition to being without a specific sound absorption function.

U.S. Pat. No. 4,316,406A

Patent U.S. Pat. No. 4,316,406A discloses a generic air distribution element of rectangular shape that is used to diffuse cooled air, without air currents, mainly in industrial rooms.

A chamber is connected, through a series of holes in an internal partition, to an antechamber fed by a duct for cooled air. The holes on the aforesaid partition are equipped with projections towards the antechamber, or special nozzles, for the collection of the air flow. The room also has a permeable screen through which the cooled air flows into the room.

In U.S. Pat. No. 4,316,406A, it is specified that as a result of the air exiting the diffuser at a speed of less than 0.3 metres per second, the air flow will be laminar and will have low kinetic energy. Therefore, the air must not have a temperature higher than the that of the room temperature. Instead, the workplace can be heated by, for example, air heaters or radiators.

DE-A-44 21 167

Patent application DE-A-44 21 167 describes an element for distributing cooled air, without annoying air currents for the occupants, comprising a chamber delimited on the face towards the room by two parallel layers of fabric spaced apart from each other.

The systems referred to in documents CN105910216A, CN204535005U, U.S. Pat. No. 4,316,406A and DE-A-44 21 167 described above are part of the type of known air diffusers that are used for the creation of displacement systems.

The solutions described in these documents are not equipped with sufficient measures to ensure a uniform distribution of air on their surface as a function of the temperature of the supply air and as the flow rate of the latter varies. The natural behaviour of hot air is to move upwards, vice versa that of cold air; this behaviour inside an aeraulic duct becomes more marked as the air flow decreases, in that as the air speed decreases the resistance to the passage of air decreases exponentially, which then becomes more subject to natural behaviours due to its temperature.

With supply air at a sufficiently hot temperature to heat the room, the air tends to exit more in the upper part of the diffuser and vice versa in the case of very cold air, while it would be appropriate to notably move the air flow towards the lower part of the diffuser during heating and uniform it over the entire height during cooling.

The adoption of fixed calibration systems, such as the partitioning walls and dividing walls indicated in document CN105910216A, limits but does not solve the problem of the thermal stratification of the air inside the apparatus, as it does not allow to vary the air distribution along the height of the diffuser upon the varying temperature and air flow rate.

Traditional displacement systems are not adapted to avoid the vertical stratification of hot air in the room and therefore are not suitable to operate in heating. They find ideal application in rooms characterised by the presence of areas occupied by heat sources and polluted air to be removed. In order to fully affect the room, the introduction of air must occur at a lower temperature than that of the room, since the air must be able to descend to the floor and flow along the same floor, before being dragged upwards by the plumes generated by the thermal sources present in the room.

The air intake must be positioned in the highest part of the room, to suck and expel the polluted air that has risen as a result of the thermal sources encountered.

Due to the operating principles explained above, displacement systems are not naturally suitable for heating; therefore, the latter must be made with other separate systems; the displacement is substantially used to remove the thermal loads and check the air quality.

The temperature of the supply air of the diffusers must not be much colder than that in the room in the area occupied by people, because the cooling air exits the diffuser almost at the same temperature at which it enters the diffuser itself, as it is not subject to appreciable pre-heating (due to thermal exchanges with the room by convection and radiation) before exiting the diffuser or immediately adjacent to its introduction surface, furthermore the air exiting with almost laminar motion does not undergo mixtures by induction, consequently an overly low supply temperature would correspond to an introduction temperature that could cause annoyance to people.

With this type of systems in civil rooms, the operating under-temperature, i.e., the maximum temperature difference of the introduction air with respect to that of the occupied area, is normally between −2 and −5 degrees Kelvin (or Celsius); consequently, modest thermal loads can be removed around 40-50 W/m2 (watt per square metre).

In structures characterised by more intense activities and high heights of the rooms, such as industrial rooms, the introduction under-temperature for cooling and ventilation can also increase up to −8 degrees Kelvin, or Celsius, thus it is necessary to pay close attention to the positioning of the diffusers, which must not create discomfort in the areas occupied by people, also considering that each air diffuser is characterised by its own proximity area where there may be a risk of air currents for the occupants and that if more diffusers are placed close to each other, the proximity area increases in extension.

3.2.2) Systems with Large Surface Area Diffusers and Low Air Diffusion Speed, with Horizontal Extension.

U.S. Pat. No. 6,602,129B1

Air-cooling elements are described in U.S. Pat. No. 6,602,129B1, in order to obtain a high cooling power without creating annoying currents of cold air, equipped with a cooling wall exposed to the room to be cooled, made of metal sheet less than 1 mm thick having holes of small diameter, even less than 0.6 mm and typically from 0.5 to 0.6 mm, typically arranged according to a 5 mm side lattice, which represent a passage surface even not exceeding 1% of the wall area. An antechamber is also included in which, through a special distributor in turn provided with small holes, a swirling and highly turbulent movement of the air must be produced to ensure a good heat exchange and a uniform distribution therein. The operation of the apparatus is essentially based on the vortex and turbulence of the air in the antechamber, caused by the high speed of the air exiting the holes of the relative distributor and the high exit speed of the air towards the room, through the micro-holes made on the cooling wall, resulting in high induction and mixing with the room air.

Said features, under nominal flow conditions of 45 m³/h², determine a loss of static pressure (pressure loss) in the supply air, of 60 Pa in the diffuser inside the cavity and ⅓ of such a value, i.e., 20 Pa, in the crossing of the cooling wall, which added to the residual 10 Pa necessary to allow the exit of air into the room lead to a total 90 Pa of static pressure necessary at the entrance of the cooling element, to have the correct operation of the unit in question.

A defect of the aforesaid system is that such a high supply pressure required upstream of the air diffuser, to be added to the pressure necessary to overcome the pressure losses of the rest of the air system upstream of the diffuser, involves some drawbacks, such as:

adoption of air handling units provided with high-head fans, which in addition to being characterised by higher electrical absorption are also noisier, compared to low-head fans; the need to resort to high-head fans also often prevents the use of fan-coils units (FCUs or fan coils) of the ductable type, equipped at most with medium-head fans, leading only to the adoption of AHU type handling units, which are bulkier and more expensive;

the aeraulic ducts placed upstream of the diffusers, subjected to a higher static pressure, are subject to greater losses of air from the small sealing imperfections of the ducts themselves that are always present in reality.

Another limitation of the elements referred to in U.S. Pat. No. 6,602,129B1 is that each diffuser has a dimensional surface limit due to the shape of the cooling wall provided with micro-holes, made by means of a simple sheet of thin sheet metal, which beyond a given dimensional limit deforms due to its own weight and the thrust of the air introduced upstream, equal to the resistance which the air encounters when passing through the micro-holes.

The consequence is that many diffusers are required for relatively large rooms, each equipped with its own chamber with internal air distributor, leading to a complication and increased costs.

Furthermore, such panels require being supplied with a limited range of air flow rates as:

the maximum flow rate is limited by the features of the distributor inside the chamber and the micro-perforated sheet from which the air exits towards the room, described above, in fact the aforesaid diffusers, with air flow rates greater than values of the order of about 45 m3/h per m2 of gross diffuser surface, suffer from problems of high noise and an exponential increase in static pressure losses, with consequent unacceptable energy consumption due to the necessary head which the fan must develop;

the minimum flow rate is necessary to maintain the vortex motion required inside the chamber in front of the micro-perforated panel and to preserve the inductive effect of the air exiting the micro-holes towards the room.

For these reasons, in some cases the maximum air flow rates that the diffusers of U.S. Pat. No. 6,602,129B1 are capable of introducing into a room, may not be sufficient to meet the needs of an air system, needs that can also be those related to free cooling by air, which in turn requires high air flow rates.

In other cases, for example for air conditioning rooms with limited thermal demand and thus reduced air flow rate requirements, the minimum air flow rates introduced would determine a use of a limited number of diffuser panels, which may be insufficient to effectively cover the total surface area of the room for the purpose of completely replacing the exhausted air throughout the room.

U.S. Pat. No. 8,480,463B2

Patent U.S. Pat. No. 8,480,463B2 relates to a flat element for the thermal regulation of a room, in particular for cooling the air of the room, with a preferably ceiling-mounted embodiment. As substantial features and operating principles, it is similar to the U.S. Pat. No. 6,602,129B1 described above and constitutes in practice a different solution, designed in order to simplify its creation and reduce its costs.

The supply air from an air conditioning system is introduced into a chamber placed above the micro-perforated sheet for introducing air in the room; in the upper chamber, through special baffles consisting of a bent sheet, a strong turbulence is generated to uniform the distribution of air therein, then the air passes at high speed through the small holes in the sheet, to be introduced into the room.

The substantially common features of the two patent solutions mentioned above also share the relative functional disadvantages and application limits, already described in relation to U.S. Pat. No. 6,602,129B1.

Another feature of the diffusers referred to in U.S. Pat. No. 6,602,129B1 and U.S. Pat. No. 8,480,463B2 is that, since they consist of low-thickness metallic materials, they are not provided with significant thermal inertia, which, however, as will be specified below, could be useful in some applications, especially for systems operating in a heat pump; moreover, before being introduced into the room the air does not in any way affect significant masses of material or even building structures, thus it is not possible to use it even for TABS type building/plant systems.

U.S. Pat. No. 2,172,771A

U.S. Pat. No. 2,172,771A has a ventilation system for cooling or even heating rooms with panels arranged on a large area of the ceiling, for the distribution of air without annoying currents. These panels can be made of fibrous material and/or with small holes, also with sound-absorbing features, and are fed through a supply chamber, or plenum, arranged behind the panels themselves. Inside the supply chamber it is necessary to have a certain overpressure to ensure the passage of the air through the panels. To maintain sufficient overpressure in the supply chamber, and to obtain a good uniformity in the air passage on the entire surface of the ceiling from which the air must exit, the panels must be made so as to create a certain resistance to the passage of air, furthermore, always to uniform the exit of air from the entire surface of the ceiling, some methods of partial closure of the air passage surfaces are indicated, through panels impermeable to the passage of air, to balance the pressure losses of the ceiling parts where more air tends to pass with those where it tends to pass less.

According to a practical example described in U.S. Pat. No. 2,172,771A, in a room where there are a series of panels each with an area of 0.186 square metres (2 square feet), the perforated part has a total area of 32.50 square metres (350 square feet) and the ventilation air flow for the room varies between 14 and 99 cubic metres per minute (500-3500 cubic feet per minute), the application of panels impermeable to air that are 1.81 cm (one-half inch) smaller, both in length and width, of the panels from which the air passes, have been satisfactory for making the exit of air from the ceiling uniform.

U.S. Pat. No. 2,291,220A

Another ventilation system for cooling or even heating rooms is illustrated in U.S. Pat. No. 2,291,220A, also based on panels arranged on the ceiling with holes or porosities that allow the passage of air in the room without creating annoying air currents, with sound-absorbing features, which are fed through a supply chamber (plenum) arranged above the panels. For the uniform operation of the system, it is explained that with a flow rate of 72 cubic metres per square metre of ceiling, a maximum free air passage surface of 1.8% and preferably a maximum of 1.2% is required. In the claims it is indicated that such a free surface must be less than 4% or 1%, with a static pressure in the plenum between 2.49 and 124.5 Pascal (0.01 and 0.5 inch of water) or between 4.98 and 37.4 Pascal (0.02 and 0.15 inch of water). The description explains that to uniform the exit of air on the whole surface of the ceiling it is in some cases necessary to close the air passage through some parts of air diffusion in the room above the ceiling.

The aforesaid patents U.S. Pat. Nos. 2,172,771A and 2,291,220A are substantially similar to each other. In both, in various cases, especially when the free air passage surface is high in relation to the air flow that must pass through it, to uniform the air passage through the ceiling of its introduction throughout the room, it is necessary to occlude some parts of the introduction surface that are more favourable to the passage of air with respect to others. Such reductions in the surface and/or air passage section above the air diffusion ceiling in the room are calibrations for balancing the uniform distribution of air in the plenum and/or in the room, of a fixed type; once these fixed calibrations have been made, these cannot be quickly modified, let alone automatically regulated for the uniform distribution of air on the surface of the active ceiling as the supply air flow rate and the relative temperature vary. This also limits the possible adoption of regulations of the variable air flow rate type because by reducing the supply air flow rate, the self-regulating effect of the pressure losses due to the calibrations loses authority with respect to the natural tendency of the cold air throw drop and vice versa of the floatation of the hot air. The colder the air, the more it tends to fall near the air inlet in the plenum, thus favouring the cooling below these parts of the ceiling. Conversely, the warmer the air, the more it tends to float inside the plenum, moving farther away and favouring its exit from the parts of the active ceiling farthest from the air inlets.

In addition to the above, the two patents U.S. Pat. Nos. 2,172,771A and 2,291,220A during possible use in the heating step would markedly suffer the problems already described related to the stratification of hot air in the upper part of the rooms, i.e., discomfort to the occupants, ventilation inefficiency and energy inefficiency.

3.2.3) Conclusions Related to all-Air Conditioning Systems.

As can be seen from the above analyses of the state-of-the-art documents, the solutions examined, related to air systems, solve the problem of annoying air currents, but do not solve the critical issues resulting from heating operation and are not equipped with sufficient measures to ensure an adequate distribution of the air on their surface as the temperature and flow rate of the supply air vary.

Furthermore, with the diffusers of the above documents CN105910216A, CN204535005U, U.S. Pat. No. 4,316, 406A, DE-A-44 21 167, U.S. Pat. No. 6,602,129B1, and U.S. Pat. No. 8,480,463B2, there is no specific sound absorption function envisaged and in any case any sound absorption provided may not be adequate or adaptable to the needs of the room in which they are installed.

The current state of the art is therefore still in need of improvements and implementations in further aspects in addition to that of annoying air currents, also because compliance with recent, as well as in the near future, regulatory standards for thermal comfort, indoor air quality, energy performance and savings, acoustics and lighting, of indoor rooms is increasingly required, in addition to the directives for the use of recycled and/or recyclable materials in buildings, which are taken into high consideration by the certification protocols related to the general quality classification of buildings.

4) Objects of the Invention

The object of the present invention is to improve the state of the art in the HVAC sector by providing an improved type of air system which solves the typical criticalities of such a type of systems, to constitute a valid alternative to the current frequent need to resort to hybrid plant systems consisting of an air system and a radiant panel system, already described in chapter 3.1).

The present invention aims to achieve the above-described object by creating forced air HVAC systems totally free of the problems related to annoying air currents and the incorrect thermal stratification of the air, without having to resort to the addition of further systems with water-fed radiant panels, but which also have significant radiant features and which also have the following additional characteristics: they are effective and efficient both for air conditioning and for air change even during heating and that they are inherently silent.

These and other objects of the present invention are achieved by an air conditioning system according to claim 1 and claim 3.

The dependent claims refer to preferred and advantageous embodiments of the invention.

5) BRIEF DESCRIPTION OF THE DRAWINGS

Further features and advantages of the present invention will become apparent from the detailed description of preferred, non-exclusive embodiments according to the present invention, given by way of non-limiting example, in the appended drawings in which:

FIGS. 2 to 10 illustrate some embodiments of the multifunction apparatus according to a type of vertical versions of the present invention;

FIGS. 11 to 32 illustrate a specific application made according to the fundamental principles of FIG. 8

FIGS. 33 to 38 illustrate other embodiments of the multifunction apparatus according to another type of vertical versions of the present invention;

FIGS. 39 to 60 illustrate a specific application made according to the fundamental principles of FIG. 36

FIGS. 61 to 79 illustrate other embodiments of the multifunction apparatus according to further types of vertical versions of the present invention;

FIGS. 94 to 105 illustrate embodiments of the multifunction apparatus according to the present invention, which incorporate therein the typical components of a fan coil.

Figure 1A:
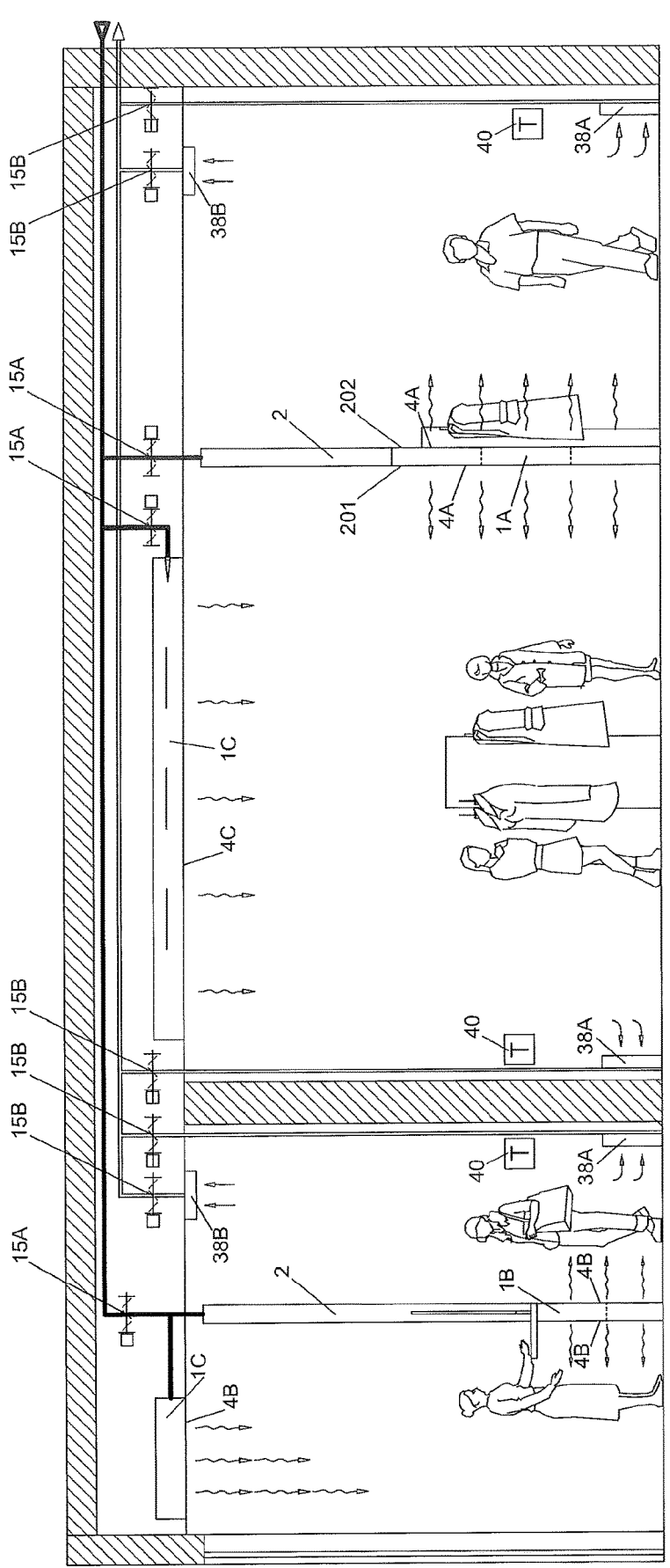
FIGS. 1A and 1B are the schematic sectional and planar indications, respectively, of a system structured in accordance with an embodiment of the present invention, applicable for example to a clothing store.

6) EMBODIMENTS OF THE INVENTION 6.1) Recitals.

With reference to the accompanying figures, some embodiments of innovative air conditioning systems have been illustrated which, using expedients and apparatuses forming part of the present invention, subsequently detailed in the relative chapters, allow the objects of the invention set out in the previous chapter 4) to be achieved, as well as the advantages listed below.

According to the present invention, the terminal elements placed in a room for the diffusion of air can have effective sound-absorbing properties for the acoustic improvement of the rooms in which they are inserted; they are characterised by limited pressure losses to be able to be fed with air at low static pressure; they are suitable for operating correctly even with variable air flows and temperatures.

An advantage of the present invention is that of being able to obtain air systems even in versions equipped with apparatuses with structures whose mass and thermal inertia act as a thermal flywheel suitable for applications in which this effect can be advantageous, for example for systems operating as heat pumps and/or for building systems/systems of TABS type (Thermally Active Building Systems).

Another advantage of the present invention is that of simplifying the design and construction of the systems with respect to hybrid plant solutions consisting of an air system and a radiant panel system, while maintaining competitive costs.

Another advantage of the present invention is that it also has strong room compatibility characteristics, reducing the use of plastic materials and relying on the effective and efficient use of easily recyclable materials and natural materials.

A further advantage of the present invention is that it allows to create systems equipped with particular characteristics of flexibility of use and possible operating self-adaptivity.

In order to achieve the objects and advantages described above, the innovative ventilation-conditioning system of room referred to in the present invention, uses apparatuses equipped with terminal elements for the diffusion of air in the room that in some cases can have front surfaces similar to those used for hydronic radiant panels and/or for sound-absorbing panels, for the relative traditional applications. This is both in order to manage to obtain an average radiant temperature of the surfaces of the room favourable to well-being, and to be able to have an effective sound-absorbing surface for the possible need for acoustic improvement of the room.

The large surface required to comply with such characteristics involves a series of problems to be solved, especially related to a correct distribution of the conditioned air on the surface of the terminal element that introduces the air into the room and the suitability of the distribution and air introduction system to operate correctly even with variable air flows and temperatures, while maintaining limited pressure losses to be able to feed it with air at low static pressure.

The aforesaid innovative system allows to solve the aforesaid problems and therefore to achieve the intended objects, by virtue of the use of particular specific apparatuses referred to in the present invention and the related optimisations of use and operation.

In order to allow its use in the most diverse types of rooms, the aforementioned specific apparatuses have been designed to be implemented in various embodiments, such as vertical extension and positionable, for example, along the side walls of a room or in the room itself, or with horizontal extension and positionable at a higher height such as, for example, on the ceiling or as an aerial island, all in forms that can also be modular and/or even combined with each other.

The inventive concepts shared by the various embodiments are the same, adopting optimised dynamic air distribution systems upstream of the relative permeable surfaces, to regulate the distribution of the conditioned air, as a function of the temperature and/or the supply flow, both inside the apparatus, and for the subsequent exit of the air at low speed towards the rooms to be treated.

Said apparatuses, allowing several functions to be combined simultaneously, are also called multifunction apparatuses. In fact, in addition to serving the typical functions of the most advanced HVAC systems, such as summer and winter air conditioning (with radiant component), dehumidification and humidification, ventilation, air change, free cooling, etc., they can possibly simultaneously fulfil other functions such as: thermal flywheel/accumulation in the mass, air sanitisation, room sound absorption, aesthetic-representative functions, as well as lighting functions.

The air conditioning systems according to the present invention can make use of air handling units of both the centralised AHU type and localised FCU type, i.e., fan coil, such apparatuses therefore constitute a source of conditioned air.

One or more aeraulic ducts or channels transport the conditioned air from the air handling units until it reaches the final part of the system near the room to be treated. At this point, the air conditioning constitutes the supply air for one or more multifunction apparatuses 1, referred to in the present invention.

The multifunction apparatuses 1, both in vertical and horizontal extension, are equipped with particular characteristics, among which the following stand out: the presence of specific expedients adapted to regulate/vary the distribution of the air conditioning therein and towards the room to be conditioned, also so as to allow the supply air to be mainly or exclusively introduced into the highest or lowest partition of the plenum, as a function of various operating parameters, such as the temperature of the conditioned air and/or the temperature difference between the conditioned air feeding them and the room and/or the heating or cooling and/or free cooling operating mode of the system, and/or the flow rate of the supply air and/or the need for exchange and/or sanitisation of the air of the room to be treated;

the presence of a terminal element, of variable type depending on the characteristics of the rooms to be served and the effects to be obtained, which interfaces for the introduction of conditioned air and simultaneously for heat exchanges with the room, as well as for other optional functions explained below.

Depending on the characteristics of the room to be treated, the multifunction apparatuses can have multiple embodiments, with configurations with both vertical extension, which can be positioned, for example, along the side walls of the room or in the room itself, and with horizontal extension, which can be positioned at higher heights, such as, for example, on the ceiling or as an aerial island.

Depending on the air flow rates necessary for air conditioning and the quality of the indoor air, the desired extent of influence of the average radiant temperature of the surfaces and, optionally, for the sound absorption suitable for acoustic improvement, as well as for the aesthetic result, of the specific room, different types of terminal elements are adopted, which lead to different surface ratios per unit of air flow to be introduced.

Keeping the front surfaces of the terminal necessary for what is described above, therefore not only for the delivery of air in the room as would be done for a traditional air conditioning system, for rooms that require high air flows to be introduced, for example industrial, terminal elements can be adopted that can have low pressure losses even with flow rates of 350 m³/h for each m² of front surface of the terminal element; on the contrary, for rooms that require low air flows to be introduced, suitable terminal elements are available for flow rates up to only 8 m³/h for each m² of front surface of the terminal element.

With a view to seeking the right cost-benefit ratio, by means of laboratory tests it has been found that:

the front surfaces of the terminal elements must have a minimum cm2 surface area each m³/h of air flow that passes through them to be introduced into a room, which progressively varies according to the type of room in which they are located; the values that have been found to be more suitable for the purpose on average are: at least 500 cm2 per m³/h in the case of rooms with low air flow demand; at least 250 cm2 per m³/h for rooms with medium air flow demand; at least 100 cm2 per m³/h for rooms with medium-high average air flow demand; at least 50 cm2 per m³/h for rooms with high air flow demand; at least 40 cm2 per m³/h for rooms with very high air flow demand; by virtue of these values of the surface of the terminal elements in relation to the air flow it is possible to obtain a radiant average temperature of the surfaces of the room to be treated which favour well-being, and/or it is possible to have an effective sound-absorbing surface for any need for acoustic improvement of the room, while maintaining the correct distribution of air within the plenums and related partitions, as well as the correct introduction of air into the room and the maximum efficiency and effectiveness of the system in all operating conditions of the system;

to limit electrical consumption and noise, the multifunction apparatuses as a whole of its components, including plenums, partitioning walls, partitions, air distribution systems, terminal element, are characterised by low static operating pressures that are progressively variable depending on the type of room in which they are located. The optimal pressure loss values are: less than 15 Pa in the case of rooms with low air flow demand; less than 20 Pa for rooms with medium air flow demand; less than 35 Pa for rooms with medium-high air flow demand; less than 45 Pa for rooms with high air flow demand; less than 55 Pa for rooms with very high air flow demand.

As a consequence of the high surface of the terminal element that interfaces with the room to be treated, if the multifunction apparatus is of the vertical extension type, it was observed through laboratory tests that above a certain height it is necessary to divide the plenum into horizontal portions, by means of partitioning walls or diaphragms, and the introduction of specific expedients adapted to regulate/vary the distribution of the air conditioning between the internal portions.

The partitioning walls or diaphragms can also be provided with openings, or they may themselves consist of porous, perforated or otherwise structured materials adapted to allow a controlled passage of air between the various portions of the plenum.

A variant of the above-mentioned vertical multifunction apparatuses may be made by separating the upper portion of the apparatus from the main vertical body and positioning it horizontally at a higher height. Such a portion therefore constitutes a separate plenum, fed by an air duct derived from the main duct that also feeds the vertical apparatus, and includes systems for regulating/varying the air conditioning flow between such a horizontal portion and the portions in the vertical body.

In the horizontal embodiments with a length greater than 2 metres, to regulate the internal distribution of the conditioned air as a function of the temperature and/or the supply flow rate for the subsequent homogeneous exit of the air at low speed towards the rooms to be treated while maintaining the characteristics of low pressure loss, therefore low static operating pressure, as well as correct operation even with the variation of the temperature and air flow rate, it is essential to adopt partitioning walls and/or dividing diaphragms and systems for the optimised dynamic distribution of the air upstream of the terminal elements, which can comprise a movable deflecting fin, arranged on the inlet opening, to deflect part of the supply air towards the upper or lower portions of the plenum.

Furthermore, when both vertical and horizontal types of multifunction apparatuses coexist in the same room, the present invention includes further expedients to optimally distribute the conditioned air between the aforesaid apparatuses, this operation also takes place as a function of the temperature of the conditioned air and/or the temperature difference between the conditioned air that feeds them and the room.

In some cases there is also a regulation of the air intake from the room, sucking it from the lower and/or upper part of the room depending on how the air conditioning is distributed between the vertical and horizontal apparatuses.

The aforesaid expedients and regulation/variation measures of the air distribution for air conditioning, together with other particular characteristics of the multifunction apparatuses, allow to obtain an efficient and effective air conditioning with ventilation/air change, in all the conditions and seasons of operation.

6.2) Constituent Elements of the Embodiments.

As can be seen from the figures and corresponding reports related to the embodiments described in the following chapters, the multifunction apparatus 1, according to the present invention, which essentially forms the part of the air conditioning system closest to the room to be treated, essentially comprises: a plenum 3, end parts of one or more air supply ducts 2, which in some cases has or have a manifold shape, said one or more air supply ducts 2 feed through one or more inlet openings 5, 22 of the supply air in the plenum 3.

The plenum 3 of the multifunction apparatus is divided by partitioning walls or diaphragms 6, 53 that form horizontal portions 7 of predetermined height, the partitioning walls or diaphragms 6, 53 can also be provided with openings 203 for the controlled passage of air between the various portions 7 of the plenum 3.

When there are vertical and horizontal multifunction apparatuses 1 in the same room, systems are included for regulating and/or varying the distribution of air, between the vertical and horizontal apparatuses.

The multifunction apparatus 1 can also have dampers, and/or orifices, and/or perforated calibration sheets 204 to obtain the correct distribution of air.

The air distribution regulation and/or variation systems can comprise dampers, and/or baffles, and/or blades, and/or fins 8, 12, 15a, 15B, 23, 34, 50, 231 which can be regulated as a function of the temperature of the conditioned air feeding them and optionally of the temperature difference between the conditioned air feeding them and the room temperature.

The multifunction apparatus 1 has at least one terminal element 4, which forms the interface part of the multifunction apparatus 1 towards the room to be treated and allows the exit of the conditioned air outlet and the heat exchanges towards the room; moreover, the multifunction apparatus 1 can comprise automation devices of the air distribution regulation and/or variation systems.

The air distribution regulation and/or variation systems listed above, included in the multifunction apparatus 1, can be positioned, according to the versions, in various positions with respect to the apparatus 1 itself, inside and/or outside the apparatus 1.

In particular, the air distribution regulation and/or variation systems can be located upstream of the air inlet opening (s) 5 in the plenum 3, or at, or downstream of, the air inlet opening(s) 5 in the plenum 3; or in/between the supply ducts 2, or inside the plenum 3.

Furthermore, the air distribution regulation and/or variation systems listed above can be in one or more of the above-mentioned positions.

The regulation of the aforesaid air distribution systems can be carried out automatically by means of thermoregulation devices of various kinds, with two-position or modulating action, such as with bimetallic actuators, liquid or wax expansion, or with electronic thermoregulation systems.

The plenum 3 is a space that is located behind or near the terminal element 4, serves for the circulation of air towards the terminal element itself and forms a resonance chamber for a sound-absorbing system that is intended to be formed together with the above-mentioned terminal element; such a space, in addition to being incorporated into specifically constructed multifunction apparatuses, such as those specified in some embodiments, can also consist of, for example, a casing, a technical compartment, the space above a false ceiling, an aeraulic ducting portion, as well as similar elements; at least a portion of a face of the plenum consists of, or is associated with, a terminal element 4.

A particular feature of the multifunction apparatuses referred to in the present invention derives from the properties of its terminal element 4, from which the air exits towards the room. All the types of multifunction apparatuses 1 referred to in the present invention have been designed as a whole to allow the efficient use of a wide range of types of terminal elements 4, making it possible by virtue of the air distribution regulation/variation systems, which are equipped with particular configurations and positions of the air inlet openings 5, 22 in the plenum 3, the overall shapes of the plenum 3 with the related internal portions 7 and partitioning walls or diaphragms 6, as well as other characteristics of the various possible embodiments, described in detail below in the relevant chapters and illustrated in the relative reference figures.

The particular general shape of the multifunction apparatuses referred to in the present invention allows the effective and efficient use of large surface terminal elements 4 characterised by low pressure drops, without compromising the correct distribution of air in all operating conditions and seasons.

The multifunction apparatuses as a whole are structured so as to require static supply air pressures lower than those usually necessary for the known air conditioning systems, of the type equipped with high induction diffusers used to limit the layering of the air in the room, or of the type equipped with the apparatuses referred to in U.S. Pat. No. 6,602, 129B1 reported in chapter 3), state of the art and problems to be solved, or also of the type equipped with displacement diffusers for cooling with high ventilation efficiency. The result is a reduction in the possible leaks of air along the aeraulic ducts upstream of the multifunction apparatuses, reduced noise and a reduction in the electrical consumption of the fans of the air handling unit, as well as the possibility of using FCU type air handling units, that is, fan coils, which have fans with a lower head compared to the centralised AHU type air handling units. In fact, fan coils are provided with fans with a lower static pressure head with respect to AHUs. Some multifunction apparatuses, described in the relative chapter of the examples, are specifically designed to be powered directly by fan coils. Such apparatuses can be used as a variant in the already known plant systems that use fan coils that introduce high-speed air directly into the room. This possibility will allow to significantly improve the comfort of the rooms, modifying the characteristics of heat exchange with the room and the occupants, affecting the average radiant temperature of the surfaces, eliminating annoying air currents, reducing the residual noise of the fan coils and improving the acoustic qualities of the affected room, thanks to the characteristic, also sound absorbing of the multifunction apparatus.

By being able to choose from a wide range of multifunction apparatuses 1, studied and tested by means of prototypes already made and tested, which allow the use of a wide range of types of terminal elements 4, it is possible to create systems specifically suitable for a wide range of applications in the most diverse sectors of the tertiary sector and civil use.

An important feature of the multifunction apparatuses referred to in the present invention is that by virtue of their shape and the large surface area and type of terminal elements 4 that can be adopted, considerably large surface heat exchanges occur with the room, also with a radiant component. Said heat exchanges in part already occur inside the plenum 3 and on the surface of the terminal element 4 facing the plenum, continue along the thickness of the terminal element 4, as well as in adhesion and in the immediate vicinity of its outer surface facing the room, even before the air for the air conditioning distances from the outer surface of the terminal element 4 itself.

This means that: during cooling, since the heat exchange described above has already occurred, absorbing part of the heat from the room, the surface temperature of the terminal element 4 and the temperature of the air for air conditioning that moves away from its external surface, are already considerably less cold than the conditioned air that initially entered the multifunction apparatus; in fact, it has been verified during laboratory tests that said temperatures assume an intermediate value between the temperature of the air conditioning entering the multifunction apparatus and the temperature of the room.

This prevents, together with the low speed and the correct distribution of the air exiting the terminal element 4, any possible disturbance to the occupants, even in its immediate vicinity, also prevents any possible formation of condensation on the surface of the terminal element itself, all this also possibly with air conditioning entering the multifunction apparatuses at a very low temperature, even up to 12-13° C.

The risk of condensation is further avoided by the fact that the air has already been dehumidified by the air handling unit before being conveyed to the multifunction apparatus; during heating, the heat exchange previously described having already occurred, yielding part of the heat from the room, the surface temperature of the terminal element 4 and the temperature of the air for air conditioning that distances from its external surface, are already considerably less hot than the conditioned air that initially entered the multifunction apparatus, as verified during laboratory tests; tests with which it was also found, in average operating conditions, that the air exiting the terminal element already 10-20 centimetres away from its external surface is on average only 2-3° C. warmer than the room temperature, thus avoiding harmful thermal stratifications.

A system thus conceived manages to heat a room at 20° C., without the use of hydronic radiant panels, but with the same feeling of uniformity of the average radiant temperature of the surfaces of the room and without harmful thermal stratifications, using air entering the multifunction apparatus even if only lukewarm, normally about 30° C. in the conditions of maximum heating demand, which thanks to the anticipatory properties of the heat exchange already exposed when exiting the room, already a few centimetres away from the surface of the terminal element has already assumed a temperature of about 25° C.

During normal operation, the inlet temperature is always below 30° C., on average around 25° C., to assume temperatures around 23° C. even a few centimetres away from the surface of the terminal element.

In cooling, the system is inherently even more efficient.

Such characteristics make it particularly suitable for the efficient use of cooling cycle/heat pump generation systems assisted by the use of photovoltaic panels, allowing the systems built also to be included in the context of high energy efficiency systems of the "LTH—HTC" type, an acronym for low temperature heating—high temperature cooling, i.e., characterised by a small difference in temperature (more or less) with respect to the temperature of the room to be treated, maximising its energy classification. In addition, the elimination of hydronic radiant panels, which normally use a large amount of plastic coils embedded in structures that also make them difficult to recycle, as well as the adoption of terminal elements made of natural and recyclable materials, makes the system ecologically advantageous.

In cooling and heating, the surface temperature of the terminal element 4 is in any case respectively cooler and slightly warmer than the room temperature, therefore, thanks also to the large surfaces of the terminal element 4, the well-being of the occupants is also ensured by a radiant effect, which also exchanges heat by radiation with the other surfaces of the room making the average radiant temperature of the surfaces of the room more favourable and more uniform for the comfort of the occupants, combined with the other functions typically performed by the air systems, such as the thermo-hygrometric control of the air, controlled mechanical ventilation, etc., but without the risk of annoying air currents.

The particular shape of the multifunction apparatuses and the consequent large surface area and type of terminal elements 4 that can be adopted make the system effective and efficient both as regards air conditioning and as regards the acoustics of the interior rooms. This is because the multifunction apparatus also makes it possible to adopt terminal elements 4, which in addition to being suitable from the point of view of aeraulic characteristics, are also equipped with high sound-absorbing properties, assisted by the resonance chamber formed by the plenum 3 behind, suitable for the specific type of room. The multifunction apparatus together with its own terminal element 4 is characterised by particular acoustic attenuation qualities also in relation to any noise coming from the aeraulic system placed upstream. The aforesaid acoustic characteristics, together with the very low intrinsic noise of the air diffusers due to the absence of swirling movements and high air speeds, make the air conditioning systems that use the systems referred to in the present invention particularly silent and almost noise-free.

Nowadays, to meet the acoustic needs of indoor rooms, specific sound absorption panels with large surfaces are increasingly used, often also used for contemporary aesthetic-representative functions, with landscape designs, etc.

The use of large-surface terminal elements 4 for the introduction of the conditioned air, characterised by simultaneous sound-absorbing properties, allows to obtain considerable technical and economic advantages. In fact, it is evident that the installation of additional panels for the sole improvement of the acoustic characteristics of indoor rooms would have disadvantages, due to the higher total purchase cost, the increase in installation times and costs, as well as the difficulty and complication of having to look for sufficient free surfaces in the room for the application of the aforesaid acoustic panels in addition to those already present for the air conditioning system. The total quantity of the panels would be given by the sum of the two types of panels, which would also require the use of technicians and installers of different specialisations.

As already in use for the known sound-absorbing panels, the terminal element 4 can also be equipped with drawings, decorations, colours, depict landscapes, etc.

Depending on the needs of the rooms to be air-conditioned, multifunction apparatuses can be chosen equipped with terminal elements 4 equipped with adequate characteristics from the air-conditioning point of view and also from the acoustic point of view.

Under the air conditioning aspect, terminal elements equipped with a perforated external surface can be selected, with a different inductive effect depending on the types, from significant to reduced, up to almost absent, or other types of terminal elements with a porous external surface, without an inductive effect of the air introduced into the room.

With regard to this latter type, in certain versions of the present invention the air can be introduced into the room at such a low speed that it can be assimilated to a transpiration. In this case the system will behave even more similar to a radiant panel system, with apparatuses having the radiant surfaces of the terminal element heated or cooled with the air that passes through it to then be transpired into the room.

Some suitable types of terminal elements 4 equipped with both air conditioning and sound-absorbing characteristics can be, for example, sandwich panels with a honeycomb structure according to Italian patent application no. 102020000029258 and international patent application no. PCT/IB2021/061032, on behalf of the same Applicant, equipped with perforated façades specifically designed also for the passage of air for air conditioning, configurable also in versions with low pressure drops and characterised by a self-supporting structure of a large format of low weight, or the Celenit A mineralised wood wool panels, or the similar product Knauf AMF Heradesign®, possibly further externally covered with an ornamental non-woven fabric, permeable to air, serving as a functional sound-absorbing and aesthetic aid. Both of the above types are easily recyclable, thus preferable.

In addition to the examples above, the terminal element 4 can have various configurations and be constructed with different methods and materials, depending on the type of problems to be solved and/or the different functional needs to be met.

The variables at stake can be, for example, the degree of air permeability and/or the resistance placed on its passage, the volume of interstitial air, the mass, the thermal inertia, the thickness, the sound-absorbing and/or sound-insulating power, the type of surface finish, etc.

The terminal element 4 can also be made starting from panels or blocks already existing on the market, adapted and/or modified and/or completed as necessary, such as, for example, panels and/or elements in wool, and/or fibre: of wood, and/or hemp, and/or vegetable, and/or mineral, and/or plastic materials, pressed and/or mineralised, mineralised and/or treated with resins; panels and/or elements in modified porous concrete, panels with honeycomb (or similar) internal structure with perforated and/or porous specific outer external skins, etc.

The aforesaid elements can also be coupled to each other or with other materials such as mats, felts, fabrics, non-woven fabrics; they can have differentiated stratigraphy and/or progressive porosity along the thickness.

The terminal element in some versions can also be of a type suitable for hanging sheets/notes by means of pins, suitable for hanging pictures by means of nails, or perforated for the application of dowels.

The visible surface that transfers air into the room can be made in different ways, depending on the aesthetic/acoustic/functional results to be achieved, and can therefore be, for example:

plastered with a specific plaster permeable to air, such as the acoustic ones produced by the company BASWA;

made using material similar to the rest of the element, but with a different degree of porosity;

have a coating such as fabric, non-woven fabric, and the like, applied fixedly, semi-fixedly or removably (replaceable or washable), as necessary.

Depending on the version, the terminal element 4 can also have thermal inertia characteristics, due to the specific weight and thickness of the materials used, useful in some applications, especially for systems operating in a heat pump. Other versions can be transparent to light, while maintaining the characteristic of being permeable to the passage of air, to allow the multifunction apparatuses that are equipped with them to also be able to illuminate the rooms.

The multifunction apparatuses referred to in the present invention, in an extension of their application, allow to effectively sanitise and/or disinfect the conditioned air of the indoor rooms served.

The multifunction apparatuses are particularly suitable to be integrated with UVC ray systems (wavelength 254 nm), since the relative lamps are easily placed inside the plenum 3 and the air speed inside the plenum itself, very low, is such as to allow a time of exposure to UVC rays, of the air in transit, effective for the reduction of harmful organisms, viruses and bacteria, with limited electrical powers, absorbed by the lamps.

Such an application can be further integrated to obtain air sanitisation processes of the PCO type, an acronym for photocatalytic oxidation, through the use of surfaces treated with titanium dioxide activated by exposure to UVC rays emitted by the lamps. The UVC lamps (wavelength 220-300 nm) radiate the surface treated with paints containing Titanium Dioxide ($TiO2$): this synergy causes a strong ionisation of the moisture contained in the air, creating and releasing highly reactive and oxidising molecules ($H2O2$ and OH—) that attack microorganisms (germs, bacteria and viruses), destroying their DNA and breaking down other molecules and harmful pollutants, degrading them and eliminating them. All the multifunction apparatuses are equipped with plenums and wide surface terminal elements, both of which can be treated with titanium dioxide paints.

A further integration of the above sanitisation systems is feasible within the multifunction apparatuses, with the addition of UVV lamps (wavelength 185 nm) for the production of ozone, suitable for the disinfection of surfaces and rooms during periods when people are not present.

The above UVV lamps (185 nm wavelength) for ozone production can also be used as an alternative to UVC lamp systems and treated surfaces.

Another alternative, equally feasible, is to equip the interior of the multifunction apparatuses with so-called ionising devices, consisting of polarising electrodes that generate an electric field that produces (emission) positive or negative ions from the air molecules present (plasma) which, by binding to the airborne particles present, make them aggregate (cluster) together and once a sufficient mass is reached, precipitate or adhere electrostatically to the surfaces having opposite or neutral charge.

The air conditioning systems equipped with multifunction apparatuses provided with the aforesaid sanitation systems, supplying the air conditioning through large surfaces that affect the entire room, are able to ensure a level of healthiness of the treated rooms that is considerably higher than that of other known air conditioning systems. Such an application has also been reported in the following example, related to a clothing store.

6.3) Application Example Related to a Clothing Store.

With reference to FIGS. 1A (sectional diagram) and 1B (plan diagram), in which an embodiment of the present invention applied to a clothing store is illustrated, the system comprises an air handling unit (AHU) equipped with an air change system with heat recovery from the expelled air, as well as air cooling with external air when the latter is cooler than the room, i.e., so-called free cooling.

The aforesaid air handling unit is not part of the present invention and will therefore not be described further.

The air exiting the handling unit is conveyed, through aeraulic ducts, to the multifunction apparatuses, which are part of the present invention, which in the specific case are of various types, each explained in the description of the examples in the following chapters. In this case, the apparatuses 1A belong to the vertical type depicted in FIGS. 11, 14, 15, 16, 19, 20; the apparatuses 1B of a vertical type depicted in FIGS. 33, 36, 37, 38, 41, 42; the apparatuses 1C concern a horizontal type depicted in FIGS. 77 to 80. The aforesaid multifunction apparatuses are provided with air distribution systems and particular expedients, described in detail in the examples of the following chapters, which in all seasons of operation, substantially allow:

the optimal distribution of the supply air, both therein and on the surface of the terminal element, and in the room, as the temperature of the air conditioning and the room change, to compensate for the natural tendency of hot air to rise upwards and cold air to fall downwards. For vertical versions, the more the air feeding them being hot with respect to the temperature of the relative room, the more the air is moved into the lower part of the terminal element, vice versa the cooler the air is, the more it is moved towards the upper part of the terminal element. In horizontal versions, the hotter the supply air is with respect to the temperature of the relative room, the more it is corrected for its advancement in horizontal length, since hot air tends to float during its advancement along the plenum and therefore to exit more at the end of the terminal element, vice versa the cooler the air is the more it tends to fall early and to exit more in the initial part of the terminal element, therefore the expedients adopted are used to continue the flow of the exiting air towards the room for the entire length of the terminal element; the particular shape and the set of measures adopted therefore makes the multifunction apparatuses, both vertical and horizontal, suitable to be used for cooling and heating;

significant heat exchanges with the room, with a large surface area and also with a radiant component, which partly occur already inside the plenum and the terminal element and continue in adhesion and in the immediate vicinity of its surface, even before moving away from the outer surface of the terminal element itself;

the total absence of air currents that are annoying for the occupants;

extremely quiet operation;

a static pressure of the supply air significantly lower than usually necessary for the known air conditioning systems, of the type equipped with high induction diffusers used to limit the stratification of the air in the room, or of the type equipped with the apparatuses referred to in U.S. Pat. No. 6,602,129B1 reported in chapter 3), state of the art and problems to be solved, or also of the type equipped with displacement diffusers for cooling with high ventilation efficiency, therefore a reduction of the possible losses of air along the aeraulic ducts upstream of the multifunction apparatuses, a reduced electrical consumption of the fan of the air handling unit, as well as the possibility of also using air handling units of the FCU type, i.e., fan coil, which have fans with a lower head compared to the centralised AHU type air handling units.

The apparatuses 1A are equipped with the various expedients described later in the relative chapter that allow the dynamic adaptation of the operation as a function of the difference in temperature of the supply air with respect to the room temperature. In this case, they have a useful dimension of three metres in width, 2 metres in height and 18 centimetres in depth. The vertical air supply ducts 2 also act simultaneously as structural uprights for the multifunction apparatus itself and reach up to the height of the false ceiling from which the supplies coming from the air handling unit arrive, while the façades of the terminal elements 4A from which the air exits towards the room reach up to 2 metres in height. The apparatuses 1A adopted are of the double-faced type, i.e., with both faces 4A active for the exit of air in the room. In this case, sound-absorbing multifunction panels 4A, of the sandwich type with an internal honeycomb core have been adopted, according to Italian patent application no. 102020000029258 and international patent application no. PCT/IB2021/061032, and can also be configured in versions with low pressure losses and characterised by a self-supporting structure of large size, of low weight, made entirely of aluminium, easily disassembled, therefore totally easily recyclable. The maximum air flow rate required for air conditioning the part of the room served by each face of the terminal element 4A, with dimensions of 3 metres by 2 metres, is 300 m³/hour. The result is a specific flow rate of 50 m³/hour for each m² of surface from which the air exits into the room, with a consequent frontal velocity, at the maximum air flow that can occur, of about 0.014 m/s, as well as less than 0.01 m/s with the necessary air flows during the average operation at full speed. Such speeds are almost inadvertent even in the immediate vicinity of the terminal element 4A, therefore they cannot cause any disturbance to people, especially since, as already mentioned, thanks to the characteristics of the multifunction apparatus there are considerable thermal exchanges with the room, with a large surface and with a component also radiant, partly already inside the plenum and the terminal element and which continue in adhesion and in the immediate vicinity of its surface, therefore, for example during air conditioning in cooling, the conditioned air has already performed a part of its cooling and is therefore already less cold, even before moving away from the external surface, i.e., facing the room, of the terminal element itself; all this has been widely verified with practical laboratory tests on the various prototypes made.

The faces identified with the number 201 are further covered with an ornamental non-woven fabric, permeable to air, acting as a functional sound-absorbing aid and as a representative aesthetic element.

Also the apparatuses 1B, which have been positioned at the boxes, are also equipped with specific expedients described later in the relative chapter, which allow the dynamic adaptation of the operation as a function of the difference in temperature of the supply air with respect to the room temperature. They are also of the double-faced type, but have smaller sizes. They have a useful size of two metres in width, 1 metre in height and 14 centimetres in depth. Also in this case, the vertical air supply ducts 2 also act simultaneously as structural uprights for the multifunction apparatus itself and reach up to the height of the false ceiling from which the supplies coming from the air handling unit arrive, while the terminal elements 4B from which the air exits towards the room reach up to 1 metre in height, above which there are is glass provided with pass-through openings, to protect the operators from contamination.

In this case, given the limited sizes, as terminal elements 4B, sound-absorbing panels in 25 mm thick Celenit mineralised wood wool were adopted, easily recyclable, also further coated externally with an ornamental non-woven fabric, permeable to air, acting as a functional sound-absorbing aid and as a representative aesthetic element. In this case, the maximum air flow rate necessary for air conditioning the portion of the room served by each terminal element face 4B, with dimensions of 2 metres by 1 metre, is 80 m³/hour.

The result is a specific flow rate of 40 m³/hour for each m² of surface from which the air exits the room, with a consequent frontal velocity, at the maximum air flow that can occur, of about 0.01 m/s, as well as less than 0.007 m/s under average operating conditions at full speed. Such speeds are absolutely inadvertent even in the immediate vicinity of the terminal element 4B, also in this case there are thermal exchanges with the room, also with a radiant component that, for example during cooling air conditioning, make the air conditioning even less cold before it moves away from the external surface of the terminal element itself;

The apparatuses 1C of horizontal type shown in FIGS. 77 to 80, were positioned on the ceiling. They are also equipped with their own specific expedients, described later in the relative chapter, which allow the dynamic adaptation of the operation as a function of the difference in temperature of the supply air with respect to the room temperature.

Those positioned in the two central areas of the store each consist of three multifunction apparatuses 1C side by side, 5 metres by 1.2 metres each, for a total of 5 by 3.6 metres. Each multifunction apparatus 1C is provided with its own air supply 2 and relative calibration damper 8.

Also in this case, given the dimensions, as terminal elements 4C, sound-absorbing multifunction panels have been adopted, according to Italian patent application no.

102020000029258 and international patent application no. PCT/IB2021/061032, already mentioned for the apparatuses 1A, but adopting a type suitable for use in horizontal extension apparatuses, therefore with vertical air flow. The maximum air flow required for air conditioning the part of the room served by the set of terminal elements 4C of the three apparatuses 1C, with a total size of 5 by 3.6 metres, is 900 m³/hour. The result is a specific flow rate of 50 m³/hour for each m² of surface from which the air exits into the room, with a consequent frontal velocity, at the maximum air flow that can be verified, of approximately 0.014 m/s. Such a speed is almost inadvertent at human level even in the areas below the air supply terminal elements and cannot cause any disturbance to people, especially since even in this type of multifunction apparatus there are heat exchanges with the room, with a component that also radiates, for example during air conditioning in cooling, making the air conditioning already less cold even before it moves away from the external surface of the terminal element itself;

Those located in the area in front of the entrance from the outside, characterised by the presence of large windows, consist of two aligned multifunction apparatuses 1C, which extend one to the right and the other to the left with respect to the central arrival of a common air supply. Each apparatus is 5 metres by 1.2 metres in size, for a total of 10 by 1.2 metres.

Also in this case, given the size, as terminal elements 4D sound-absorbing multifunction panels have been adopted, according to Italian patent application no. 102020000029258 and international patent application n. PCT/IB2021/061032, adopting a type suitable for use in horizontal extension apparatuses, therefore with vertical air flow, in a version provided with larger diameter perforation in the part closest to the window. The maximum air flow required for air conditioning the part of the room served by the set of terminal elements 4D of the 2 apparatuses 1C, with a total size of 10 by 1.2 metres, is 1300 m³/hour. The result is a specific flow rate of 108 m³/hour for each m² of surface from which the air exits into the room, with a consequent average frontal velocity, at the maximum air flow that can be verified, of approximately 0.03 m/s. From specific tests carried out on prototypes, it was however found that such a speed, intentionally greater with respect to those of the previous cases, but above all in adherence to the window, does not generate annoying air currents at human height even in the areas near the terminal elements, as it is only noticeable in the vicinity of the external glass wall where people do not stop, also in this type of multifunction apparatus there are thermal exchanges with the room, also with a radiant component that during air conditioning in cooling make the air conditioning even less cold before it moves away from the external surface of the terminal element itself;

In addition to the expedients and automatic air distribution systems inherent in the aforesaid multifunction apparatuses, the system is equipped with additional expedients and specific operating logic, designed to optimise the effectiveness and efficiency of the multifunction apparatuses themselves, in order to resolve the critical issues typical of the air systems already exposed, including the tendency to thermal stratification, which in heating, in addition to determining energy expenditure, would also result in a significant decrease in ventilation efficiency to the detriment of indoor air quality.

The relative main specific logic includes:

Air Delivery:

if there are both vertical and horizontal multifunction apparatuses in the same room and the system operates in heating, the logic increases the air delivery in the lower part of the room, favouring the supply of air entering the vertical multifunction apparatus, simultaneously lowering the air flow entering the horizontal apparatuses placed in the upper part of the room.

The only horizontal multifunction apparatuses to which it is advisable not to reduce the supply air flow during heating are those located near windows or walls characterised by considerable thermal dispersion of the heated room towards the outside thereof, since in these cases the heat exchange, with also radiant component, which in part already occurs inside the terminal element and continues in adhesion and in the immediate vicinity of its external surface, is more marked, so the hot air cools considerably even before moving away from the external surface of the terminal element. Furthermore, the thermal dispersion of the window or cold wall rapidly cools the air exiting the terminal element while moving away from it, compensating for its tendency to thermal stratification.

The more the air supplying the multifunction apparatus is hot with respect to the room to be heated, the more the air flow feeding the vertical apparatuses is increased and that relative to the horizontal apparatuses is decreased. When the temperature feeding the multifunction apparatuses is colder than the room temperature, the air flow is distributed between the vertical and horizontal apparatuses according to the optimal design flow rates for cooling, while when it is neutral with respect to the room temperature, it is distributed in an intermediate manner between the two extremes of maximum cooling and maximum heating needs. The modulation sets of such logic can be moved, as appropriate, to have, for example, a greater distribution of air towards the vertical apparatuses already with neutral air. All this occurs in a modulating manner, proportionate to the temperature difference between the air feeding the multifunction apparatuses and the temperature of the relative room.

Figure 1B:
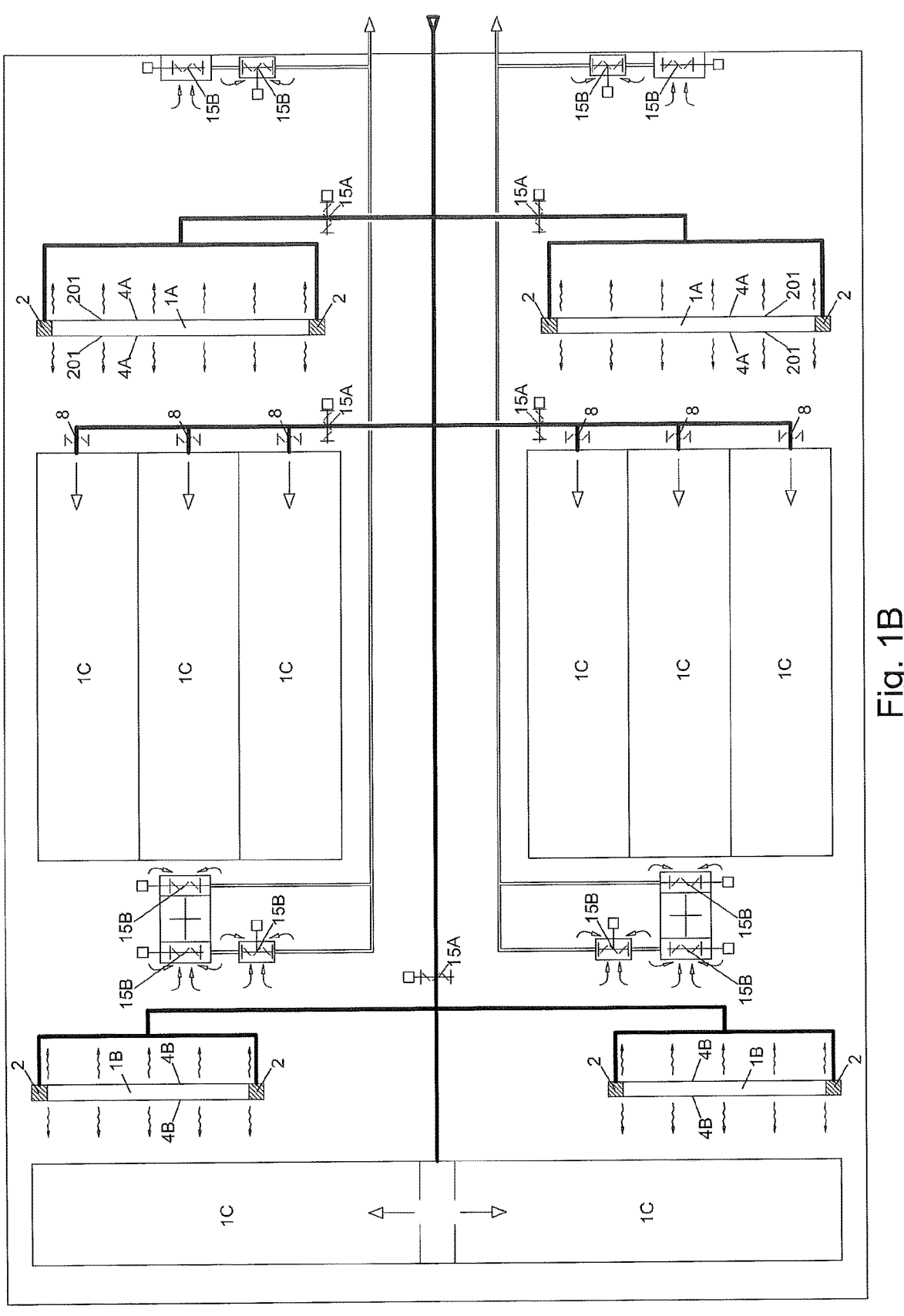

The aforesaid distribution of the supply air flows of the multifunction apparatuses is carried out by the electronic regulation system which acts, according to the logic described, on the motorised dampers identified in FIGS. 1A and 1B with the number 15a.

Air Intake:

The air intakes from the room are positioned both in the upper and lower part of the rooms and are equipped with motorised regulation dampers.

The hotter the air leaving the terminal elements with respect to the temperature of the relative room, the more the air is sucked into the lower part of the rooms and vice versa.

In FIGS. 1A and 1B, the air intakes located in the lower part of the room are identified with the number 38A, while the air intakes located at the top with the number 38B.

The aforesaid distribution of the air flows sucked from the room is carried out by the electronic control system which acts, according to the logic described, on the motorised dampers identified with the number 15B.

Nowadays and increasingly in the future, buildings have a reduced need for heating, while they need rather cooling and the change/healthiness of the indoor air, thus the present invention has sought the development of multiple types of vertical and horizontal multifunction apparatuses to be able to use them in the widest possible range of cases, as they allow a system operation similar to that of the dislocation systems, which are intrinsically characterised by optimal efficiency and effectiveness for cooling and air change, eliminating however the limitations, exalting the advantages and adding further functions not envisaged by the dislocation systems, such as good operation in heating.

The present invention also manages to reconcile the coexistence of horizontal and vertical elements, in order to obtain effective and efficient air conditioning even in local areas where it is not possible or desired to place vertical elements.

The overall structure and operating dynamics of the vertical and/or horizontal multifunction apparatuses and the air intake system from the room, allows a continuous optimisation of the air conditioning of the rooms for the well-being of the occupants and energy efficiency, in any operating condition and at any time of the year.

A system thus conceived manages to heat a room at 20° C., without the use of hydronic radiant panels, but with the same feeling of uniformity of the average radiant temperature of the surfaces of the room and without harmful thermal stratifications, using air entering the multifunction apparatus even if only lukewarm, normally at most 30° C. in the conditions of maximum heating demand, which thanks to the anticipatory properties of the heat exchange, already described, when exiting into the room, already a few centimetres away from the surface of the terminal element, has already assumed a temperature of about 25° C. During normal operation, the inlet temperature is always below 30° C., on average around 25° C., to assume temperatures around 23° C. even a few centimetres away from the surface of the terminal element. In cooling, the system is inherently even more efficient.

Such characteristics make it particularly suitable for the efficient use of cooling cycle/heat pump generation systems assisted by the use of photovoltaic panels, allowing the systems built also to be included in the context of high energy efficiency systems of the "LTH—HTC" type, an acronym for low temperature heating—high temperature cooling, i.e., characterised by a small difference in temperature (more or less) with respect to the temperature of the room to be treated, maximising its energy classification.

In addition, the elimination of hydronic radiant panels, which normally use a large amount of plastic coils embedded in structures that also make them difficult to recycle, as well as the adoption of terminal elements made of natural and recyclable materials, makes the system ecologically advantageous.

All the vertical multifunction apparatuses, 1A and 1B, are further equipped with an internal disinfection system, already described in the chapter on the embodiments of the invention, of the PCO type, i.e., with photocatalytic oxidation, through the use of surfaces treated with titanium dioxide activated by exposure to the rays emitted by UVC lamps at a wavelength of 220-300 nm, with further integration of UVV lamps (wavelength 185 nm) for the production of ozone for the disinfection of surfaces and rooms during periods when people are not present. In this example, the operation of the UVV lamps would be automatically interrupted four hours before the opening of the rooms, with the simultaneous activation of the maximum air renewal, by means of external air input from the air conditioning system, to remove the ozone from the room.

Such technology will allow healthy rooms and a prevention from Covid19 contagion of the rooms and their contents, including clothes, especially since it is also possible to place the clothes in front of the terminal elements, such as for the face 202 of the 4th vertical terminal element referred to in the example. In this case, the exit of sanitising air from the terminal element located in the immediate vicinity of the clothes will have the maximum effect.

The air conditioning systems equipped with multifunction apparatuses equipped with sanitising systems, supplying conditioned air through large surfaces affecting the entire room, are able to ensure levels of healthiness of rooms that are considerably higher with respect to the other known air conditioning systems.

6.4) Application Example Related to a Newly Designed Building.

Figures 90, 91:

This example embodiment is depicted with FIGS. 90 and 91.

In the example of FIG. 90, the operation of the system in maximum cooling, with air supply from above is diagrammed; in the example of FIG. 91, the operation of the system in maximum heating, with air supply from below is diagrammed.

The supply air, coming from the relative handling unit 301, feeds the terminal elements 4 permeable to air placed on the ceiling and on the wall as described below:

the air is introduced into the plenum 3 on the ceiling, which feeds the respective terminal element on the ceiling, and into the plenum 3 on the wall of the respective terminal element 4 on the wall, and is also introduced into the plenum 3 under the floating floor, free of air outlets towards the room, to feed the plenum 3 on the wall and plenum 3 on the ceiling.

About halfway up the plenum 3, a separation partitioning wall 53 is inserted on the wall, which comprises pre-calibrated means for the controlled passage of air.

The surfaces of all the terminal elements 4 exude the air conditioning in the room at such a low speed that it is inadvertent even in the immediate vicinity of their surface and a first combined irradiation/convection heat exchange occurs with the room, before the introduction air moves away from the external surface of the elements 4 themselves.

The introduction air then moves away from the terminal elements 4 and crosses the entire room, air conditioning it properly, as it is sucked in by the adequately located intakes, at the bottom (reference number 38A) and/or at the top in the room (reference number 38B), on the side opposite the air introduction: this allows efficient air conditioning, ventilation/renewal of the air and characterised by maximum comfort conditions. The intakes 38A, 38B are in communication with the intake ducts 39.

The automatic regulation system, for the most advanced solutions controls the dampers 15a and 15B which, in addition to regulating the necessary air flows as a function of the data detected by a room temperature sensor 40, a room relative humidity sensor 41, an indoor air quality sensor 42, distribute the supply air upwards and downwards in the room, as a function of the difference between the supply air temperature detected by the temperature sensor 9 and the room temperature detected by the room temperature sensor 40, all possibly optimised also according to the data detected by optional temperature probes 47 located on the external surfaces of the terminal elements 4.

In maximum cooling, the damper 15A is open and the 15B is closed, the supply therefore occurs from above; conversely, in maximum heating, the damper 15A is closed and the damper 15B is open, the supply therefore occurs from below, thus also heating the floor during its underlying path, before supplying the plenum 3 related to the terminal element 4 placed on the wall. It also controls the regulation of the renewal and free cooling air flow rate, in addition to other quantities normally already controlled by advanced HVAC systems.

Below are a series of examples of various types of multifunction apparatuses 6.5) Multifunction Apparatuses with Vertical Extension.
6.5.1) Versions with Multiple Modulation Dampers Arranged Vertically Along the Supply Ducts.

FIGS. 2 to 10 illustrate some example embodiments of the present invention in which the multifunction apparatus 1 is arranged vertically. The supply aeraulic duct 2 is placed vertically on the side of the plenum 3 of the multifunction apparatus 1 and is provided with horizontal branches 5 that feed it laterally at various heights.

In turn, the supply plenum 3 of the multifunction element 1 is internally divided by means of horizontal partitioning walls 6, which can be airtight, or they can have calibrated passages, consisting of orifices/slots or slits, to keep the various partitions in communication with each other. In the first case, the horizontal partitioning walls 6 divide the plenum into several overlapping plenums 7, each fed by one or more horizontal branches 5 connected to the vertical aeraulic duct 2, not allowing hot air to rise or cold air to fall from one plenum to the other. In the second case, on the other hand, the overlapping plenums 7, each fed by one or more horizontal branches 5 connected to the vertical aeraulic duct 2, allow a passage of air from one plenum to the other, through predetermined orifices/slots, limited by the shape and size of such passages having a predetermined or adjustable section.

The number of horizontal partitioning walls 6 required depends above all on the extension in height and length of the multifunction apparatus 1 and varies if the feed is from one side or from both sides, such a subdivision is also required by the low speed with which the air generally passes in the various components of the multifunction apparatus 1 and in the related terminal element 4.

Therefore, by way of non-limiting example, it can be indicated that for a multifunction apparatus 1 which is 2.4 metres high, 2 metres long, with only one supply side, it is advisable to have a partitioning wall 6 every 40 cm of height; if the same multifunction apparatus 1 were fed from both sides or were only 1.2 metres long instead of 2 metres, it would be sufficient to divide it in height every 60 cm; for lengths greater than 2 metres or for greater dividing heights, supply ducts are suitable from both sides.

Due to the aforementioned low air speed in the ducts, if the air flow is from the top downwards, during the heating step the hot air tends to favour the upper part of the vertical duct and its branches, thus disadvantaging the lower supply branches, while during the cooling step the cold air descends more easily towards the lower part of the vertical duct, disadvantage the upper branches; it occurs conversely if the air flow is from the bottom upwards.

The aforementioned characteristic of the low air speed in the multifunction apparatus 1 in general, causes the inherently low pressure losses of the multifunction apparatus to lose authority with respect to the different natural behaviour of the hot or cold air, due to the relative difference in specific weight or density.

To solve such a problem, the branches 5 serving the upper and lower part of the supply plenum 3 of the multifunction apparatus 1 have been equipped with motorised type dampers 8 possibly controlled by a special thermoregulation device, as a function of the temperature difference between the incoming supply air and the room temperature.

The thermoregulation device then compares the temperature detected by a temperature sensor 9 placed on the aeraulic duct 2, or on the general delivery aeraulic duct if the supply temperature is the same for several multifunction apparatuses in parallel, to determine if the supply air is hotter or colder than the temperature detected by a sensor placed in the room.

Mostly the air is hot with respect to the room, the more the supply ducts 5 of the lower part of the multifunction apparatus 1 open and the more the supply ducts 5 close in the upper part, while with the lowering of the temperature of the supply air with respect to the room air, the air supply in the upper part gradually opens and closes proportionally in the lower part.

The regulation dampers 12 relative to the ducts 5 of intermediate height between those of the upper part and those of the lower part can also be motorised with relative servo controls. In this case, the automation will cause such dampers to assume an intermediate opening position between the opening position of the supply ducts 5 of the upper part and the lower part.

The opening of the supply ducts 5 in the upper part and the corresponding closing of the lower part, or vice versa, as well as the intermediate position of the regulation dampers of the intermediate height ducts 5, can also occur through the use of a single motorisation, therefore through a single servo control, combining the various high, intermediate and low regulation dampers, with opposite action, so that the complete opening of the uppermost position corresponds to an intermediate position of the intermediate height and the complete closing of the lowermost one, as well as vice versa.

The thermoregulation device can also be of the thermostatic type with liquid or wax expansion, with the relative limitations with respect to electronic systems.

The electronic thermoregulation device allows, depending on the relative settings and/or needs, to favour more or less intensely the distribution of air, if hot in the lower part, if cold in the upper part, of the terminal element 4.

The above solution allows an automatic calibration of the air distribution according to the difference between the temperature of the incoming supply air and the room temperature, furthermore, if the control system is of an electronic type, any other parameters, detected by relative probes, may be taken into account to optimise, for example, the quality and/or healthiness of the internal air.

In some cases, temperature sensors 10 can also be added placed in some of the partitions 7; in particular, the sensors 10 can be placed in the highest and the lowest partition. In this case, the automation can also regulate the distribution of air flows to maintain certain homogeneous or deliberately differentiated air temperatures between the top and bottom of the terminal element 4.

As an alternative to the automatic device, the calibration or the operation switching can be regulated manually, but in this case the automatic regulation logic explained above will not be possible.

In detail, FIGS. 2 and 3 illustrate, respectively in front view and in sectional view, a vertical multifunction apparatus 1, of a simpler type because of its height within 1.8 metres and width within 1.2 metres, with the plenum 3 equipped with three partitions 7 with aeraulic supply ducts 2 on one side only. FIG. 4 illustrates a pair of multifunction apparatuses 1, like those of FIGS. 2 and 3, fed by a single aeraulic duct 2, sized so as to sufficiently power the two multifunction apparatuses 1.

In the supply ducts 5 there are dampers 8, 12 to vary the flow of supply air towards the partitions 7 as a function of the temperature difference between the supply air and the room temperature. In some cases, in the central partition 7 the motorisation of the damper 12 can also be absent and the damper can also be replaced by a calibrated orifice.

FIGS. 5 and 6 show, respectively in front view and sectional view, a vertical multifunction apparatus 1, of a more complex type because of its height over 1.8 metres, with the plenum 3 equipped with six partitions 7.

In this version, the air distribution regulation logic in the partitions varying in height can work either in pairs of two partitions, i.e., the two highest partitions will be regulated together, as if they were a single high partition, the two intermediate partitions as if they were a single intermediate partition and the two lowest as if they were a single low partition. Everything will therefore operate like the version in FIG. 2 because in terms of logic it is as if the partitions to be regulated were always three; or the modulation logic can occur on all six dampers. For example, with a logic that with significantly colder supply air than the room, starting from the damper of the highest part and descending towards the underlying down to the lowest, will have the highest open at 100% of its capacity, the damper below at 80%, the one below at 60%, then even lower at 40%, the penultimate at 20%, then the lowest closed; vice versa as the air becomes less cold with respect to the room, modulating it until reaching the inverse condition having supply air hotter than the room, with the lowest damper entirely open and the highest one entirely closed.

FIG. 7 shows a pair of multifunction apparatuses 1, with six partitions 7 of the plenum 3, like the multifunction apparatus 1 of FIGS. 5 and 6; in this case, the two multifunction apparatuses 1 are fed by a single aeraulic duct 2, sized so as to sufficiently feed both multifunction apparatuses 1.

FIGS. 8 and 9 depict another variant of the examples illustrated in FIGS. 2-7. In this variant the air supply for the vertical multifunction apparatus 1 is obtained by means of two aeraulic ducts 2 arranged on both sides of the apparatus.

The two aeraulic ducts 2 then branch into a number of horizontal ducts 5 which send air into the partitions 7, the ducts 5 for the upper and lower partitions are equipped with dampers 8, while the central partitions are provided with dampers 12 with optional motorisation.

The operating principle is the same as the version in FIG. 5.

FIG. 10 illustrates an embodiment example that has two opposite terminal elements 4 with respect to the plenum 3, consisting of two opposite faces 13, 14 capable of emitting air. This configuration can be achieved for all the versions referred to in FIGS. 2 to 8.

Unlike the example of FIG. 9, adapted to be arranged with the side from which the air does not exit even against a wall, the solution depicted in FIG. 10 is adapted to be positioned in the rooms, to create, for example, any separations between one area and the other and/or to effectively air condition even rooms with a relatively large surface area.

6.5.2) Compact Versions with Multiple Modulation Dampers Arranged Vertically Along the Supply Ducts.

The examples of FIGS. 11 to 32 relate to compact versions made according to the basic principles of FIG. 8, i.e., according to the basic principles of FIG. 2 but with air supply from both sides.

For each side, the upper and lower dampers 8, as well as the intermediate ones 12, are of the type with rotating blades with a stroke of 90° and are axially conjugated with each other, controlled by a single servo control 11. The connection timing between one damper and the other is carried out so that when the higher damper is completely open, the lower damper is completely closed and the intermediate damper 12 is half-open. This means that when the higher damper has rotated for half of its stroke, that is 45°, closing by half, the lower damper, also rotating by 45° also, will be brought from closed to half opening, while the intermediate damper 12 rotating by 45°, from the starting position, which was at half opening, will be opened completely. This is to have a preferential air flow in the central part of the terminal element 4 under neutral temperature supply air conditions, with respect to the room temperature. The aforesaid connection timing between one damper and the other is also adjustable according to the needs of the various types of rooms in which the apparatus is used. The conjugation between the dampers can also be obtained carried out by means of levers and returns as an alternative to the axial connection. The damper 12 in some cases may also not be conjugated to the movement of the dampers 8, but be independently calibrated, even fixed. Specifically, FIGS. 11 to 21 refer to versions with air supply coming from above. The supply ducts 2 can simultaneously act as uprights of the load-bearing structure of the apparatus itself. The dividing partitioning walls 6 are provided with longitudinal slots 203 having predetermined section that allow air to pass from one portion of plenum to another, limited by the shape and size of the slot. In the specific case, the tests performed on the prototypes gave the best results with 5 mm slots along the entire length of the dividers 6, but the section is variable on a case-by-case basis depending on the application of the apparatus in the different types of rooms and consequent relative use.

The dampers 12 in some cases can also be absent and replaced with infills closed to the passage of air. In this case, the passage of air towards the central partition of the plenum 3 will only occur through the slots 203.

FIGS. 11 to 20 refer to a version suitable up to a height of 2 metres, in some cases up to 2.2 metres, with a maximum width varying, depending on the type of terminal element 4 adopted, from 3 to 4 metres.

Depending on the width of the apparatus and the type of terminal element 4 adopted, it may be necessary to add perforated calibration sheets 204, in order to evenly distribute the air exiting the terminal element itself.

FIGS. 11 to 15 show the air flows when the supply temperature is hotter than the room temperature. The higher damper is closed, so no air passes, the intermediate damper 12 is open in the middle, the lower damper is entirely open. The hot air entering the lower portion 7 of the plenum 3, once its portion of plenum is fully affected, rises in part towards the portion of plenum above, through the longitudinal slot 203 present in the relative partitioning wall 6;

the same thing occurs between the portion of plenum placed at intermediate height towards the highest portion of plenum, which is not fed in any other way since the relative damper 8 is closed. An important feature of the multifunction apparatuses is that important convection and radiation thermal exchanges occur between the air conditioning and the room through the terminal element 4 already starting from the interior of the plenum, this means that the air rising from one compartment 7 to the upper one is already colder than when it had entered the lower portion of the plenum, therefore even with the same air flow exiting towards the room at the various heights of the terminal element 4, it can have a temperature of the terminal element itself that is basically warmer in its lower part, which is ideal for the heating function. In fact, the higher temperature in the lower part allows a greater heat exchange with the portion of the floor near the terminal element, thus also heating the floor, which is normally very critical with other types of hot air systems.

FIGS. 16 to 20 depict air flows when the supply temperature is cooler than the room.

The highest damper is open, the intermediate damper 12 is open in the middle, the lowest damper is entirely closed, so no air passes. The cold air entering the highest portion 7 of the plenum, once its portion of plenum is fully affected, partly descends towards the portion of plenum below, through the longitudinal slot 203 present in the relative partitioning wall 6; the same occurs between the portion of plenum placed at intermediate height towards the lower portion of plenum, which is not fed in any other way since the relative damper 8 is closed.

Similar to what occurs during heating, even during cooling operation advantages are obtained due to the peculiarity of the controlled air flows, between the various portions in height of the plenums. In this case, the passage of air through the longitudinal slots in the partitioning walls 6 occurs in the opposite direction, i.e., from top to bottom. The cold air conditioning carries out the usual heat exchanges already starting from inside the plenum, therefore, according to the same concept previously described for heating, even with the same distribution of exiting air flows at the various heights of the terminal element 4, the apparatus corrects the tendency of the air to further cool the lower part of the terminal element 4, which would be useless since the floor in this case is basically already colder than the room. This also resolves the fact that during cooling air conditioning, it is also important, for the comfort of the occupants, to avoid cold air flows at the ankles.

In some cases, temperature sensors 10 can also be added placed in some of the partitions 7; in particular, the sensors 10 can be placed in the highest and the lowest partition. In this case, the automation can adjust, both in heating and in cooling, the distribution of air flows also to maintain certain homogeneous or deliberately differentiated air temperatures between the upper and lower part of the terminal element 4.

Figures 11, 12, 13, 14, 15:
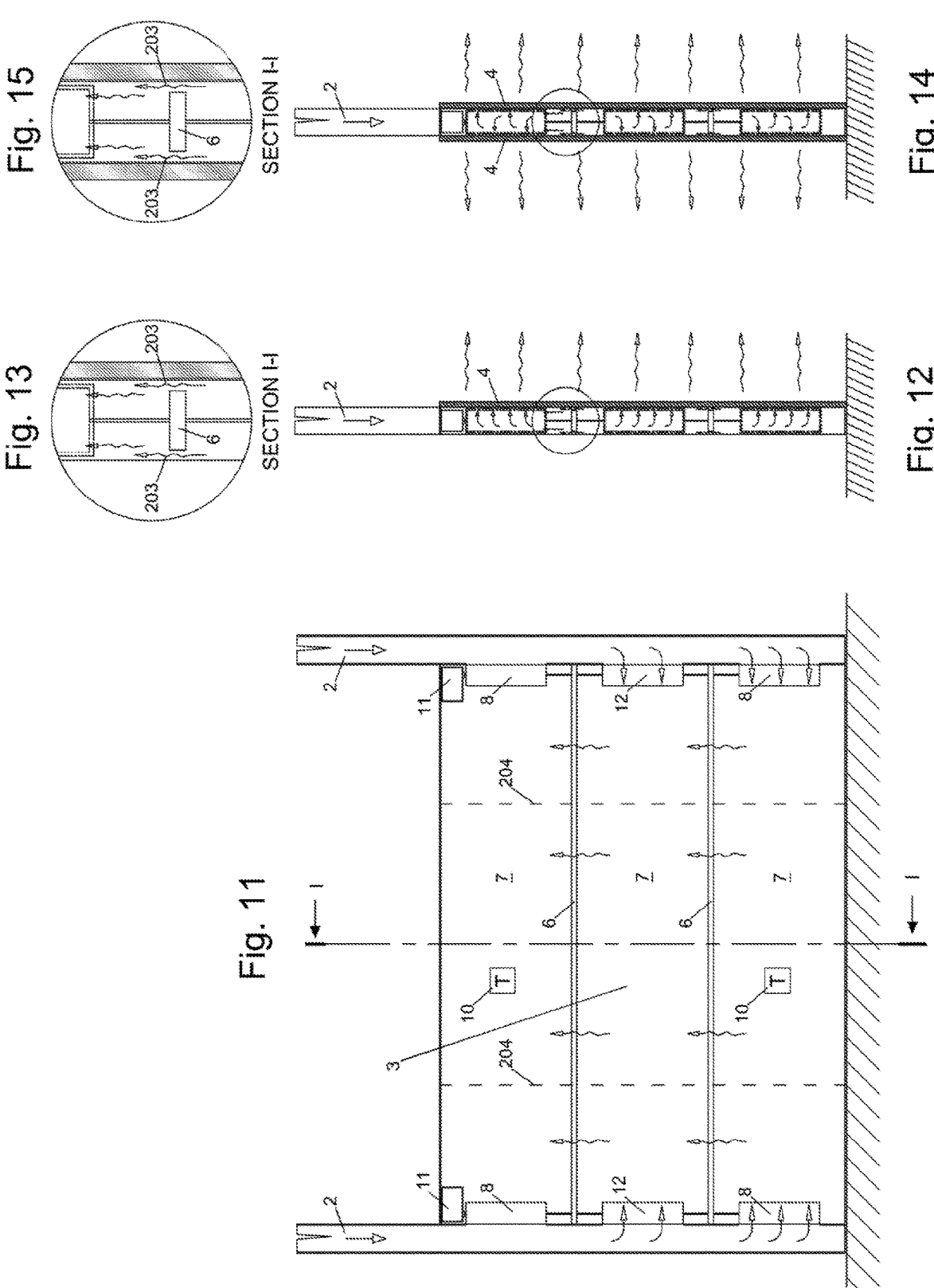

FIGS. 12 and 17 with the relative enlarged details 13 and 18, refer to a so-called single-sided version, i.e., equipped with a terminal element 4 only on one side. The slots 203 can also be present towards the side not provided with a terminal element 4, in the case in which the apparatus is used as a partition between two areas of the room, in which one of the two areas does not have particular needs for air conditioning or air change, for example in the case of internal corridors with the sporadic passage of people. In this case, the slot 203 on the side without the terminal element 4 serves to heat, or cool, the wall closed to the passage of air, which acts as a radiant panel. The slots 203 can also be replaced by calibrated holes made along the partitioning walls 6, but it has been found by testing the various prototypes made that leaving a longitudinal slot, as indicated in the drawings, for the passage of air in adherence to the inner surfaces of the terminal element 4, or the blind wall as in the above case, better efficiencies are obtained.

FIGS. 14 and 19 with the relative enlarged details 15 and 20, relate to a double-sided version, i.e., equipped with terminal elements 4 on both sides.

Figure 21:
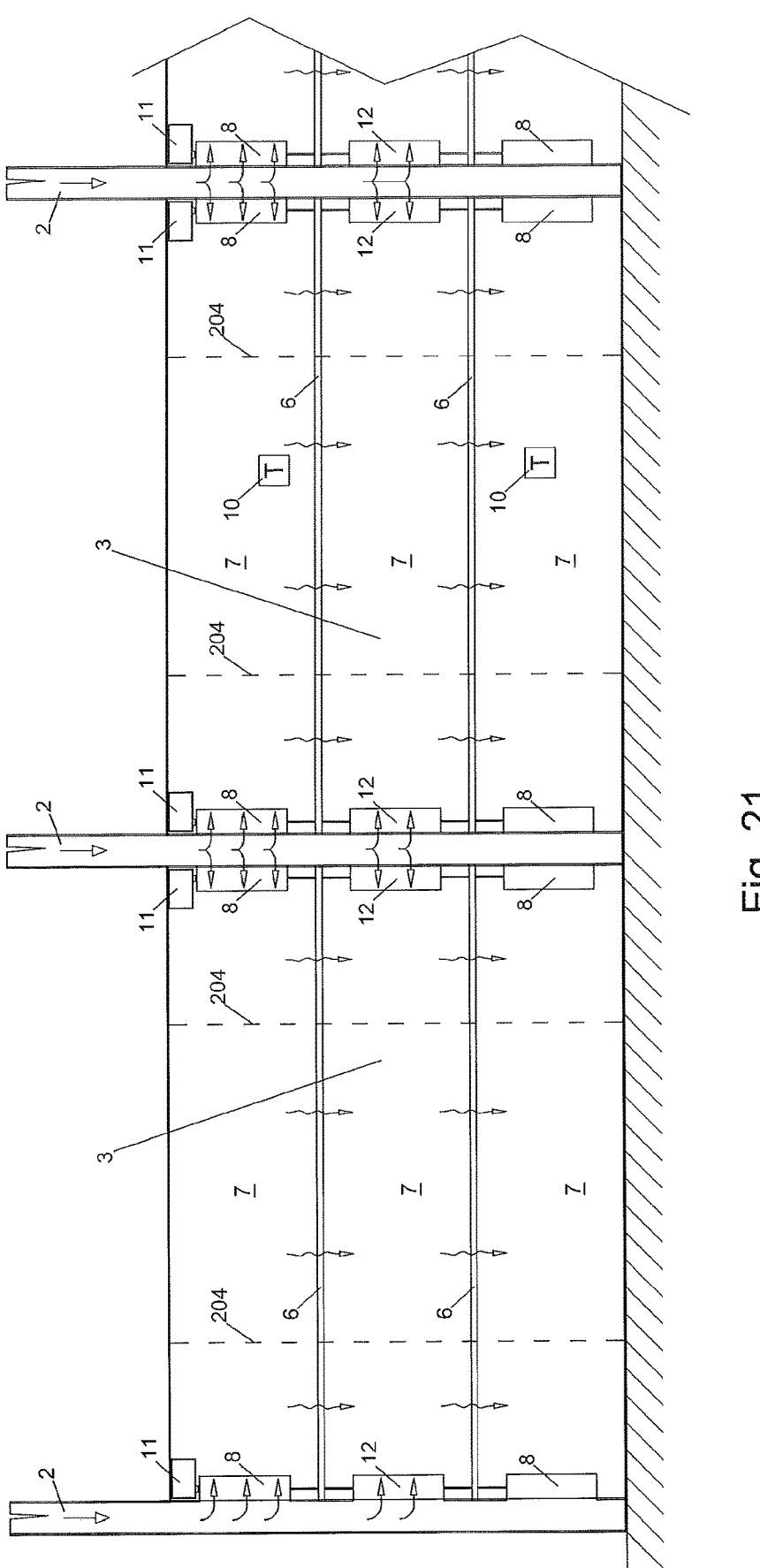
Figures 22, 23, 24, 25, 26:
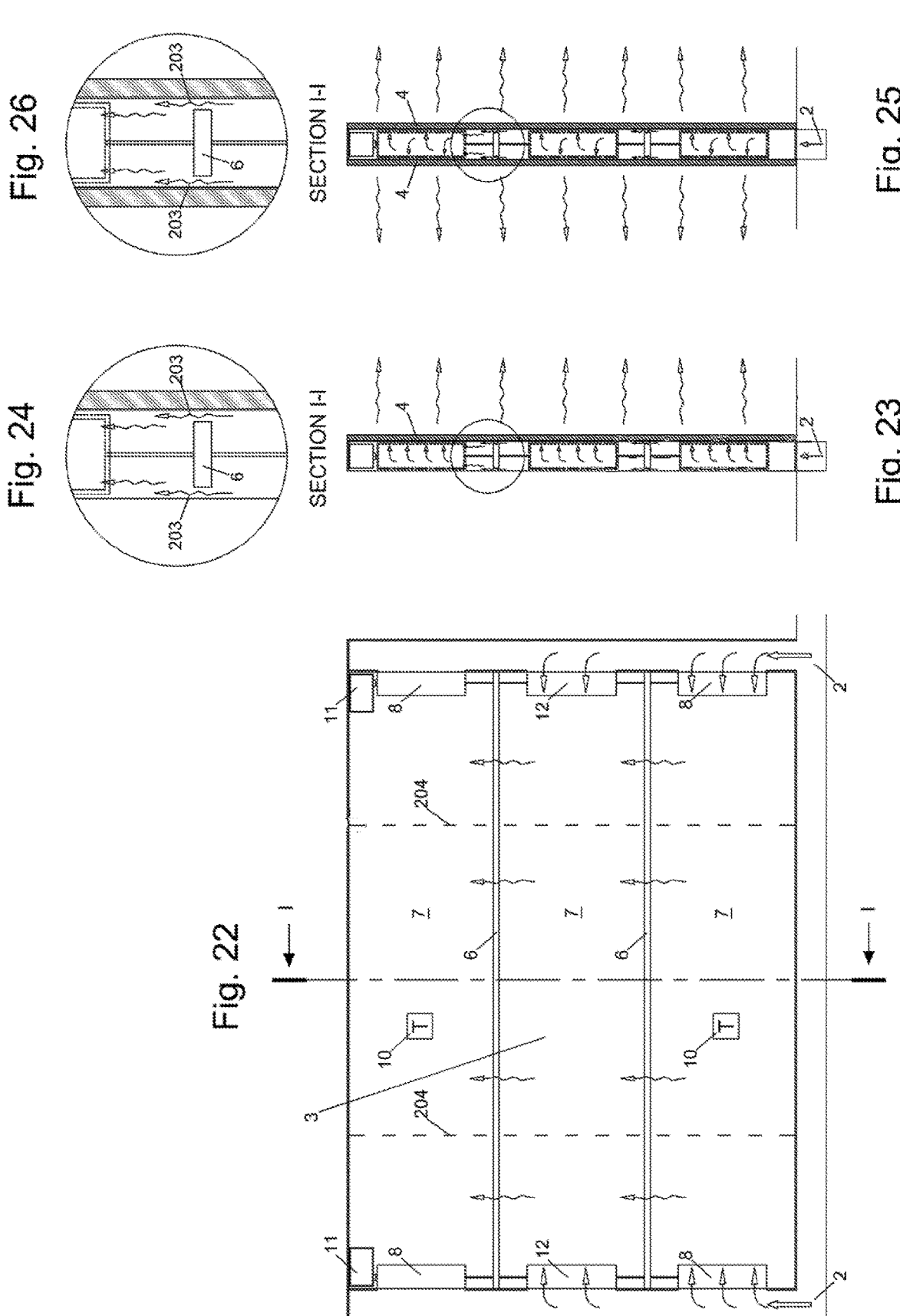
Figure 32:
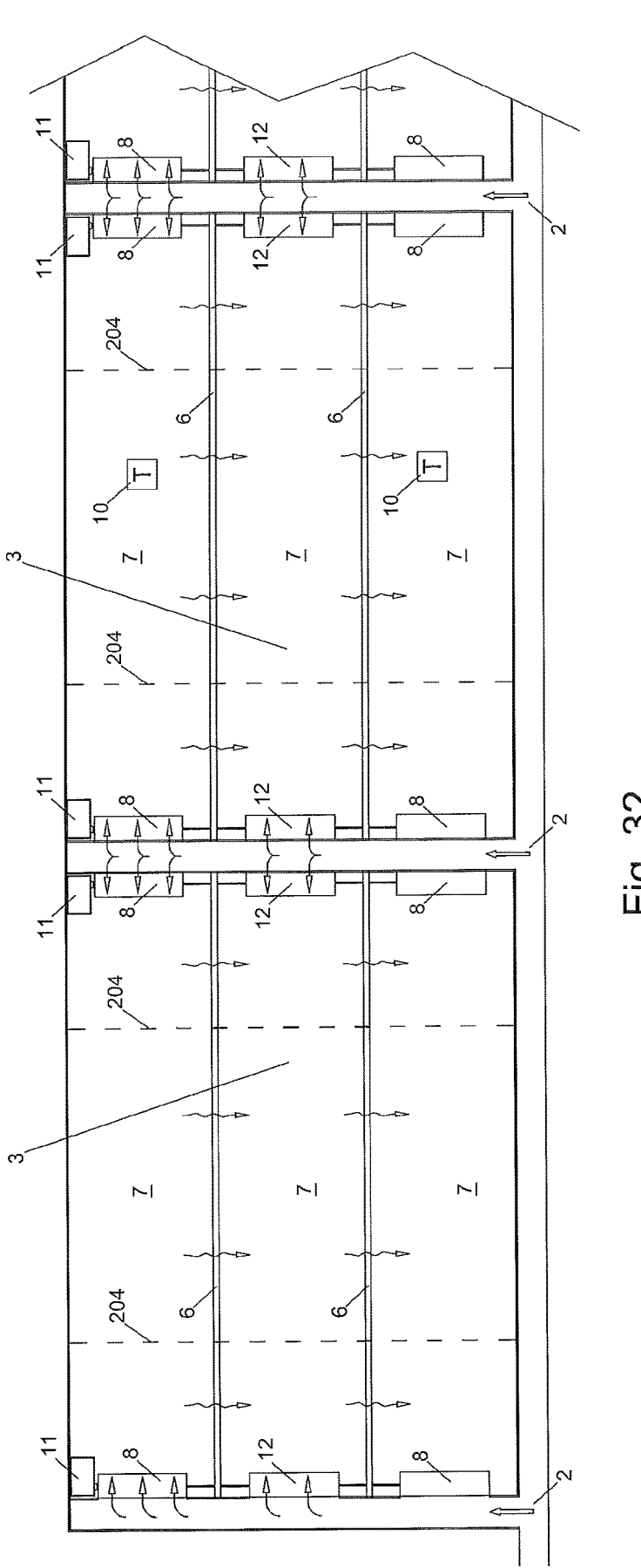

FIG. 21 relates to a version which allows the creation of modular apparatuses in any length.

The apparatus is provided with several supply ducts, the first and the last of which determine the two ends of the apparatus. The supply ducts placed in the middle feed the plenums both to their right and to their left. The example shows the flows in the coldest supply air condition of the room.

FIGS. 22 to 32 relate to versions with air supply from below. The concepts and peculiarities of operation are the same as in FIGS. 11 to 21.

6.5.3) Versions with Modulation Dampers Arranged in the Middle of the Supply Ducts.

In the examples of FIGS. 33-38, similar to the previous solutions of the examples illustrated in FIGS. 2-10, the supply aeraulic duct 2 is placed vertically on the side of the supply plenum 3 of the terminal element 4 and is provided with branches with horizontal supply ducts 5 that supply the terminal element 4 laterally at various heights with the plenum 3 internally divided with horizontal partitioning walls 6.

In this example, to overcome the different behaviour of the air in the heating step with respect to the cooling step, as already explained in detail for the previous examples of FIGS. 2-10, the vertical duct 2 is equipped, approximately halfway up with respect to the supply branches 5, with a motorised damper 15, controlled by a temperature control system as a function of the temperature difference between the air feeding the multifunction apparatuses and the temperature of the relative room.

By keeping the motorised damper 15, arranged on the duct 2, open if the air in the supply duct 2 arrives from above and closed if it arrives from below, each horizontal duct 5 is calibrated through the dampers 8 and 12 to have the proper distribution of air during the heating step, such calibration remains unchanged even during the cooling step.

In this case, the dampers 8 and 12 can be manually regulated, or even be replaced by openings with a predetermined section possibly also equipped with perforated sheets, because they are only used for calibration, while the regulation of the distribution of hot or cold air is carried out through the motorised damper 15.

If in the aeraulic duct 2 placed vertically on the side of the plenum 3 supplying the terminal element 4, the flow is from top to bottom, the hotter the air, the more the motorised damper 15 opens, to favour the air supplying the lower part of the terminal element 4, while with the lowering of the entering air temperature, the damper 15 progressively closes to favour the air supplying the upper part.

It should be considered that the damper 15 opens or closes contrary to what is described above if the flow in the vertical channel is from the bottom upwards.

The thermoregulation device can also be a thermostatic type with liquid or wax expansion.

As an alternative to the automatic device, the calibration or switching operation can be manually adjustable.

In the case of an electronic control device, it is also possible to consider any other parameters detected by relative probes, for example it is possible to detect and consider the quality of the room air.

The electronic regulation device also makes it possible, depending on the relative settings and/or needs, to favour more or less intensively the distribution of hot air in the lower part or cold air in the upper part of the terminal element.

Also for these versions in some cases temperature sensors 10 can be added placed in some of the partitions 7; in particular the sensors 10 can be placed in the highest and the lowest partition. In this case, the automation can also regulate the distribution of air flows to maintain certain homogeneous or deliberately differentiated air temperatures between the top and bottom of the terminal element 4.

Figure 36:
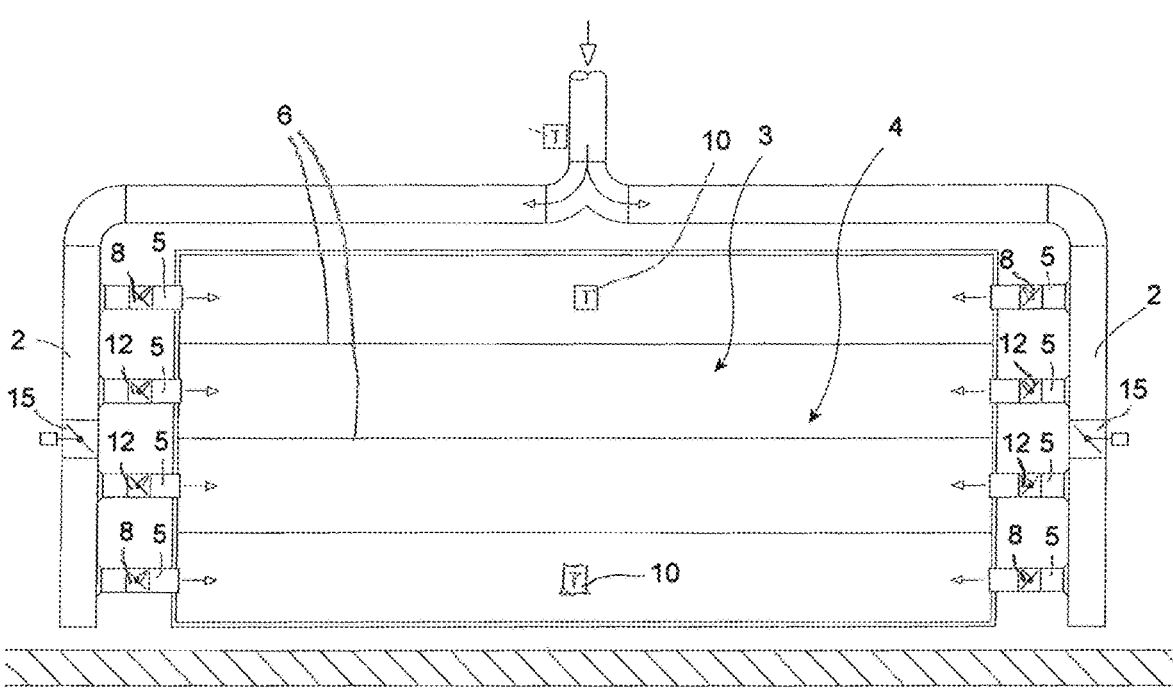

6.5.4) Compact Versions with Modulation Dampers Arranged in the Middle of the Supply Ducts The examples of FIGS. 39 to 60 relate to compact versions made according to the basic principles of FIG. 36, i.e., according to the basic principles of FIG. 33 but with air supply from both sides.

Specifically, FIGS. 39 to 49 relate to versions with air supply coming from above. The supply ducts 2 can simultaneously act as uprights of the load-bearing structure of the apparatus itself.

The plenum 3 is partitioned in height through the partitioning wall 6, which divides it into two portions 7. Such a dividing partitioning wall 6 is provided with a longitudinal slot 203 having a predetermined section that allows a passage of air from one portion of plenum to the other, limited by the shape and size of the slot. In the specific case, the tests performed on the prototypes gave the best results with 5 mm slots along the entire length of the divider 6, but the section is variable on a case-by-case basis depending on the application of the apparatus in the different types of rooms and consequent relative use. Inside each supply duct there is a motorised damper 15, positioned in the centre with respect to the two portions, high and low, of the plenum, such dampers being controlled by a temperature control system as a function of the temperature difference between the supply air and the temperature of the relative room. In the example, the motorisation 11 is in common for both dampers, which move in unison. In some cases, especially when the apparatus is very wide, with dampers consequently very distant from each other, it is advisable to provide each damper with its own servo control.

The inlet of the supply air in the two partitions 7 of the plenum occurs through the openings 5, which appear to have a predetermined section, possibly also equipped with perforated sheets 205, because they are only used for the calibration of the system, while the regulation of the distribution of hot or cold air is carried out through the motorised dampers 15.

FIGS. 39 to 48 refer to a version suitable up to a height of 1.2 metres, in some cases up to 1.4 metres, with a maximum width varying, depending on the type of terminal element 4 adopted, from 3 to 4 metres.

FIGS. 39 to 43 depict air flows when the supply temperature is hotter than the room temperature. The dampers 15 are open, so the air, through the supply openings 5, can enter both portions 7 of the plenum 3.

In some cases, depending on the height of the apparatus, the two openings 5 feeding the upper partition of the plenum require perforated calibration sheets 205, to facilitate the entry of hot air into the lower portion 7 of the plenum.

The hot air entering the lower portion 7 of the plenum 3, once its portion of plenum is fully affected, rises in part towards the portion of plenum above, through the longitudinal slot 203 present in the relative partitioning wall 6;

Given the important feature already described of the heat exchanges between the air conditioning and the room already starting from the interior of the plenum, the air rising from the lower compartment 7 to the upper one is already colder than when it had entered the lower portion, therefore even with the same air flow exiting towards the room at the various heights of the terminal element 4, it can have a temperature of the terminal element itself that is basically warmer in its lower part, which is ideal for the heating function. In fact, the higher temperature in the lower part allows a greater heat exchange with the portion of the floor near the terminal element, thus also heating the floor, which is normally very critical with other types of hot air systems.

FIGS. 44 to 48 depict air flows when the supply temperature is cooler than the room.

The dampers 15 are closed, therefore the air can only enter the upper portion 7 of the plenum 3. The cold air entering the uppermost portion 7 of the plenum 3, once its portion of plenum is fully affected, partly descends towards the portion of plenum below, through the longitudinal slot 203 present in the relative partitioning wall 6. Given the important feature already described of the heat exchanges between the air conditioning and the room already starting from the interior of the plenum, the air descending from the upper compartment 7 to the lower one is already warmer than when it had entered the upper portion, therefore the apparatus corrects the tendency of the air to cool the lower part of the terminal element 4 more, which would be useless since the floor in this case is basically already colder than the room. This also resolves the fact that during cooling air conditioning, it is also important, for the comfort of the occupants, to avoid cold air flows at the ankles.

In some cases, temperature sensors 10 can also be added in the highest and lowest partition. In this case, the automation can regulate, both in heating and in cooling, the distribution of air flows also to maintain certain homogeneous or deliberately differentiated air temperatures between the higher and lower parts of the terminal element 4.

Figures 39, 40, 41, 42, 43:
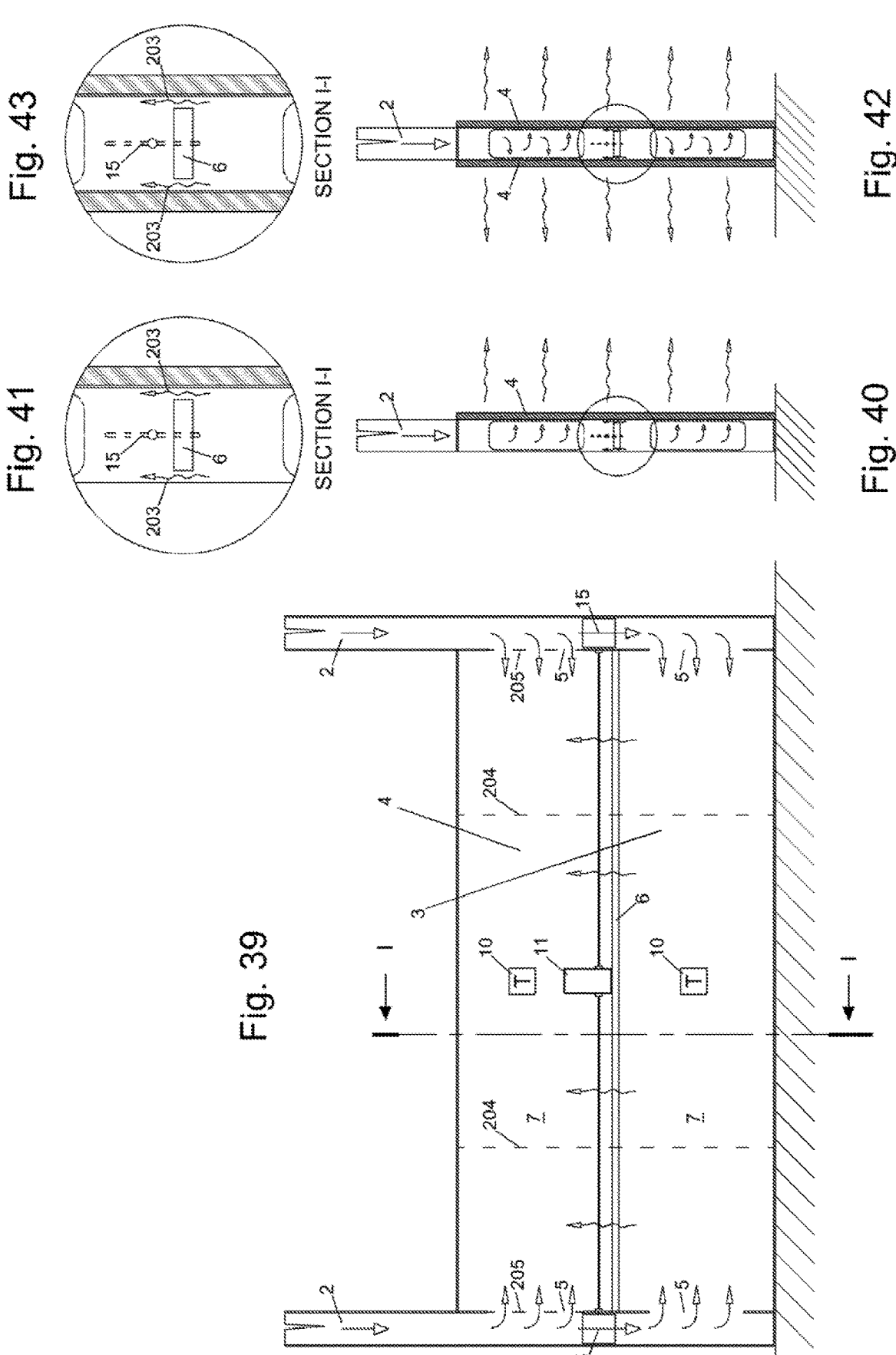

FIGS. 40 and 45 with the relative enlarged details 41 and 46, refer to a so-called single-sided version, i.e., equipped with a terminal element 4 only on one side. The slots 203 can also be present towards the side not provided with a terminal element 4, in the case in which the apparatus is used as a partition between two areas of the room, in which one of the two areas does not have particular needs for air conditioning or air change, for example in the case of internal corridors with the sporadic passage of people. In this case, the slot 203 on the side without the terminal element 4 serves to heat, or cool, the wall closed to the passage of air, which acts as a radiant panel. The slots 203 can also be replaced by calibrated holes made along the partitioning walls 6, but it has been found by testing the various prototypes made that leaving a longitudinal slot, as indicated in the drawings, for the passage of air in adherence to the inner surfaces of the terminal element 4, or the blind wall as in the above case, better efficiencies are obtained.

FIGS. 42 and 47 with the relative enlarged details 43 and 48, relate to a double-sided version, i.e., equipped with terminal elements 4 on both sides.

Figure 49:
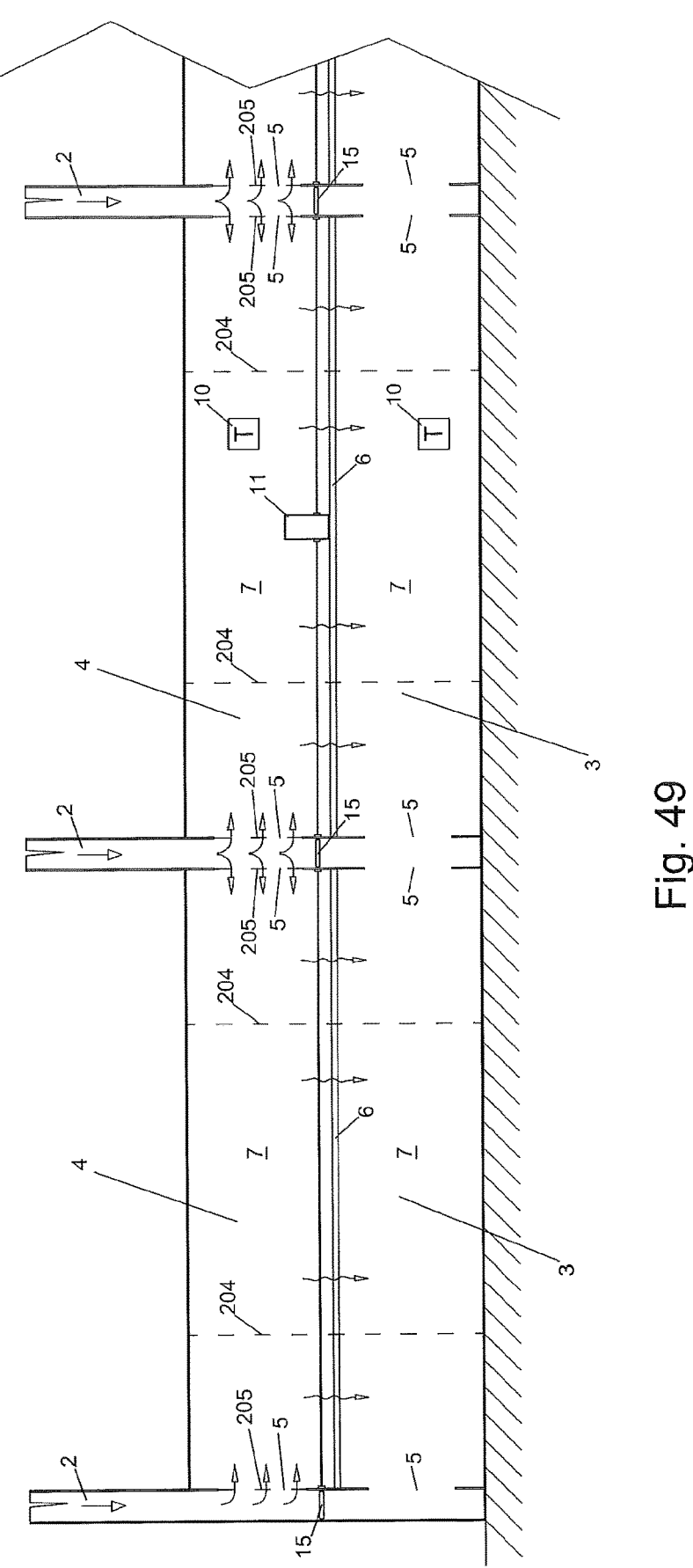
Figures 50, 51, 52, 53, 54:
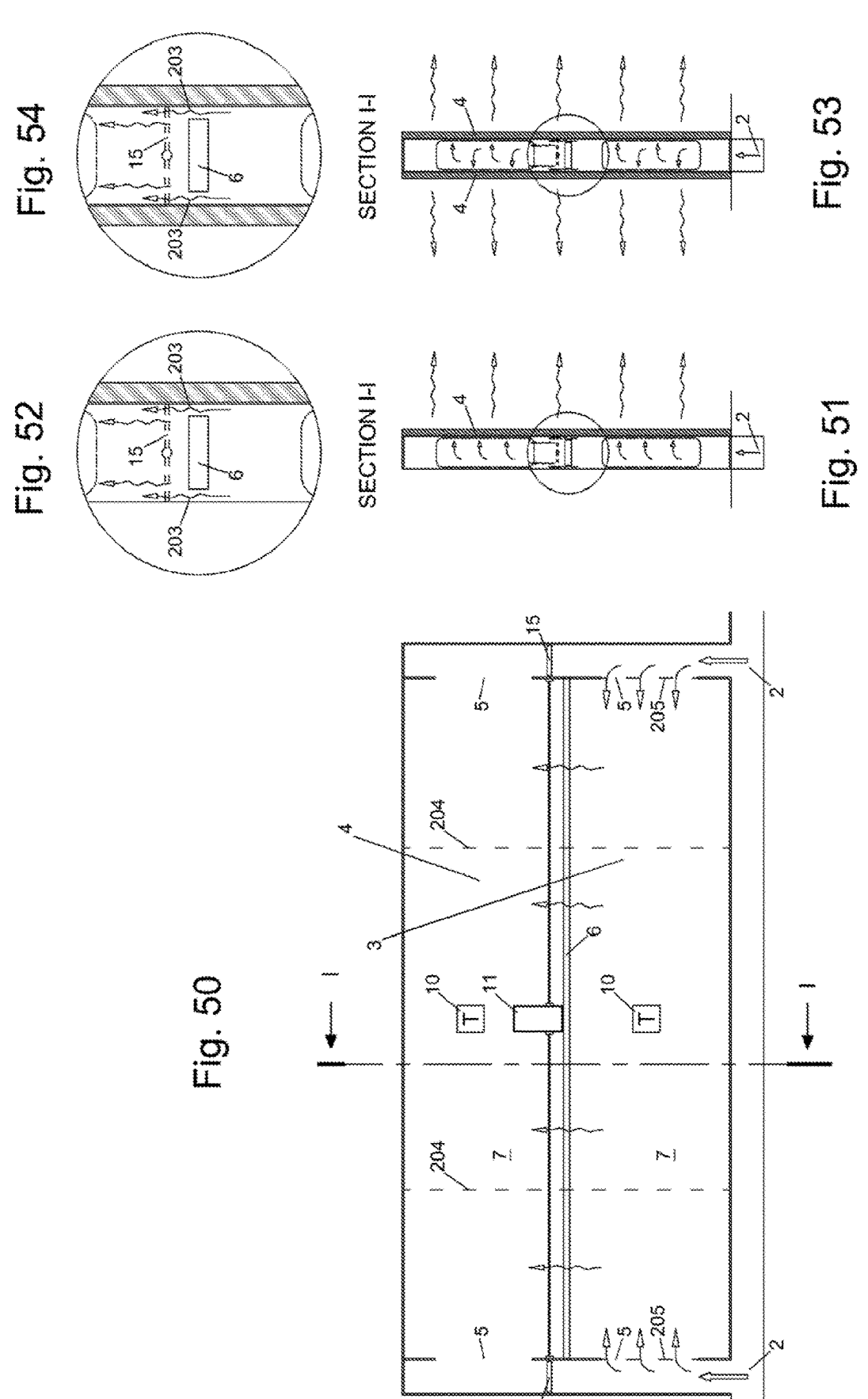
Figures 55, 56, 57, 58, 59:
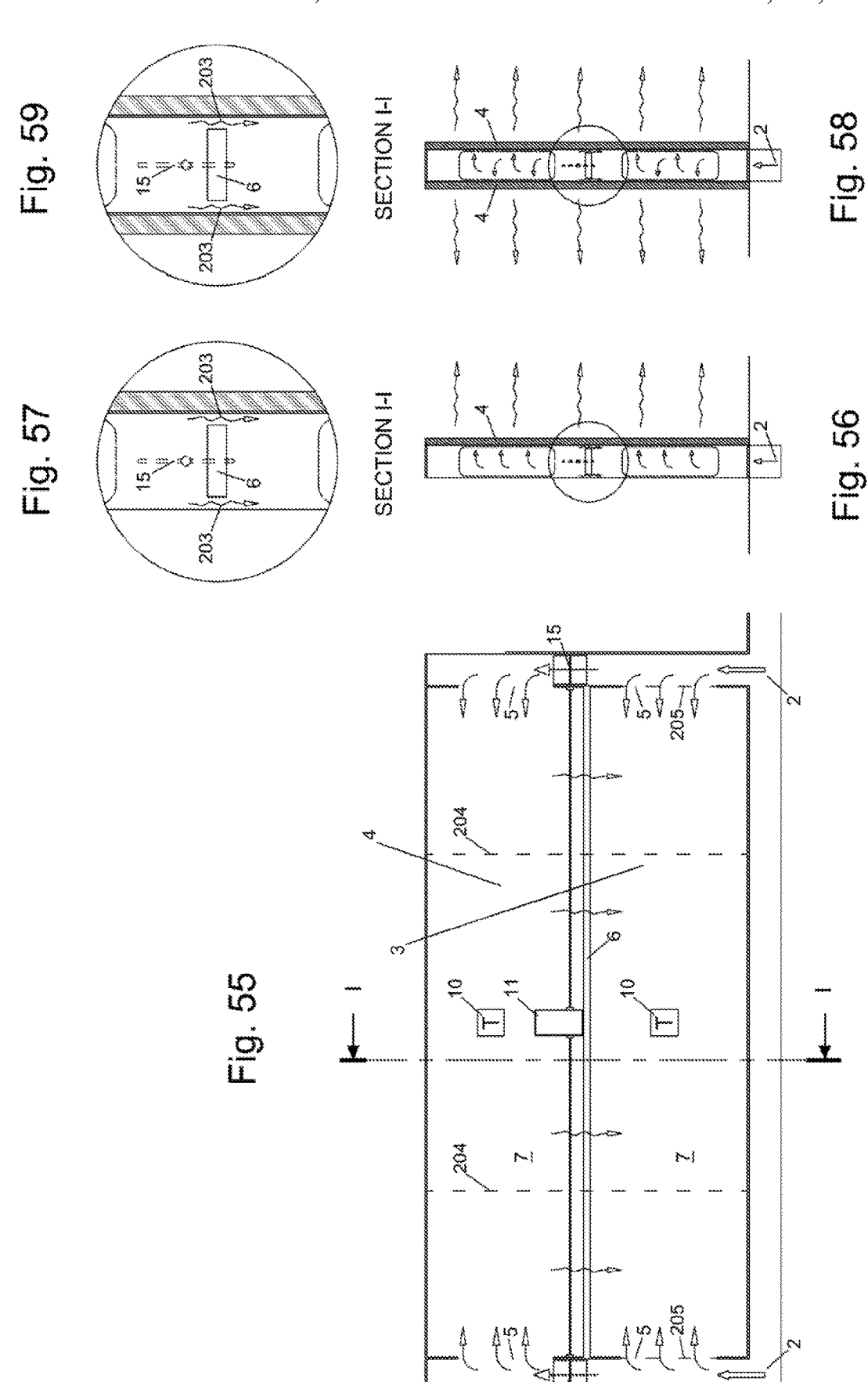
Figure 60:
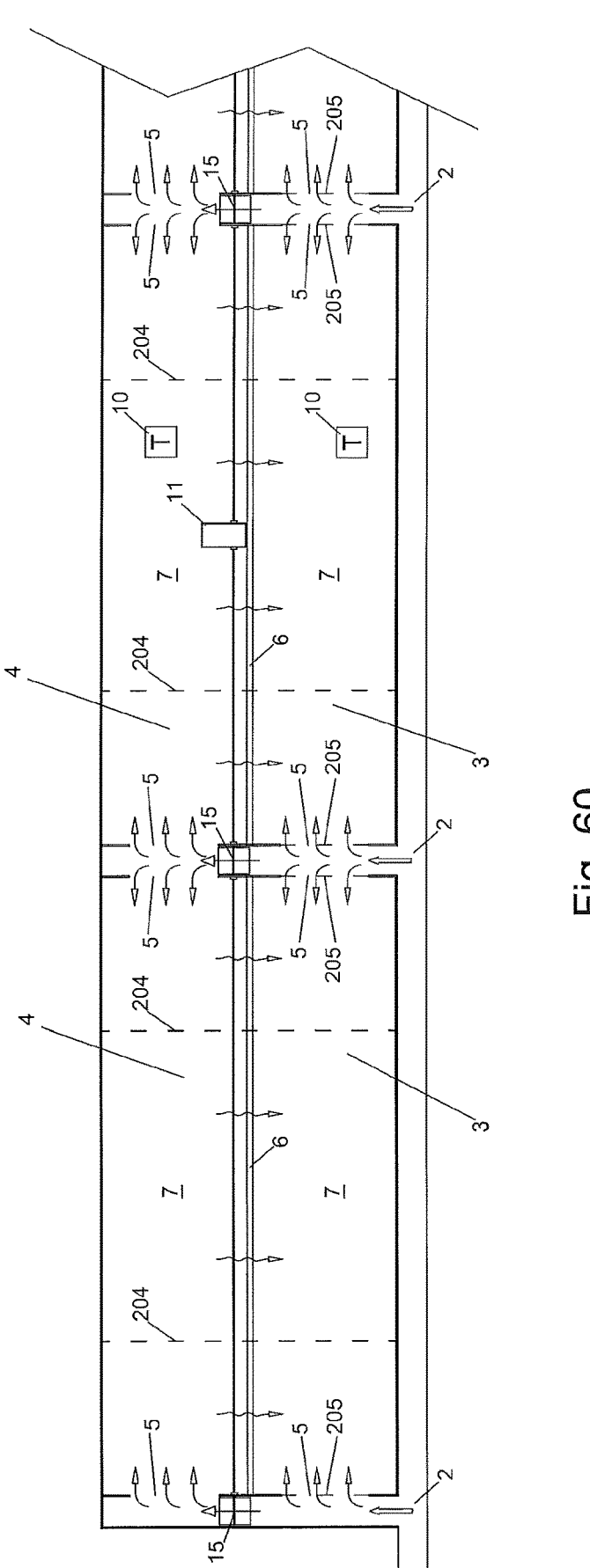

FIG. 49 relates to a version which allows the creation of modular apparatuses in any length.

The apparatus is provided with several supply ducts, the first and the last of which determine the two ends of the apparatus. The supply ducts placed in the middle feed the plenums both to their right and to their left. The example shows the flows in the coldest supply air condition of the room.

FIGS. 50 to 60 relate to versions with air supply from below. The concepts and peculiarities of operation are the same as in FIGS. 39 to 49. The only difference is that in this case any perforated calibration sheets 205 must be positioned on the air inlet openings 5 related to the low portion 7 of the plenum 3 to facilitate the entry of hot air.

6.5.5) Versions with Modulation Damper Arranged Inside the Plenum.

FIGS. 61 to 69 illustrate solutions in which the plenum 3 is divided in height into two portions 7 by a partitioning wall 6, at which there is a longitudinal blade damper 23, with adjustable opening. An aeraulic duct 2 horizontally feeds the low partition 7 of the plenum 3.

This solution is suitable for terminal elements 4 with a height up to about 1.5 metres, with variable length/width depending on the variants described below.

It has been found during laboratory tests on prototypes that, given the low speed adopted in the ducts, if the horizontal duct 2 is placed below the plenum 3 of the multifunction element, feeding in sequence the various air inlet openings placed in the lower part of the plenum 3 through calibrated openings 5 derived from the upper part of the duct 2, as in the example of FIGS. 61 and 62, the hot air in the heating step tends to rise more in the first openings 5, while the cold air in the cooling step tends to progress on the bottom of the horizontal duct, favouring the last openings 5. The calibrations, performed with dampers, or predetermined orifices, 12, are of a fixed type, consequently if performed for operation with hot air they are not good for operation with cold air and vice versa.

Figures 61, 62:
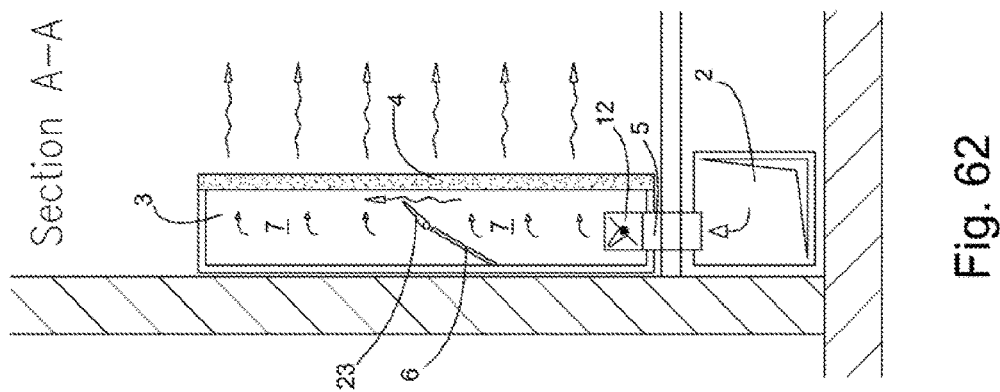
Figure 64:
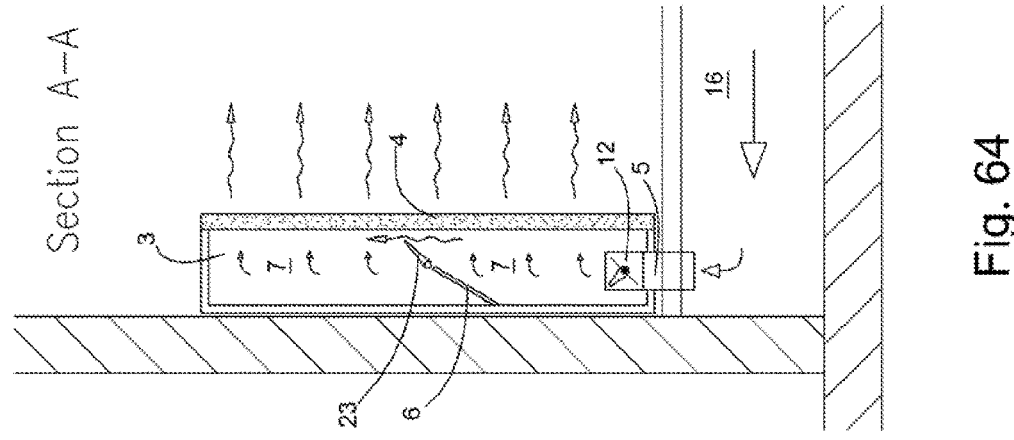

Therefore, in the version depicted in FIGS. 61 and 62, if the supply air reaches the duct 2 only on one side, it is suitable for systems that must only carry out heating, or only cooling, since if the apparatus were supplied indifferently with hot or cold air, the difference in temperature of the supply air would determine an unacceptable change in the distribution of air over the length of the terminal element 4. If both heating and cooling operation is required, air supply is also required from the side 2b of the ductwork. To distribute the entering air uniformly to the plenum through the openings 5, it is appropriate to insert the perforated calibration sheets 204 into the duct 2. The version shown in FIGS. 61 and 62 has reasonable limits of about 3 metres in length if the supply air arrives from one side only, and doubles if it also arrives from the side 2b.

Such limits are also dictated by the overall dimension of the ducting which is sized to serve the supplies 5 arranged in sequence over the length of the apparatus. The longer the apparatus, the higher the air flow rate, thus the more cumbersome the ducting.

Figure 66:
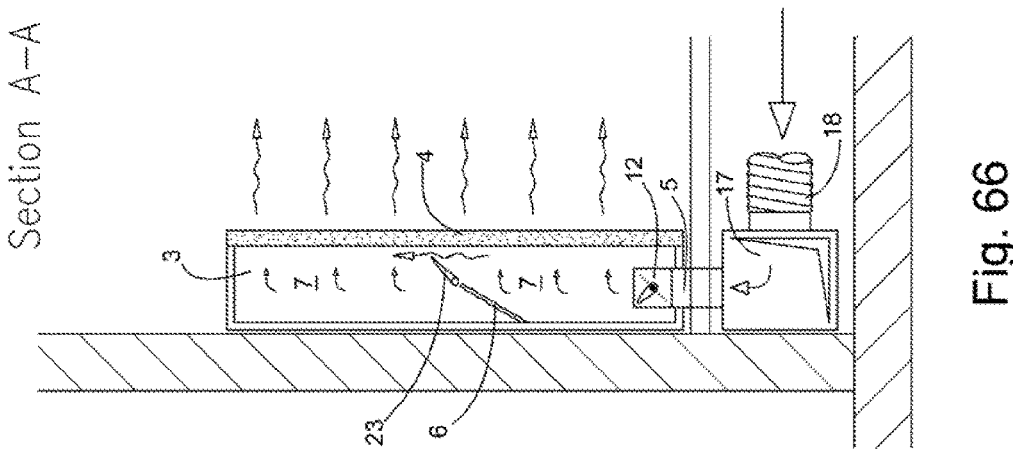
Figure 65:
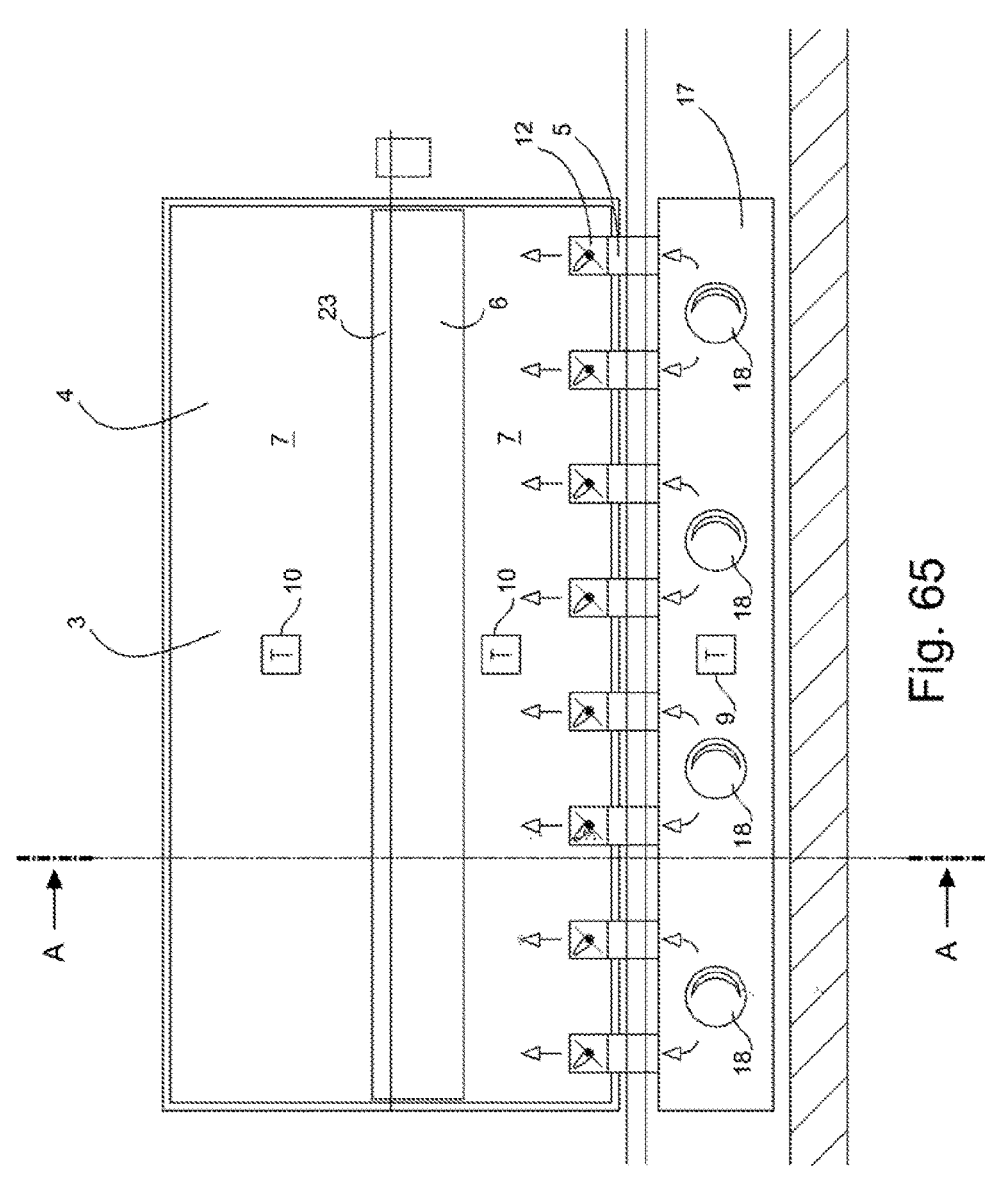

When the apparatus must perform both the heating and cooling functions, an improved solution is to feed all the air inlet openings 5 in the plenum 3 of the apparatus frontally and simultaneously, for example by supplying it directly from a cavity 16 such as a floating floor (for example in FIGS. 63 and 64), or through a manifold duct 17 supplied frontally by various ducts 18 (for example FIGS. 65 and 66). This type of supply, frontal in parallel, allows to create apparatuses without particular length/width constraints.

Figures 67, 68:
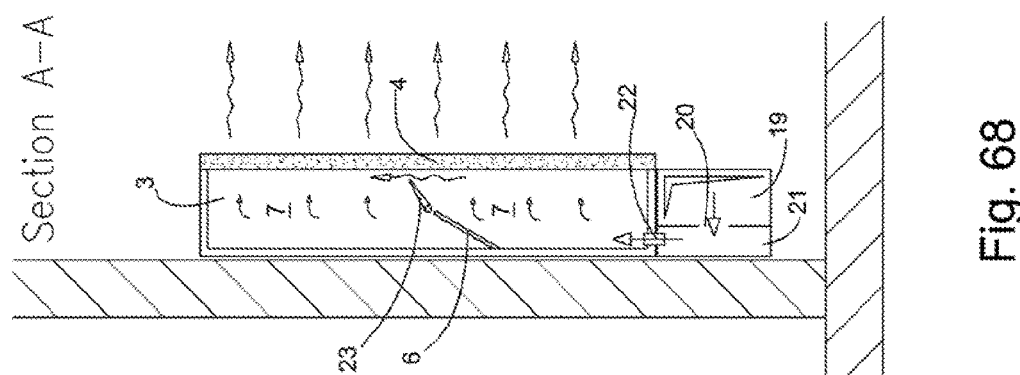

FIGS. 67 and 68 illustrate another embodiment in which the air supply occurs through a horizontal duct 19 arranged laterally below the plenum 3.

The horizontal duct 19 has holes 20 at half its height, which introduce air into another duct 21 behind, in turn provided with openings 22 facing upwards, which feed the lower partition of the plenum 3. To distribute the entering air uniformly to the plenum through the openings 5, it is appropriate to insert the perforated calibration sheets 204 into the duct 2.

The air running through the horizontal duct 19, not having the outlet openings in its upper part, but only the holes 20 at half height, is not affected along its path by the marked change in specific weight depending on the hot or cold operating step. Even this version, if the duct 2 is fed only from one side, is subject to length limits, but only due to the sizing of the supply duct resulting from the sequential arrangement of the openings on the length of the apparatus, therefore it can be up to 4 metres long, doubling if the air also arrives from the side 2b.

For the various solutions referred to in FIGS. 61 to 69 in question, depending on the tasks to be performed by the apparatus, the damper 23 can be fixed calibration, manually variable, or motorised with opening modulated by an automatic regulation system depending on the temperature of the supply air or the temperature difference between the supply air and the room. The hotter the supply air is, the more the damper closes to facilitate the exit of hot air from the lower part of the terminal element 4, compensating for the natural tendency to preferably move to the upper part of the plenum; conversely, as the air becomes colder, the damper 23 opens to allow the cold air to also reach the upper part of the plenum so that it can exit along the entire height of the terminal element 4. The air is introduced into the supply plenum 3 of the terminal element 4, from the bottom, from the openings 5 or 22, with a launch speed such as to allow, with the damper 23 open during the cooling step, the arrival of cold air also in the upper part of the plenum.

The device can also be thermostatic with liquid or wax expansion.

If the regulation device is electronic, the thermoregulation can also take into account any other parameters detected by the relevant probes, for example air quality.

The electronic device also makes it possible, depending on the relative settings and/or needs, to favour more or less intensively the distribution of hot air in the lower part or cold air in the upper part of the terminal element.

In some cases, temperature sensors 10 can also be added in the highest and lowest partition. In this case, the automation can adjust, both in heating and in cooling, the distribution of air flows also to maintain certain homogeneous or deliberately differentiated air temperatures between the upper and lower part of the terminal element 4.

In the case of operation only with hot air, a fixed calibration damper may be sufficient; in this case the damper 23 can be replaced by one or more horizontal partitioning walls (not illustrated) with partial pre-calibrated closure, also by perforating the partitioning walls themselves.

If the system only carries out cooling, the damper 23 or the pre-calibrated partitioning walls can be omitted.

All the versions referred to in FIGS. 61 to 69 can actually have executions (not illustrated), overturned by 180°, i.e., with air supply from the upper part instead of from the lower part. In this case the damper 23 must operate with opposite logic, i.e., the hotter the supply air, the more it must be opened and vice versa. In this case, the air introduced from above into the supply plenum 3 of the terminal element 4 must exit the openings 5 or 22, with a launch speed such as to allow, with the damper 23 open during the heating step, the arrival of hot air even in the lower part of the plenum.

Figure 38:
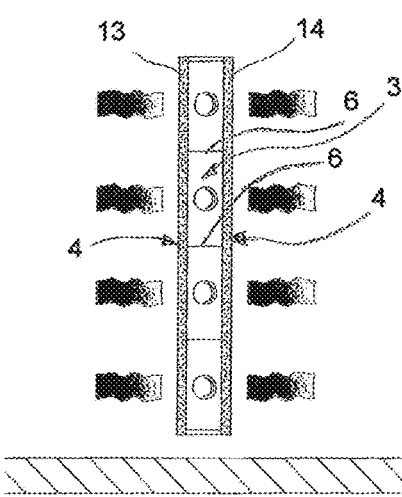
Figure 69:
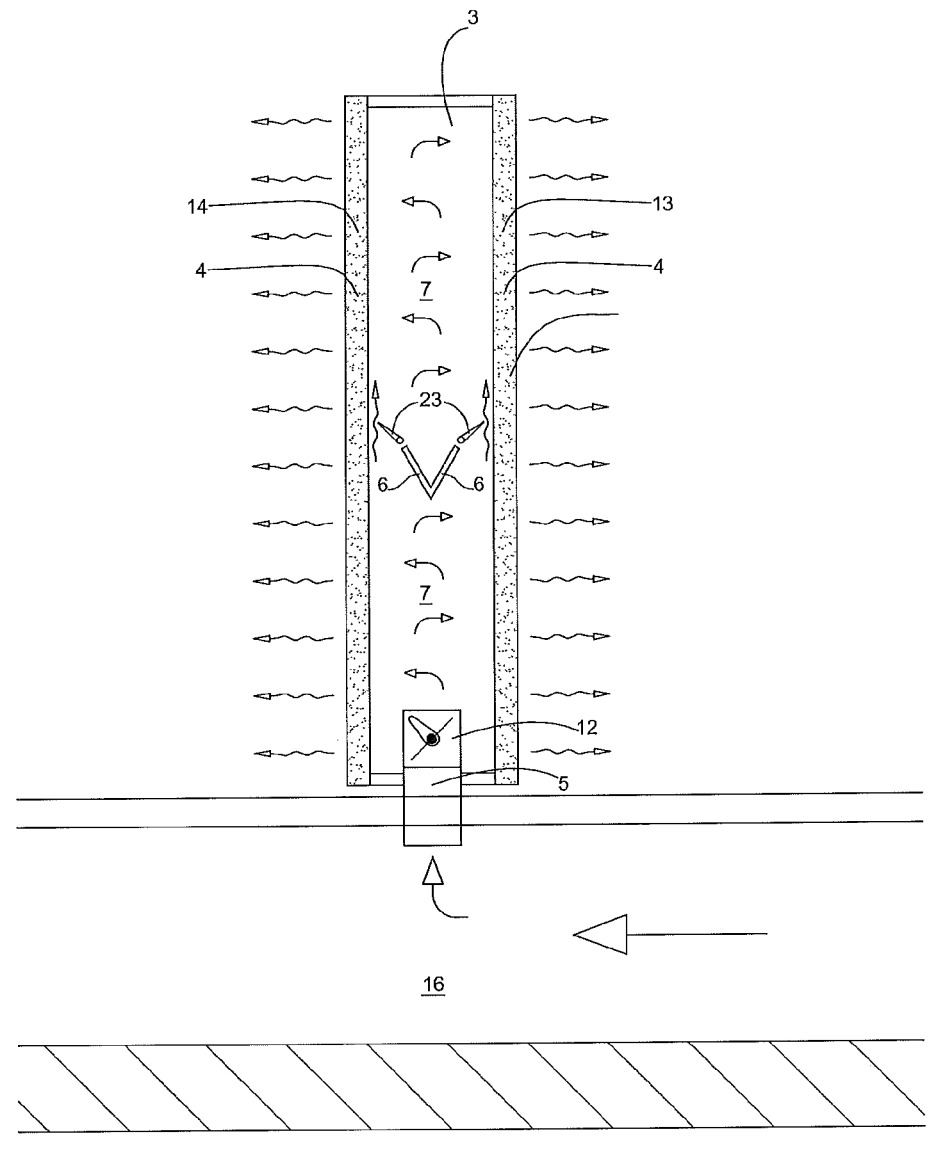

FIG. 69 shows a double-sided version applicable to all the versions of FIGS. 61 to 69, equipped with two opposite terminal elements 4 with respect to the plenum 3, consisting of two opposite faces 13, 14 capable of emitting air, in an entirely similar manner to what is illustrated in FIGS. 10 and 38.

FIGS. 70 to 72 illustrate other examples of apparatuses equipped with terminal elements 4 with a height of up to about 2.2 metres and a width of up to about 5 metres.

Unlike the examples illustrated in FIGS. 61-69 that have terminal elements 4 of lower heights and with air supply only on the lower side or only on the upper side, to obtain the necessary uniformity of air flow over the entire height of the terminal element 4, two air supply ducts must be provided: one on the lower side and one on the upper side of the plenum 3 feeding the terminal element 4.

In the vicinity of the multifunction apparatus, the supply duct 2 doubles, one duct 24 serves the lower portion 7 of the plenum 3 from below, another channel 25 feeds the upper portion 7 of the plenum 3 from above.

The doubled ducts 24, 25 have dampers 26, 27, which are driven by the automatic regulation system, which divide the supply air into the high and low ducts 25, 24, depending on the temperature of the supply air, or the difference between the temperature of the supply air and the room. The hotter the air, the more it is conveyed to the lower part, vice versa, the colder it is, in the upper part.

This solution, obtained by specialising the upper duct 25 for cooling and the lower duct 24 for heating, does not present the problem of the unacceptable change in the distribution of air in the plenum, described in relation to the solution illustrated in FIGS. 61, 62, in which if a duct is fed from only one side it would be suitably balanced by bringing only hot air or only cold air.

In this case, therefore, both ducts, high 25 and low 24, can also be located above and below the supply plenum 3. The two ducts, high 25 and low 24, have air passage openings, respectively indicated by 28a and 28b, placed on the horizontal sides of the two ducts 24, 25 and equipped with calibration dampers 29, 30, which can also be replaced by orifices or perforated sheets with predetermined air passage.

The calibrations of the dampers 29 placed on the inlet air supplies in the upper part of the plenum will be carried out with an average air temperature necessary during cooling, while the calibrations of the dampers 30 placed on the supplies of the lower part will be carried out with an average air temperature air necessary during heating.

In this embodiment, a partitioning wall 6 is included inside the plenum with a slot with a predetermined air passage section, both to control the rise of hot air from the lower portion 7 to the upper portion 7 of the plenum 3, when the air is introduced hot from below, and to control the descent of cold air from the upper portion to the lower portion of the plenum 3, when the air is introduced cold from above.

The electronic regulation device acting on the dampers 26, 27, in addition to driving them to distribute the supply air in the high and/or low duct 25, 24, as a function of the supply air temperature, or the difference between the temperature of the supply air and the room, can possibly have further functions, namely: correcting its own regulation action by checking it in feedback with the surface temperature sensors 10 of the terminal element 4, also to possibly favour, in relation to specific needs, more or less intensely the distribution of hot air in the lower part or cold air in the upper part of the terminal element 4; varying the amount of supply air as a function of the demand of sensors placed in the room at a distance from the terminal element 4, so as to obtain better control of the temperature and/or quality of the air in the room itself, also taking into account other parameters detected by relative sensors.

FIG. 72 illustrates a further embodiment with two opposite terminal elements 4 with respect to the plenum 3, consisting of two opposite faces 13, 14 capable of emitting air, in an entirely similar manner to those of the examples illustrated in FIGS. 10, 38 and 69.

In all the examples comprising two opposite multifunction terminal elements 4, these can form a partition between one area and the other of the room, with both faces 13, 14 facing the room to be treated so as to effectively air condition also relatively large surface rooms.

6.5.6) Versions with Dividing Distributor Inside the Plenum.

Figures 73, 74:
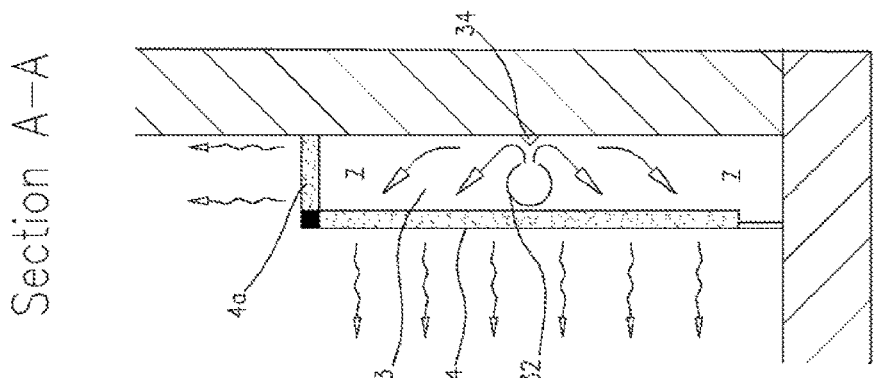
Figure 75:
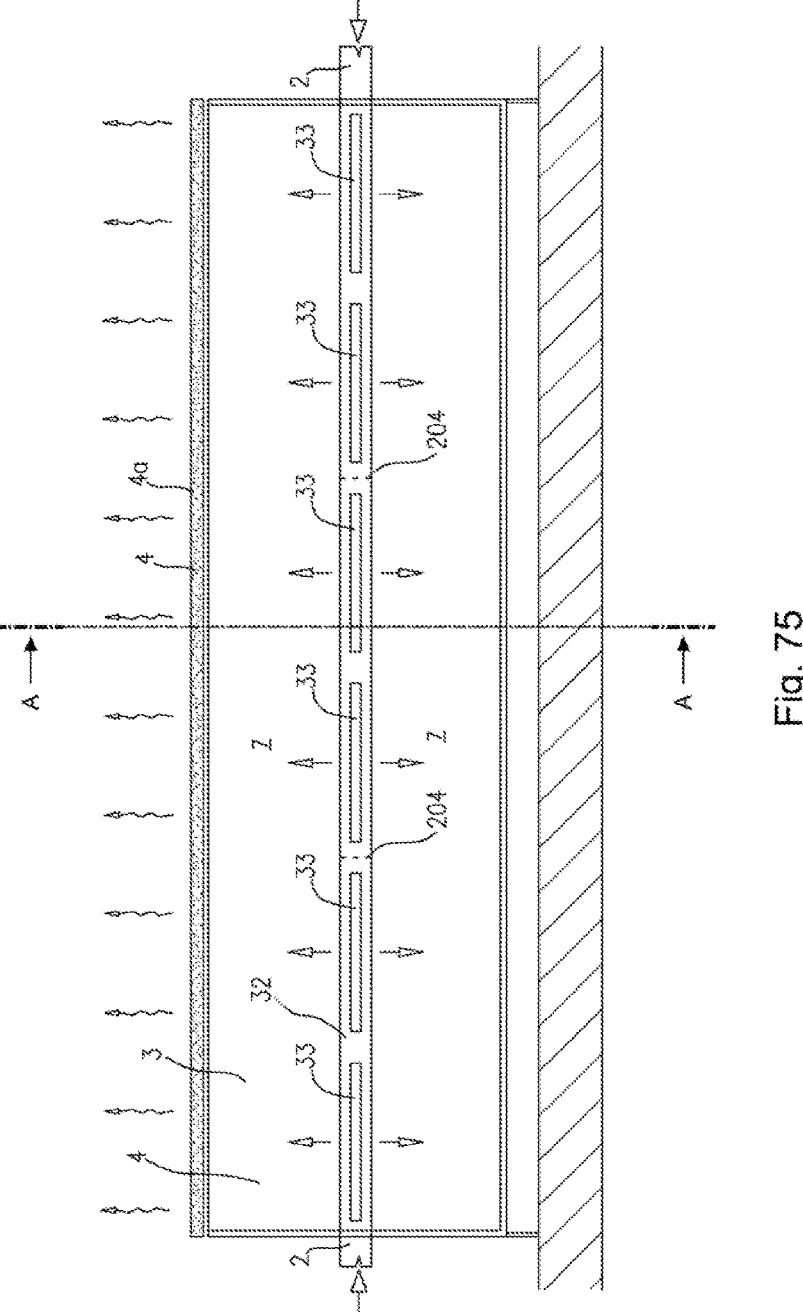

FIGS. 73 to 79 illustrate other embodiment examples of multifunction apparatuses characterised by terminal elements 4 with a height limited to about 1 metre for which, unlike the examples described above, it may be sufficient to use a longitudinal channel 32 placed inside the plenum 3 and fed by an aeraulic duct 2, as seen in FIG. 73. If the terminal element 4 has a length of more than about 2 metres, it is preferable to feed the inner channel 32 from both sides, as seen in FIG. 75. The channel 32 is provided with air exit slots 33. In both cases, in order to evenly distribute the air exiting the slots 33, the perforated calibration partitioning walls 204 should be inserted inside the channel 32.

More in detail, FIGS. 73 to 75 show a lateral terminal element 4 and a terminal element consisting of an upper face 4a capable of emitting air.

To limit the stratification of the air, if hot, in the upper part and the fall of the air, if cold, in the lower part of the plenum, the channel 32 can be positioned almost adhering to the internal surface of the terminal element 4, facing the plenum 3, so that the channel 32 itself creates an inner division at half height, becoming an internal dividing channel 32 to obtain the two portions 7, high and low, of the plenum 3 and to diffuse the air inside the plenum.

In particular, the channel 32 is provided with air exit slots 33 towards a baffle 34 which can be placed on the internal wall of the plenum 3 facing the slots 33 themselves, or attached to the diffuser channel itself (not shown in the figures), so as to divert the air towards the upper and lower part of the plenum 3.

The jet of air itself through the slots 33 on one side, and the channel 32 positioned towards the introduction surface inside the plenum 3 on the other, act as a barrier and hinder the possible descent of cold air from the upper part to the lower part of the plenum 3, and vice versa hinder the ascent of hot air from the lower part to the upper part of the plenum 3.

The air deflected by the baffle 34 is then forced to exit in the room halfway from the upper part of the terminal element 4, and halfway from the lower part of the terminal element 4.

Figure 76:
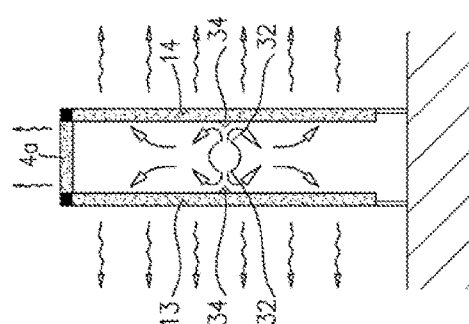

FIG. 76 illustrates a further embodiment with two opposite terminal elements 4 with respect to the plenum 3, consisting of two opposite faces 13, 14 capable of emitting air, in a completely similar manner to those of the examples illustrated in FIGS. 10, 38, 69 and 72, and further comprising a third terminal element 4 consisting of the upper face 4a capable of emitting air; in more detail, in FIG. 76 an internal diffuser channel 32 is seen, positioned centrally in height in the plenum 3 and affected by two opposite distributions of slots 3 facing two respective baffles 34, positioned on the internal wall of the terminal elements, facing the slots 33 themselves, or attached to the diffuser channel itself (not shown in the figures).

The solution of FIG. 76 is also particularly adapted to be positioned inside rooms, for example to form a partition between one area of the room and another, so as to effectively air condition even rooms with a relatively large surface area.

Figure 77:
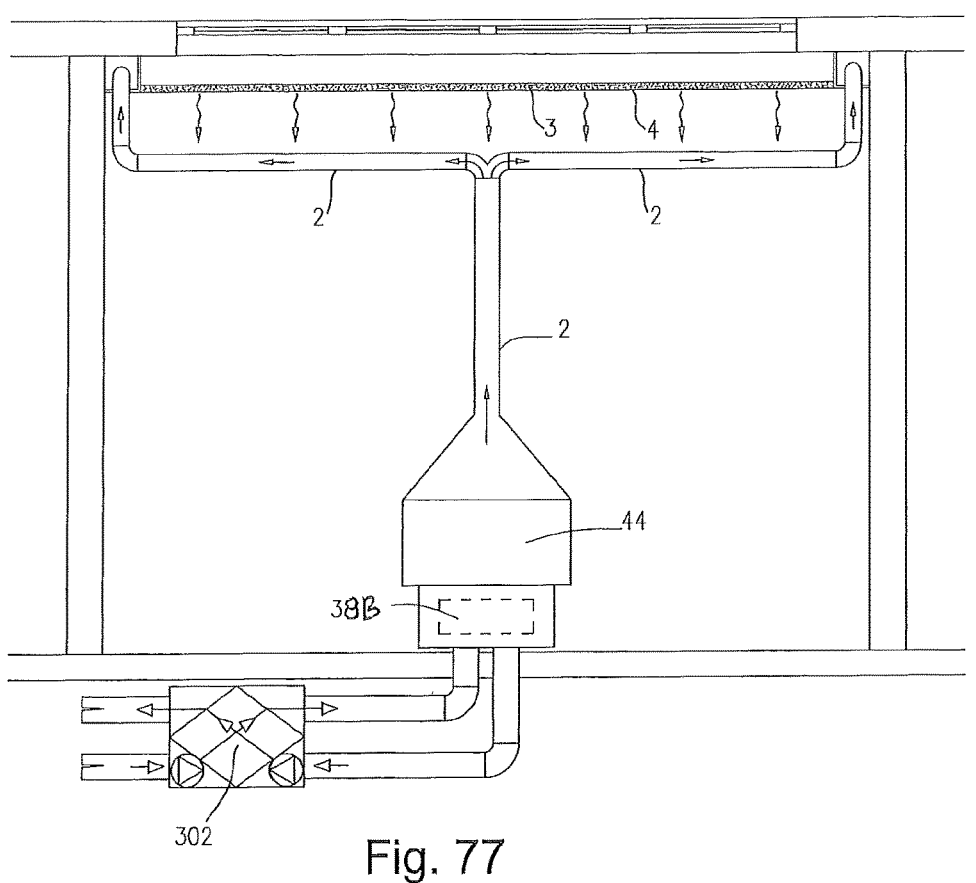
Figure 78:
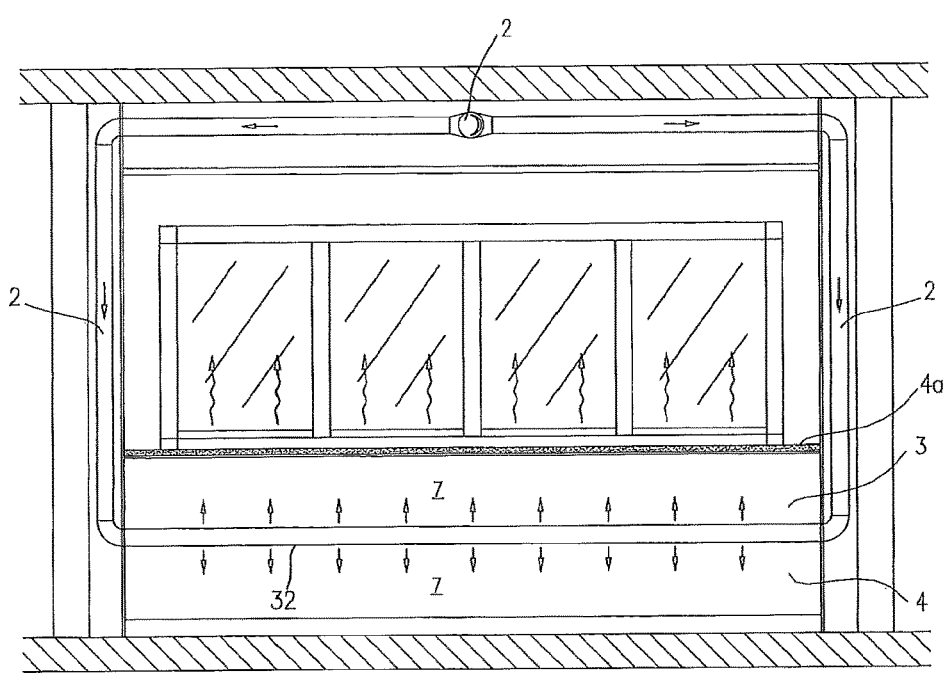
Figure 79:
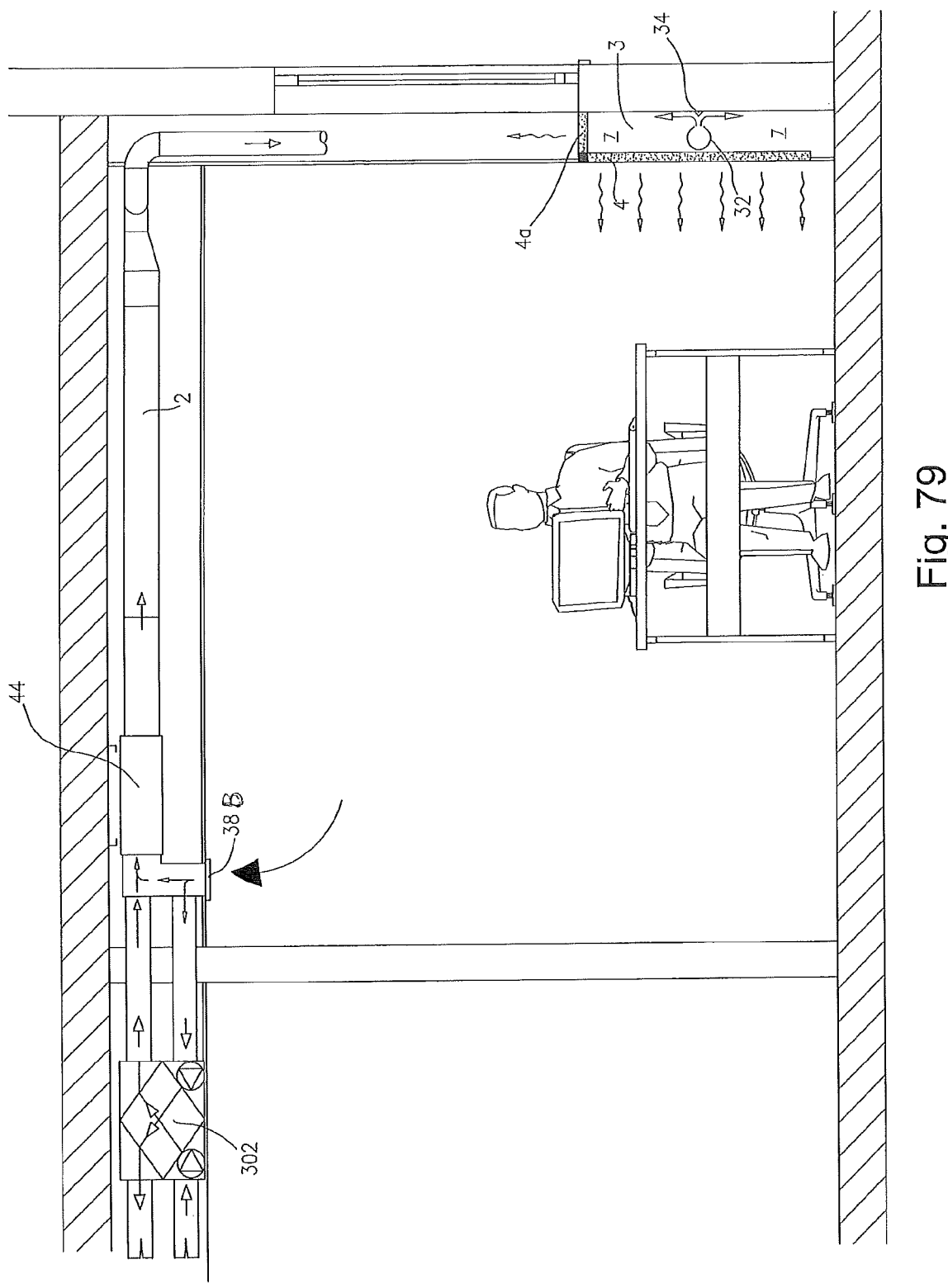

FIGS. 77 to 79 show an example of a possible application of the multifunction apparatus referred to in FIGS. 74 and 75, positioned against an external wall, below the windows, of an office.

The system is fed by the fan coil 44 and by the apparatus 302 for air change with recovery of the thermal energy of the expelled air.

FIG. 77 depicts the system in plan view, the fan coil 44 after having thermo-hygrometrically treated the air sends it to a duct 2 to feed the multifunction apparatus 1.

The duct 2 branches into two aeraulic ducts descending vertically from the ceiling so as to supply the horizontal diffuser tube 32, visible in the front and side sections of FIGS. 78 and 79: the diffuser tube 32 distributes the conditioned air in the plenum 3, placed vertically against the wall below the windows and associated with a lateral terminal element 4 and an upper element consisting of a second face 4a capable of emitting air, as explained in detail already in the description related to FIGS. 73 to 75.

The air introduced by the terminal elements moves away crossing the entire room, air conditioning and renewing the air efficiently, as it is sucked in by the intake grille 38A. 38B located on the opposite side to the air introduction into the room.

A part of the air taken in through the grille 38A, 38B is sucked from the air renewal apparatus 302 and expelled to the outside, after having passed through the heat recovery apparatus if free cooling is not necessary; the remaining intake air is sucked by the fan coil 44, together with the external renewal air coming from the air change apparatus 302.

6.6) Multifunction Apparatuses with Horizontal Extension.

As anticipated in the initial part of chapter 6.2), constituent elements of the embodiments, a variant of the vertical multifunction apparatuses 1 can be obtained by separating the upper portion 7 of the apparatus itself from the main vertical body and positioning it horizontally at a higher height. Such a portion therefore forms a plenum 3 on its own, fed by an air duct 2 derived from the main duct that also feeds the vertical apparatus, and includes systems for regulating/varying the air conditioning flow rate between such a horizontal portion and the portions in the vertical body.

In the horizontal embodiments with a length greater than 2 metres, to regulate the internal distribution of the conditioned air as a function of the temperature and/or the supply flow rate for the subsequent homogeneous exit of the air at low speed towards the rooms to be treated while maintaining the characteristics of low pressure loss and correct operation even with the variation of the temperature and air flow rate, it is essential to adopt partitioning walls and/or dividing diaphragms 6 and systems for the optimised dynamic distribution of the air upstream of the terminal elements 4, which can comprise a movable deflecting fin 231, arranged on the inlet opening 5, to deflect part of the supply air towards the upper or lower portions of the plenum 3.

In other possible embodiments, some of which are depicted in FIGS. 80 to 85, the multifunction apparatuses can be designed in a suitable version to be able to function correctly if arranged horizontally, for example on the ceiling. FIGS. 80 to 83 show a modular version up to 6-7 metres in length, also depending on the height of the relative plenum 3, with a single conditioned air supply.

Figure 83:
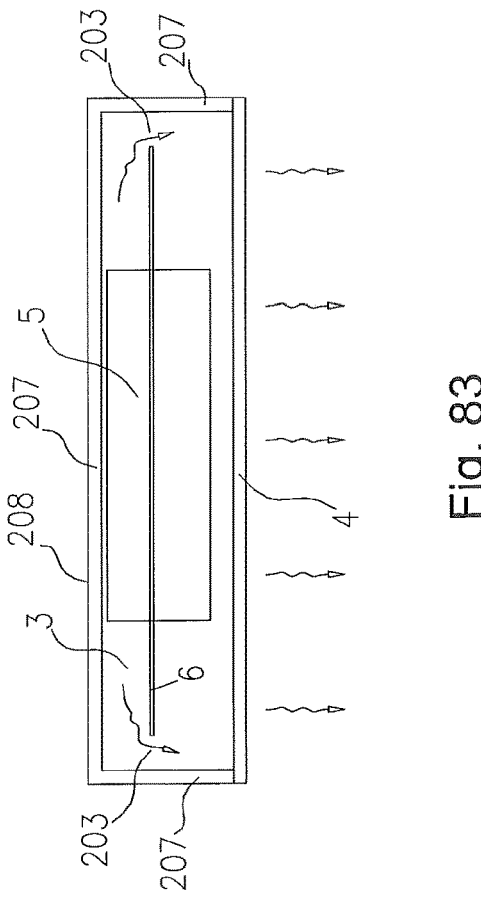
Figure 82:
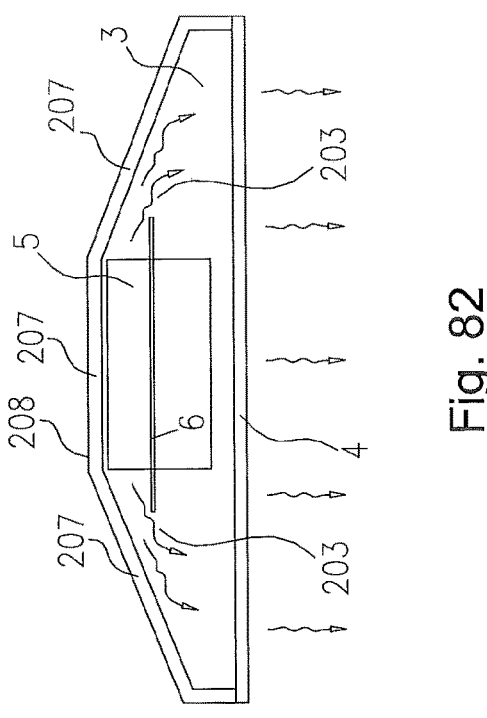

The multifunction apparatus is equipped with a plenum 3 with horizontal longitudinal extension, connected on one side, through the air supply opening 5, to the supply air duct 2 coming from a centralised air handling unit AHU, or localised FCU, in the latter case the fan coil can also be connected directly to the air inlet opening 5 in the plenum. The plenum 3 is partially divided in height into two portions by means of the partitioning walls 6 spaced from each other so as to have passage intervals 203 through which the air passes from one portion of the plenum to another; as can be seen in FIGS. 82 and 83 said air passages can also be present laterally at the partitioning walls 6. Depending on the various dimensional shapes of the apparatus, the partitioning walls 6 can also have the surface perforated. An adjustable deflecting fin 231, by rotating on the rotation pin 206 can deflect part of the supply air towards the upper or lower portion 7 of the plenum 3, to vary the distribution in height thereof. The cooler the supply air, the more the fin will be rotated to orient the air towards the upper partition of the plenum, to compensate for the natural behaviour of cold air to fall early along the longitudinal progress in the plenum. The air deflected towards the upper wall of the plenum, aided by the ceiling effect and the path channeled above the partitioning walls 6, will retain its progress until the end of the plenum, descending along the path through the open spaces 203, to feed the terminal element 4 together with the part of air not deflected towards the upper part of the plenum, which continues its longitudinal path in the lower portion 7 of the plenum 3 below the partitioning walls 6. Conversely, the warmer the supply air, the more the fin rotates to deflect the air towards the lower portion of the plenum, so as to compensate for the natural behaviour of hot air to adhere to the upper wall of the plenum and exit more at the end of the terminal element; in this case the partitioning walls 6 help the deflected air in the lower part to advance below the partitioning walls, thus near the internal surface of the terminal element. Depending on the cases and the temperatures of the air in the design, the rotation pin 206 of the deflecting fin 23 can be positioned more or less offset with respect to the centre of the fin, so as to vary the extent of the fin part that protrudes rearwards towards the supply opening 5. It is thereby possible to adapt the regulation characteristics of the blade, to vary the ability thereof to capture more or less air from the supply opening 5 during the rotation of the blade itself. The regulation of the rotation of the fin 231 can also occur by means of automation, with thermostatic or electronic actuators. In the latter case, the regulation of the deflecting fin will preferably occur according to the temperature difference between the supply air and the room at a height representative of the area occupied by people. In the case of electronic regulation, it will also be possible to move the fin according to specific programs which can also envisage oscillatory movement in swing mode.

These peculiarities allow to make a multifunction apparatus up to 5 metres long with a single air supply inlet, capable of adapting to the various operating conditions of the system.

The length of 6-7 metres can be reached by connecting several modules together, for example for a 6-metre apparatus, two 3-metre long pieces connected in series can be joined, of which the first module on the arrival side of the conditioned air is provided with supply opening 5 and regulation fin 231 and on the opposite side it is open, while the second module has an open side that couples with the open side of the first module is the opposite side provided with a closed vertical terminal wall 207.

The horizontal multifunction apparatuses can also be mounted at a height detached from the ceiling of the room, especially in rooms higher than three metres. Nowadays this already frequently occurs to create sound-absorbing aerial islands. Given the characteristic of the multifunction apparatuses to be able to also fulfil this task while simultaneously performing the air conditioning function, the apparatuses of the present invention can be hung in place of the sound-absorbing panels to simultaneously also perform their function. To increase the sound-absorbing effect, the multifunction apparatuses can also be constructed with the walls 207 of the plenum made using high-density sound-absorbing mats, with the sound-absorbing surface 208, indicated in FIGS. 82 and 83, facing the outside of the plenum, i.e., towards the room. The plenum can have the walls shaped with a trapezoidal section, as in FIG. 82 or rectangular, as in FIG. 83.

Figure 84:
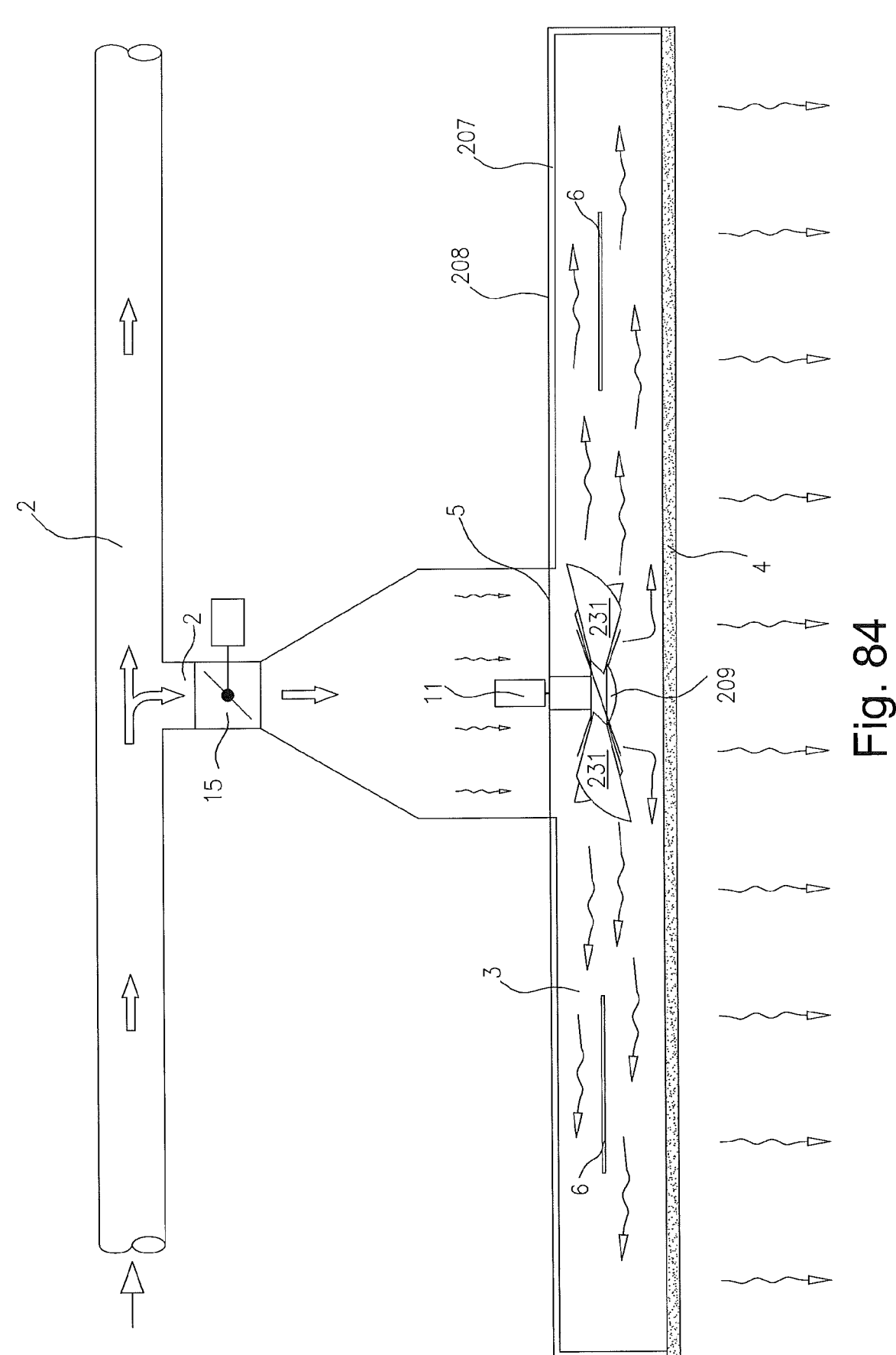
FIGS. 84 and 85 illustrate another horizontal embodiment of the multifunction apparatus

In FIG. 84 another example embodiment of a horizontal multifunction apparatus positioned on the ceiling is shown, in which, unlike the previous example, the aeraulic duct 2 is arranged above the plenum. The conditioned air coming from an air handling unit 301, is conveyed through the duct 2 to the air inlet opening 5 in the plenum 3, placed centrally thereto. Depending on the shape of the last section of duct 2 upstream of the opening 5, the latter can possibly be equipped with a perforated equalisation sheet. An apparatus 209, equipped with a servo control 11 and deflecting fins 231 arranged radially so as to impart a helical motion to the air, provides for uniform diffusion of the air inside the plenum, rotating the deflecting fins to vary the inclination, as a function of the temperature of the supply air. Said regulation can occur by means of thermostatic or electronic actuators. In the latter case, the regulation of the deflecting fins will preferably occur according to the temperature difference between the supply air and the room at a height representative of the area occupied by people. In the case of electronic regulation, it will also be possible to move the fins 231 according to specific programming that can also envisage the oscillatory movement in swing mode.

Figure 80:
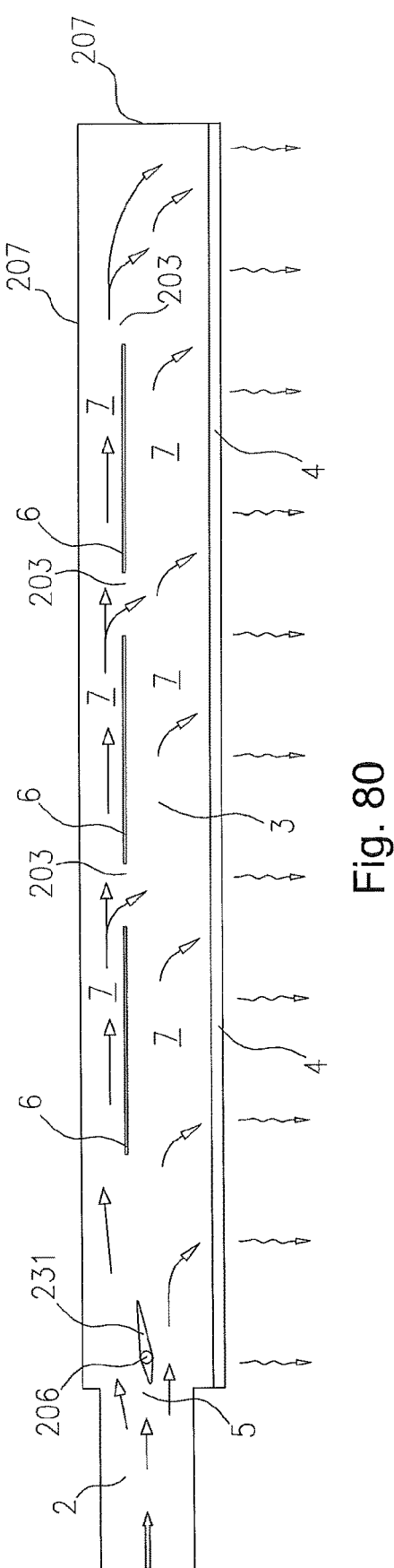
FIGS. 80 to 83 illustrate an embodiment of the multifunction apparatus according to the concept of a horizontal version of the present invention.
Figure 81:
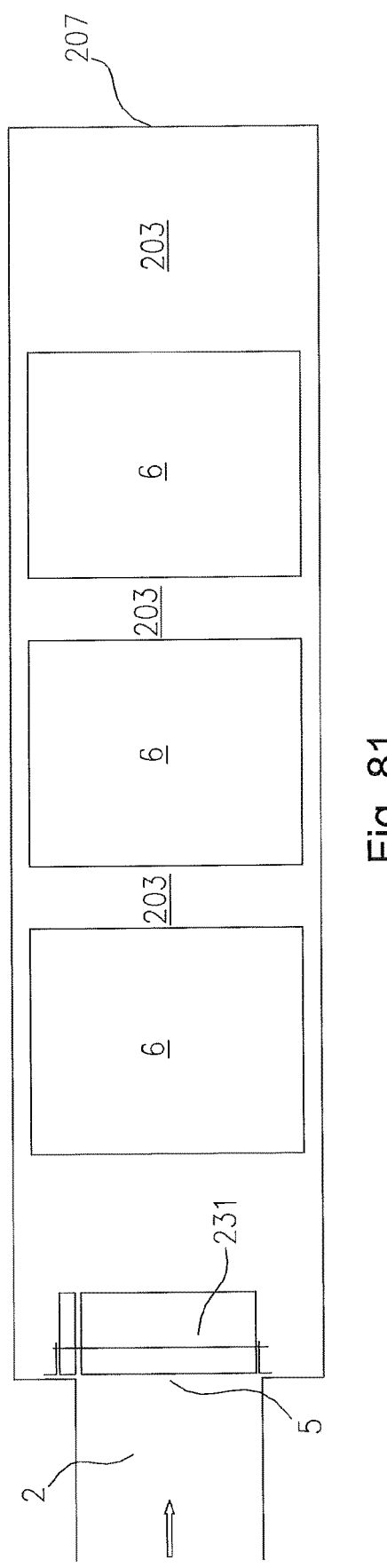

In some cases, depending on the flow rates and temperatures of the air in the design and the internal height of the plenum, if the size of the latter exceeds about 2.5-3 metres per side, it is appropriate to add inside the plenum 3 of the partitioning walls 6 that go to portion the plenum in height, operating according to the same principle already explained in the previous example related to FIGS. 80 and 81. By virtue of the apparatuses and expedients described above, the air will be diffused uniformly inside the plenum both in heating and cooling, and then exit uniformly from the terminal element 4 towards the underlying room.

When the multifunction apparatuses are positioned only horizontally on the ceiling, to properly air condition the room and obtain efficient ventilation in order to ensure the quality of the indoor air, it is appropriate to position and properly distribute the air intake with suction in the lower part of the room, especially during the heating function.

Figure 85:
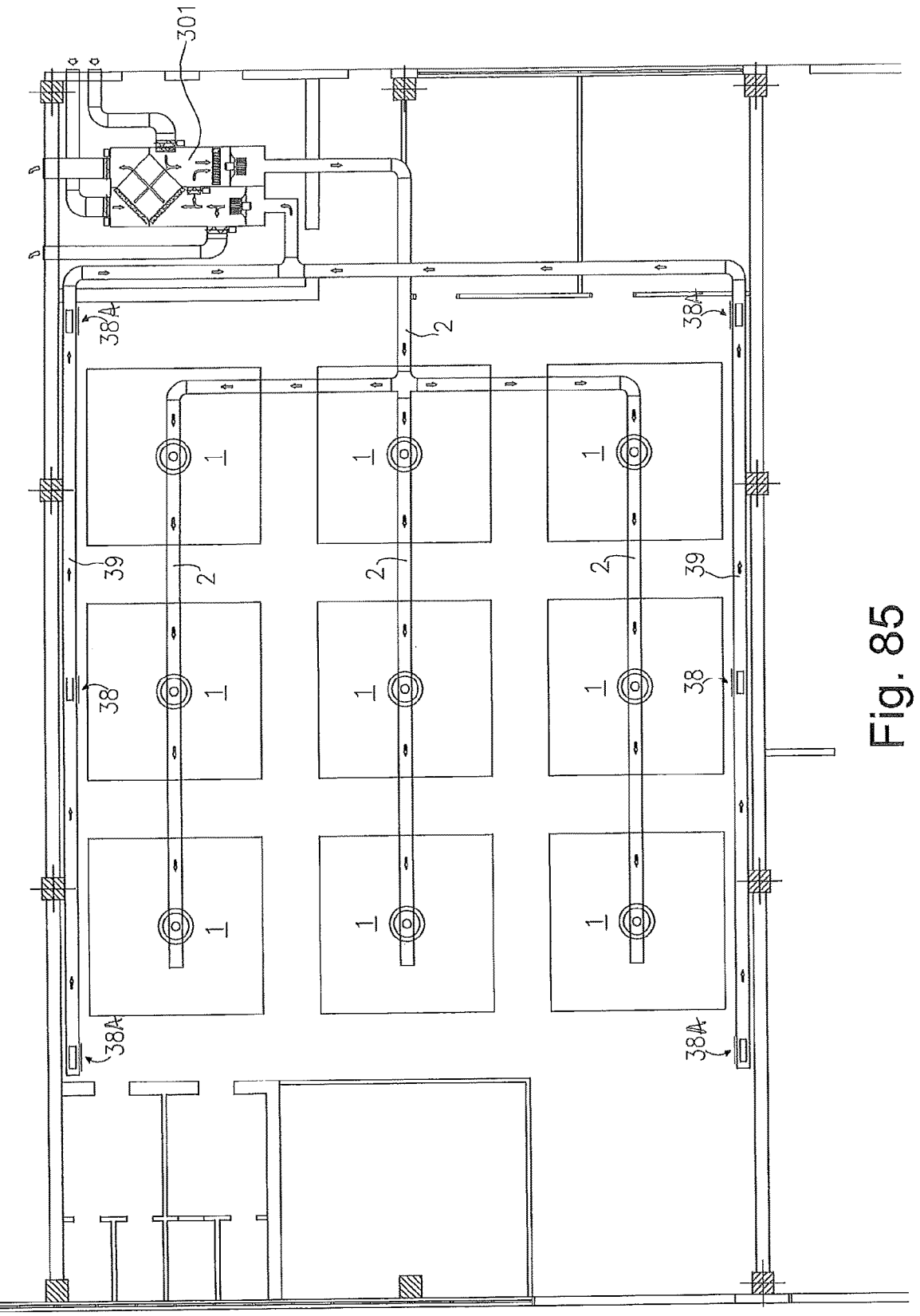

In this regard, FIG. 85 shows several multifunction apparatuses 1 such as those now described for FIG. 84, associated and connected through the aeraulic ducts 2 to the air handling unit 301 of a room, such as for example a supermarket. More in detail, in the lower part of the room, in the example at the base of the walls, intake grilles 38A are included, connected to the aeraulic air intake ducts 39, for the suction of the latter in the handling unit 1, so as to treat it and renew it properly before re-introduction into the aeraulic duct 2 for supplying the multifunction elements 1.

6.7) Examples of Embodiments with Vertical and Horizontal Extension Multifunction Apparatuses.

Further possible examples of embodiments, some of which are depicted in FIGS. 1A and 1B related to a clothing store, as well as in FIGS. 90 and 91 related to a newly designed building, both of which are already described as first examples in chapter 6.2), include multifunction apparatuses and/or the related terminal elements 4, arranged both vertically and horizontally, for example for positioning on both the walls and on the ceiling.

Further embodiments are shown in FIGS. 86, 87A, 87B, 88-89, 92-93.

Figure 37:
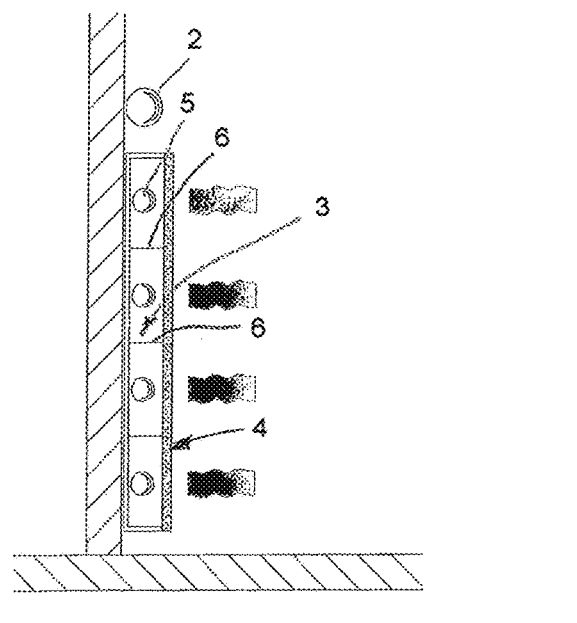
Figure 86:
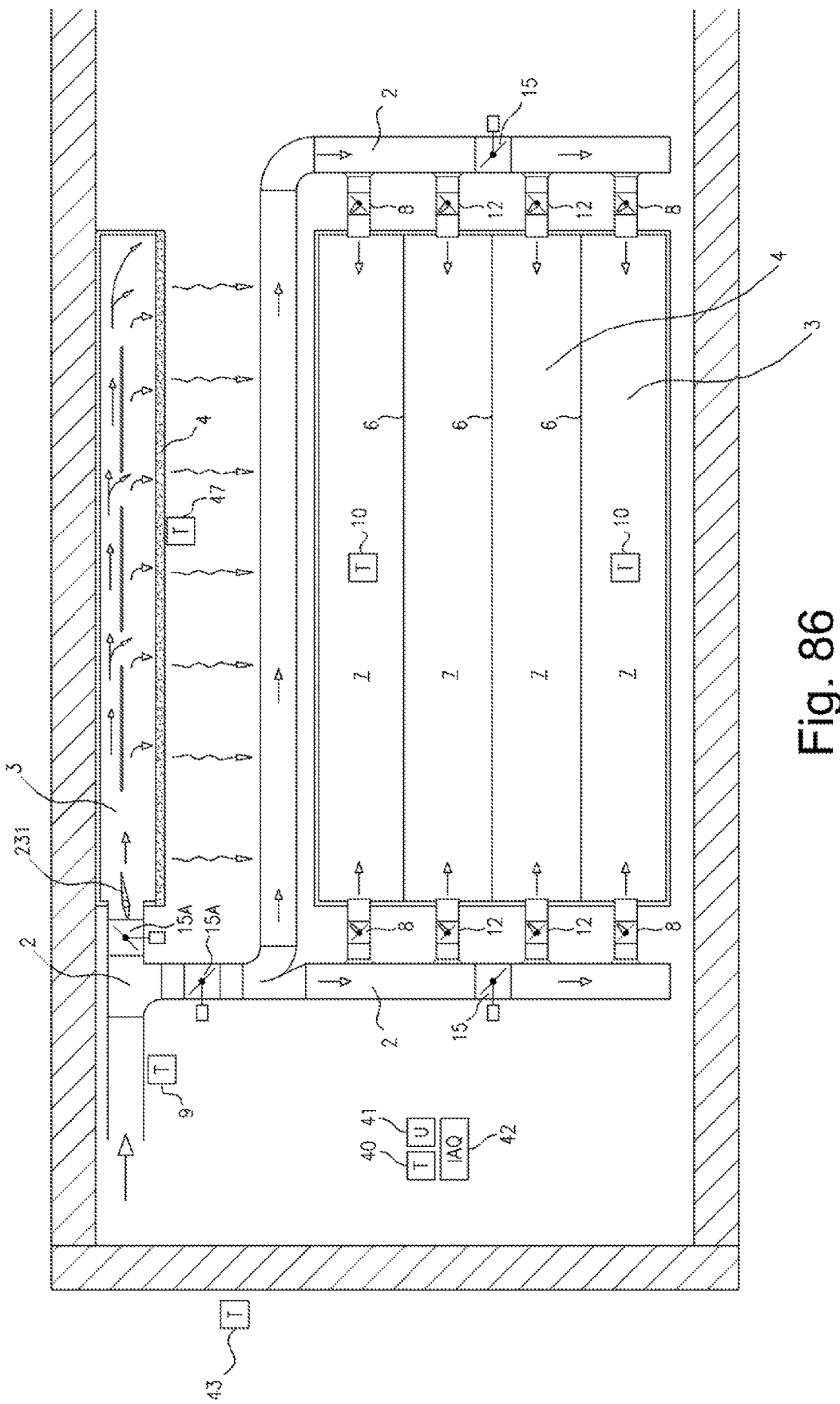
FIGS. 86 to 93 illustrate some forms of application in which multifunction apparatuses arranged both vertically and horizontally can coexist

In an embodiment example of a system, depicted in FIG. 86, the supply air, coming from the relative handling unit 301 (not shown in the figure), is conveyed through the ducts 2 both to the vertical multifunction apparatus, completely similar to that described in the embodiment example depicted in FIGS. 36 and 37, and to the horizontal multifunction apparatus positioned on the ceiling, of the type described in the embodiment example in FIGS. 80-81.

The automatic regulation system included for the most advanced solutions can control, as a function of the temperature of the supply air, or as a function of the difference between the temperature of the supply air detected by the probe 9 and the room temperature detected by the probe 40, the following regulation members:

the opening of the motorised dampers 15A to optimally distribute the supply air between the multifunction apparatuses positioned on the ceiling and on the wall;

the regulation of the air distribution fin 231 within the horizontal apparatus placed on the ceiling;

the opening of the air distribution dampers 15 within the vertical apparatus placed on the wall All according to the logic already set out in the previous parts of the report.

The automatic system can further act on the motorised dampers 15A to adjust the supply air flow rate to the relative apparatuses as a function of the needs of the internal room, air renewal and free cooling, verified through the sensors of internal temperature and humidity 40 and 41, internal air quality 42 and external temperature 43.

Figure 87A:
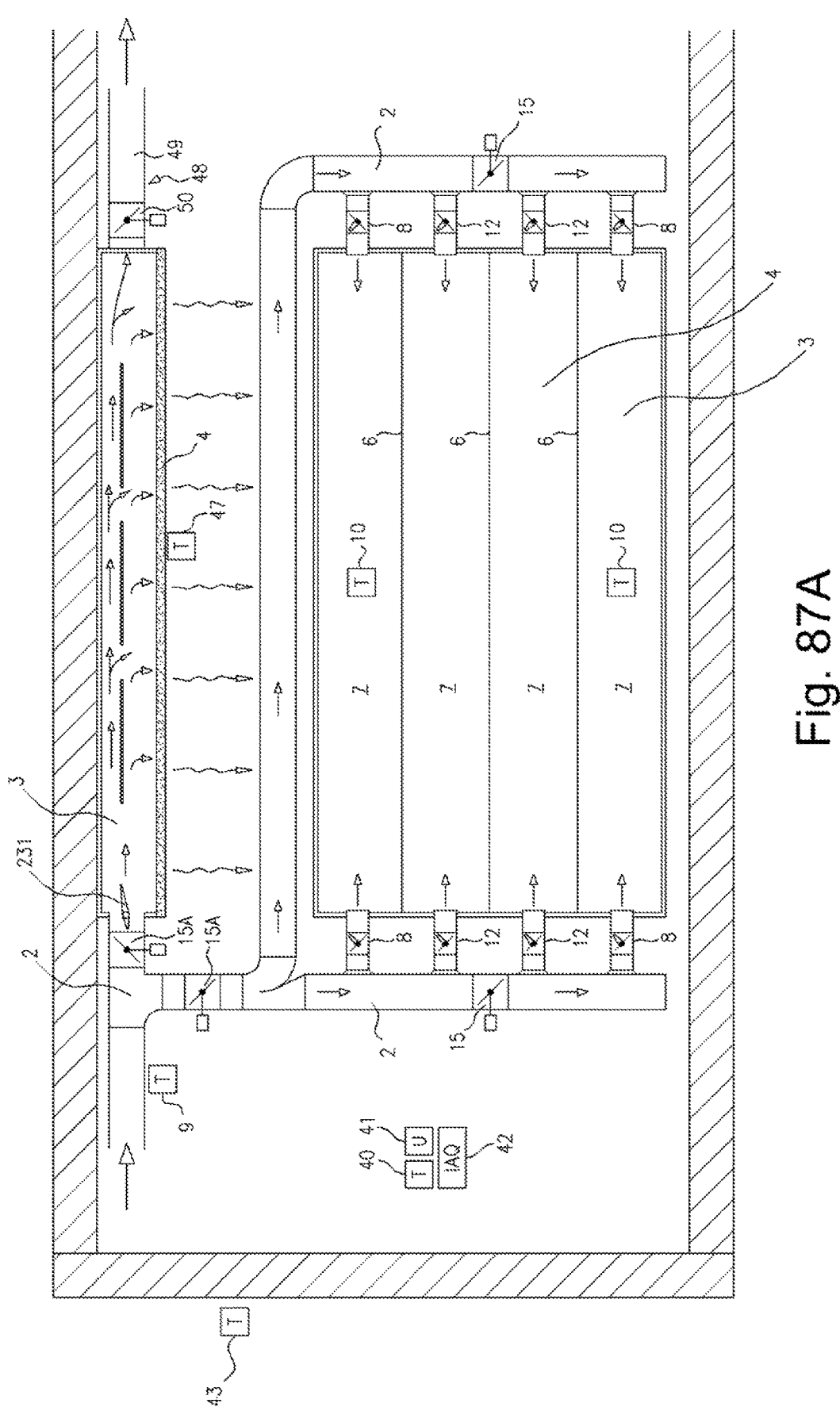
Figures 92, 93:
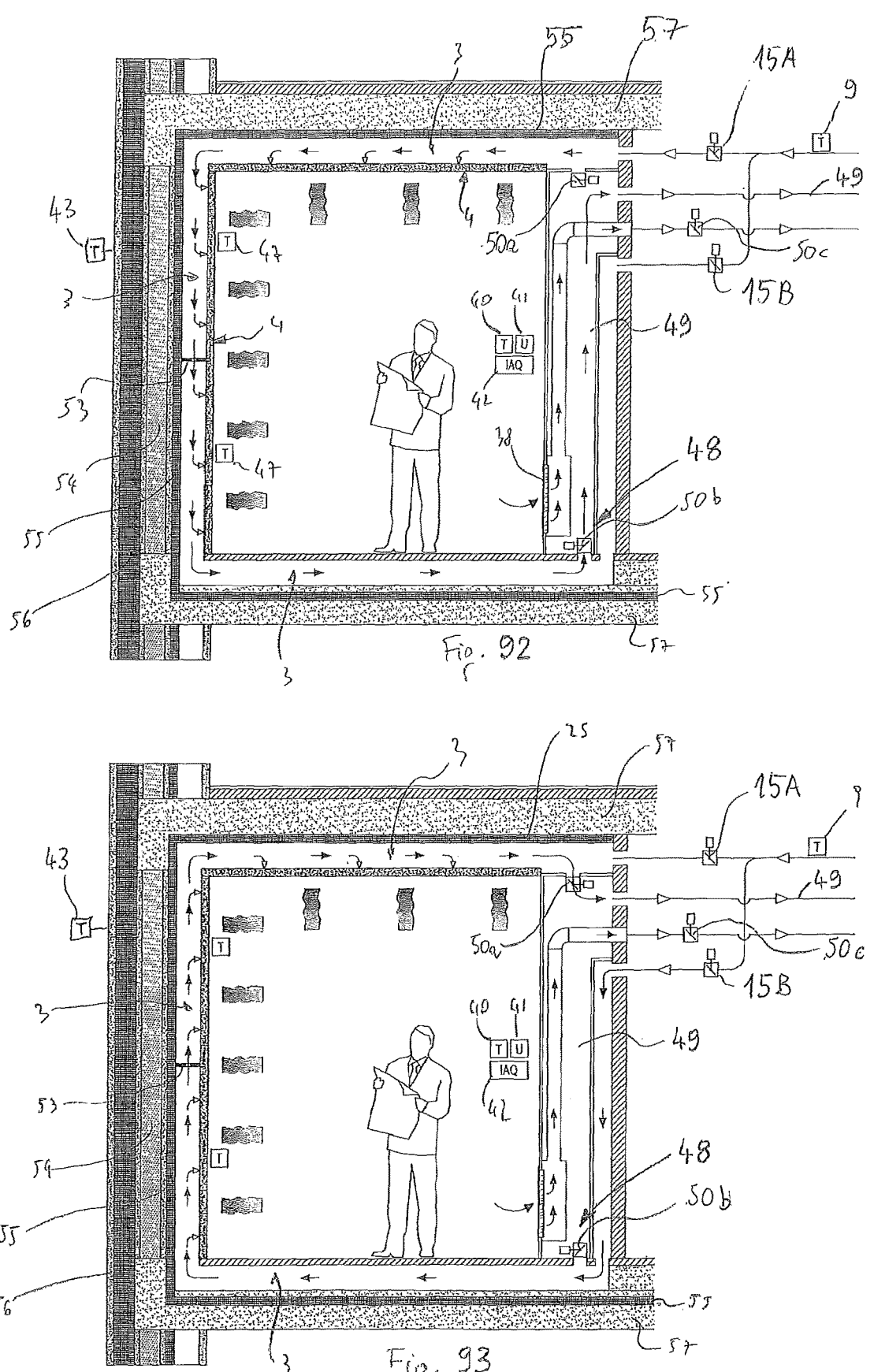

In some embodiments, depicted in FIGS. 87A, 92-93, the system can be equipped with an optional device for partial recirculation of the air in the plenum that contributes to maintaining a suitable temperature uniformity and an effective radiant effect of the terminal elements 4 under certain conditions, reducing the amount of air exiting towards the room, without reducing the amount of supply air: through such a device, a predetermined part of the supply air, after exchanging heat with the internal surface of the terminal element 4, can be recirculated by the HVAC system, without having exited from the terminal element 4 towards the room.

FIG. 87A illustrates a possible embodiment of the previous system depicted in FIG. 86, with in addition the aforementioned partial air recirculation device 48 in the plenum 3, which allows to maintain a suitable temperature uniformity and a good radiant effect of the terminal elements 4, reducing the amount of air exiting to the room, without reducing the amount of supply air.

The operation of the partial recirculation device 48 is as follows:

through a supplementary intake duct 49, placed in communication with the plenum 3 positioned on the ceiling, a part of the supply air, after exchanging heat with the internal surface of the terminal element 4, is recovered from the HVAC system without having exited from the terminal element 4 towards the room.

The air sucked from the intake of the system directly by the plenum 3 has not been polluted by the transit in the room, it is therefore preferable to connect the supplementary duct 49 to the air handling unit 301 (not shown in the figure), so that the air in question is not expelled outside, but reused.

The automatic regulation system acts exactly as that of the embodiment example of FIG. 86 above, with the further possibility of automatically regulating the air flow rate sucked directly by the plenum 3, by means of at least one motorised damper 50 located in the supplementary intake duct 49.

Such a function can be useful, for example, to be used during the heating season, adding a logic to the automatic regulation system that activates the partial air recirculation function in the plenum of the terminal element 4 positioned on the ceiling, to increase the radiant effect thereof, leaving the ventilation functions mainly to be borne by the vertical multifunction apparatuses.

Figure 87B:
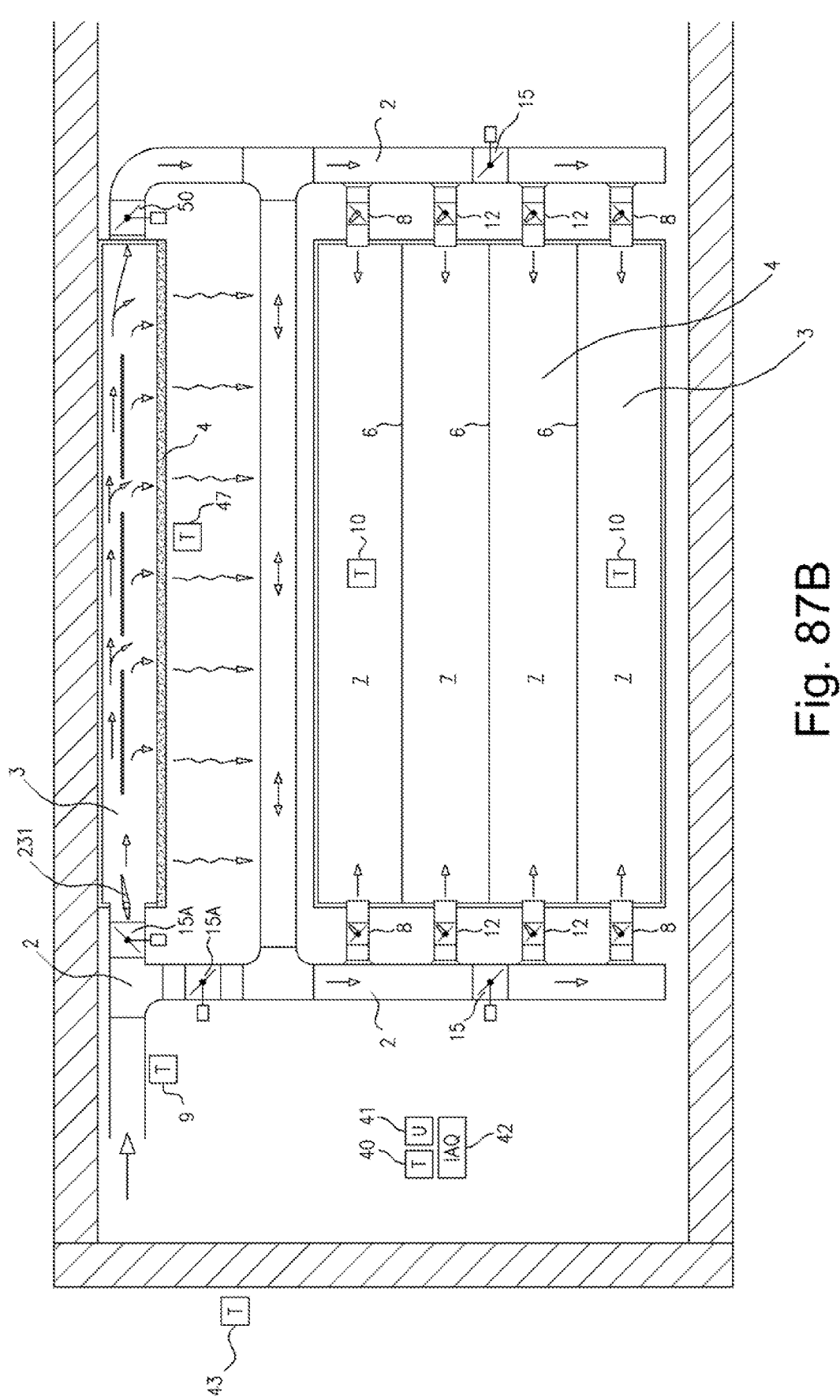

A variant adapted to decrease the amount of air exiting from the terminal element 4 of the horizontal apparatus, without reducing the entering air flow rate, can be obtained as depicted in FIG. 87B, supplying in series a horizontal multifunction apparatus with a vertical apparatus. In this case, the supply air enters the horizontal apparatus and then exits from the opposite side after having crossed the entire length of the apparatus. A duct connects such an outlet with the inlet to the vertical apparatus, which is then fed with the air that has previously passed through the entire horizontal apparatus. On the duct that connects the outlet from the horizontal apparatus with the inlet to the vertical apparatus there is at least one damper 50, to adjust the amount of air entering the vertical apparatus. The less air to be made to exit from the horizontal apparatus, the more the damper 50 opens and vice versa. Thereby, especially during heating, it is possible to increase the radiant effect of the horizontal apparatus leaving the ventilation functions mainly borne by the vertical multifunction apparatuses.

The automatic regulation system acts exactly like that of the example embodiment of FIG. 86 above, with the additional possibility of automatically regulating, through at least one motorised damper 50 located in the duct connecting the end of the horizontal apparatus with the supply of the vertical apparatus, the air flow rate that instead of exiting from the horizontal apparatus goes to the vertical one, also in parallel to its main supply, which can also remain, controlled by the relative regulation damper 15.

According to other versions of the present invention, not illustrated in the figures, the horizontal multifunction apparatuses 1 can also be fed in series with each other and/or with the vertical multifunction apparatuses 1; in turn the vertical multifunction apparatuses 1 can also be fed in series with each other and/or with the horizontal multifunction apparatuses 1.

Figures 88, 89:
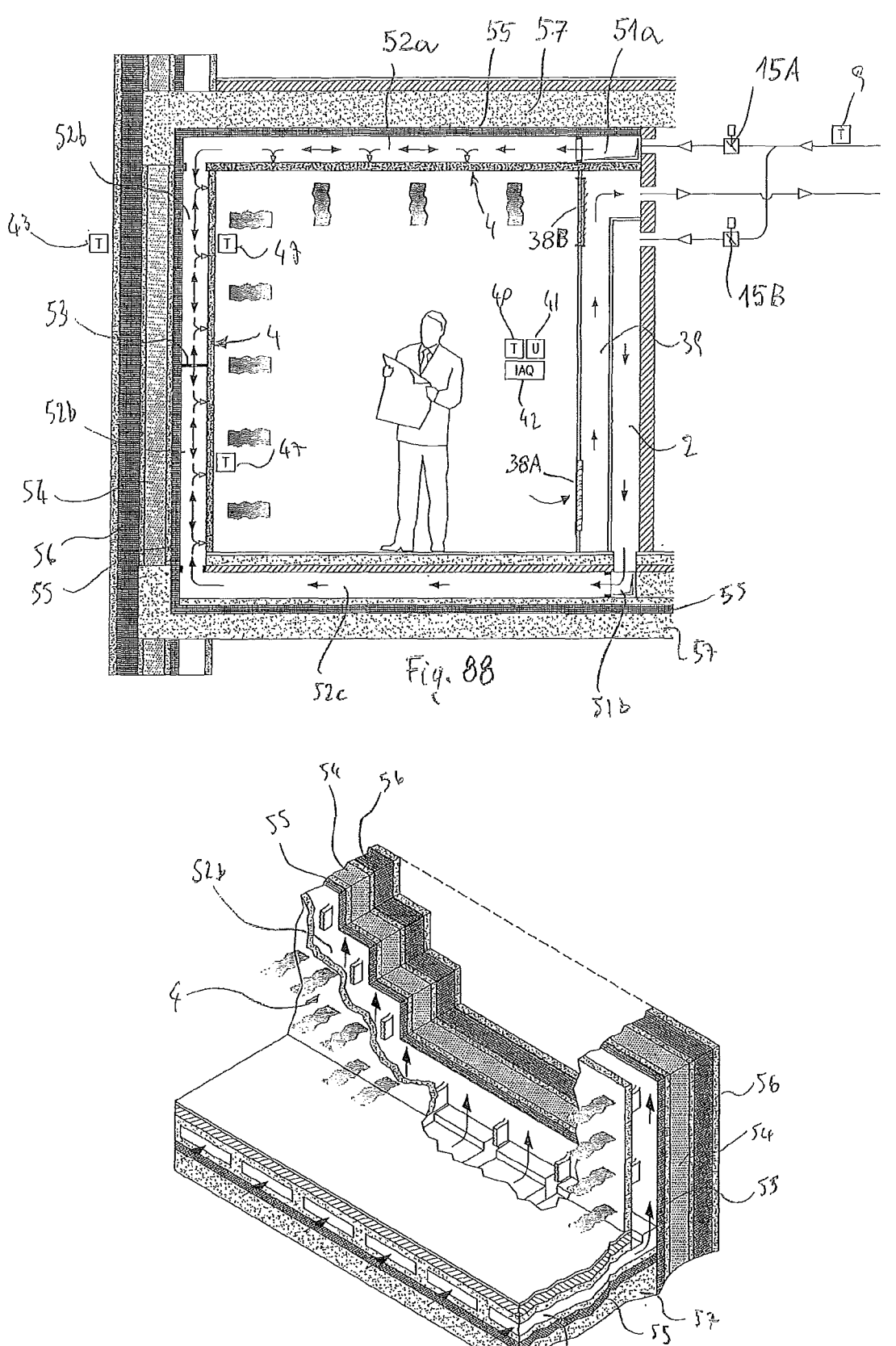

FIGS. 88 and 89 show an example of the construction of the system obtained in a building comprising air passages previously included in the structure of the building itself:

the supply air, coming from the relative handling unit 301, supplies the terminal elements 4 positioned on the ceiling and on the wall in the following manner: the supply air is introduced into the upper manifold duct 51*a*, to supply the air passages 52*a* arranged in the structure on the ceiling, which in turn supply the air passages 52*b* arranged in the structure on the wall.

The ceiling and the wall of the room located at the air passages 52*a* and 52*b*, have the part facing the room made of material permeable to air, and therefore directly form the terminal elements 4.

The supply air is also introduced into the lower manifold duct 51*b* by a duct 2 to supply the air passages 52*c* arranged in the structure on the floor, which in turn feed the air passages 52*b* arranged in the structure on the wall, and in series the air passages 52*a* arranged in the structure on the ceiling. The air passing through the passages 52*c* warms the floor, without letting air exit from the floor into the room.

Approximately halfway through the air passages 52*b* arranged in the structure on the wall, a separation partitioning wall 53 can possibly be inserted comprising pre-calibrated means for the controlled passage of the air.

All the supply air passes through the thickness of the terminal elements 4 positioned on the ceiling and on the wall exiting the respective external surfaces permeable to air towards the room to be conditioned.

The surfaces of all the terminal elements 4 carry out a first combined radiation/convection heat exchange with the room, before the introduced air moves away from the external surface of the elements 4 themselves.

The introduced air then moves away from the terminal elements 4 and passes through the entire room, conditioning it and renewing its air properly, as it is sucked by the intake grilles 38A, 38B located adequately, at the bottom and/or at the top in the room, on the side opposite to that of the introduction of the air. The grilles 38A, 38B are in communication with intake ducts 39.

The automatic regulation system envisaged for the most advanced solutions, controls the dampers 15a and 15B which, in addition to regulating the air flows necessary—for air conditioning and the relative free cooling, as a function of the data detected by a room temperature sensor 40, a room relative humidity sensor 41, an indoor air quality sensor 42 and an outdoor temperature probe 43 distribute the supply air upwards and downwards in the room, as a function on the difference between the supply air temperature detected by the temperature sensor 9 and the room temperature detected by the room temperature sensor 40, all possibly optimised also according to the data detected by optional temperature probes 47 located on the external surfaces of the terminal elements 4.

In maximum cooling the damper 15A is open and the damper 15B is closed, the supply thus occurs from above; conversely, in maximum heating the damper 15A is closed and the damper 15B is open, the supply thus occurs from below.

As can be seen in FIGS. 88 and 89, the structure of the building referred to in the example comprises a vertical structural element 54, an internal thickness of thermal insulation 55, located between the vertical structural element 54 and the air passage 52b, and an external thickness of thermal insulation 56.

An internal thickness of thermal insulation 55 is also located between the air passage 52a arranged in the structure on the ceiling and the upper slab 57, another internal thickness 55 is provided between the air passage 52c arranged in the structure on the floor and the lower slab 57.

The two further examples of embodiments, depicted respectively in FIGS. 92 and 93, are systems corresponding to those now described and depicted respectively in FIGS. 90 and 91, but with, in addition, the aforementioned partial air recirculation device 48 in the plenum 3.

In the example of FIG. 92, the operation of the system in cooling, with air supply from above is diagrammed; in the example of FIG. 93, the operation of the system in heating, with air supply from below is diagrammed.

In cooling, as shown in FIG. 92, the temperature of the supply air (detected by the temperature sensor 9) is colder than the room temperature (detected by the room temperature sensor 40): the damper 15B closes, and the damper 15A opens, feeding the plenums 3 from above, regulating the necessary supply air flow according to the data detected by the sensors 40, 41 and 42, and possibly optional temperature probes 47 located on the external surfaces of the terminal elements 4.

In heating, as shown in FIG. 93, the temperature of the supply air (detected by the temperature sensor 9) is hotter than the room temperature (detected by the room temperature sensor 40), the damper 15A closes and the damper 15B opens, feeding the plenums 3 from below, regulating the necessary supply air flow according to the data detected by the sensors 40, 41 and 42, and possibly the optional temperature probes 47 located on the external surfaces of the terminal elements 4.

The partial recirculation device 48 allows to maintain a suitable temperature uniformity and a good radiant effect of the terminal elements 4 by reducing the amount of air exiting to the room, without reducing the amount of supply air.

The operation of the partial recirculation device 48 is as follows:

through supplementary intake ducts 49, placed in communication with the plenums 3 positioned on the ceiling and floor, a part of the supply air, after exchanging heat with the internal surface of the terminal element 4, is sucked by the HVAC system without having exited from the terminal element 4 towards the room.

The air sucked directly by the supply plenums 3 has not been polluted by the transit in the room, it is therefore preferable to connect the supplementary duct 49 to the air handling unit 301, so that the air in question is not expelled outside, but reused.

The automatic regulation system acts exactly like those of the previous examples which envisage the device 48.

In particular, in normal use conditions of the system, the dampers 50a and 50b of the partial recirculation device 48 are closed; instead, in conditions of need, due for example to inadequate surface temperatures (detected by the optional temperature probes 47 located on the external surfaces of the terminal elements 4) and absence of free cooling, compatible with the ventilation needs (detected by means of an internal air quality sensor 42), the automatic regulation device acts on the partial recirculation device 48 as follows: In cooling, as shown in FIG. 92, the damper 50a remains closed and the motorised damper 50b adjusts the air flow rate sucked directly by the plenum, or duct, placed under the floor.

The optional motorised damper 50c, located on the air suction duct from the room, is progressively closed in sequence with the opening of the damper 50b to increase the air sucked by the plenums 3;

In heating, as shown in FIG. 93, the damper 50b remains closed and the motorised damper 50a adjusts the air flow rate sucked directly by the plenum 3 positioned on the ceiling.

The optional motorised damper 50c, located on the air suction duct from the room, is progressively closed in sequence with the opening of the damper 50a to increase the air sucked by the plenums 3.

The sensors of internal temperature and humidity 40 and 41, internal air quality 42 and external temperature 43, allow the control system to control the thermo-hygrometric and internal air quality parameters.

6.8) Multifunction Apparatuses Applied to Building Structures.

The air conditioning systems equipped with the elements referred to in the present invention can also be directly integrated in various types of building structures, made with prefabricated modules/structures or with frames and infill panels. FIGS. 88 and 89, already explained, can represent a possible application scheme thereof, for example:

building structures that use wool/wood or hemp fibre, mineralised, aerated concrete or cement, porous, draining, and other types, also in the form of formwork blocks or prefabricated structures, possibly already equipped with thermal insulation, cavities and reinforcements to be filled with cement during construction. In such cases, cavities for the transit of the supply air would be arranged in the blocks and in the prefabricated structures. The surface permeable to air facing the interior of the rooms, on the ceiling and/or on the wall, which will form the actual terminal element 4, can be integrated into the prefabricated elements themselves or subsequently made by means of special panels with the supply plenum 3 behind;

dry building structures with load-bearing "skeleton" and panel infill:

in these cases, the cavities for the transit of the supply air would be designed, as well as the surfaces permeable to air (on the ceiling and/or on the wall), with the supply plenum 3 behind, made by means of special panels that will form the actual terminal element 4.

The surface of the multifunction element can then be finished externally in several manners.

The use of the air conditioning system in building structures is also advantageous from the energy point of view, since the supply air of the terminal element 4, before being emitted into the room, i.e., in the rooms of the structure, can affect the entire structure itself, in a more or less significantly calculated manner depending on the positioning of the thermal insulation of the structure with respect to the air flow, to carry out an energy storage in the form of "thermally active building systems" (TABS) and/or change the distribution of loads over time, with a reduction in energy costs and installed power.

This possibility can be exploited, for example, also in buildings equipped with refrigeration units with heat pump and photovoltaic systems, to store the energy produced in the most favourable energy periods in the form of thermal storage (hot or cold depending on the operation), using it in the remaining periods, during which the room temperatures can possibly be attenuated to make greater use of the stored energy.

The heat accumulated by the mass of the structures affected by the supply air of the terminal element 4 also acts as a thermal flywheel on the supply air itself during the defrosting steps of the heat pump.

Another interesting feature of this application is that through the free cooling function, the fresh outside air feeds the terminal element 4, significantly cooling the lapped and crossed structures.

6.9) Embodiments of the Fan Coil Multifunction Apparatus.

The multifunction apparatuses referred to in the present invention, as already explained in the chapter on embodiments of the invention, have been specially designed to be able to operate correctly with relatively low supply static air pressures, such as to allow them to operate correctly using components typically used for the construction of low-head fan coils. The embodiments set forth in this chapter, incorporating within the compartment 44 the components of a fan coil, such as essentially a fan, a heat exchange battery and a condensate collection basin (not depicted in the figure), can be used as a variant of the already known plant systems that use fan coils that introduce high-speed air directly into the room. This possibility will allow to significantly improve the comfort of the rooms, modifying the characteristics of heat exchange with the room and the occupants, affecting the average radiant temperature of the surfaces, eliminating annoying air currents, reducing the residual noise of the fan coils and improving the acoustic qualities of the affected room, thanks to the characteristic, also sound absorbing of the multifunction apparatus.

FIGS. 94 to 101 depict embodiments of possible vertical extension multifunction apparatuses, while FIGS. 102 to 105 relate to horizontal extension embodiments thereof.

Figure 94:
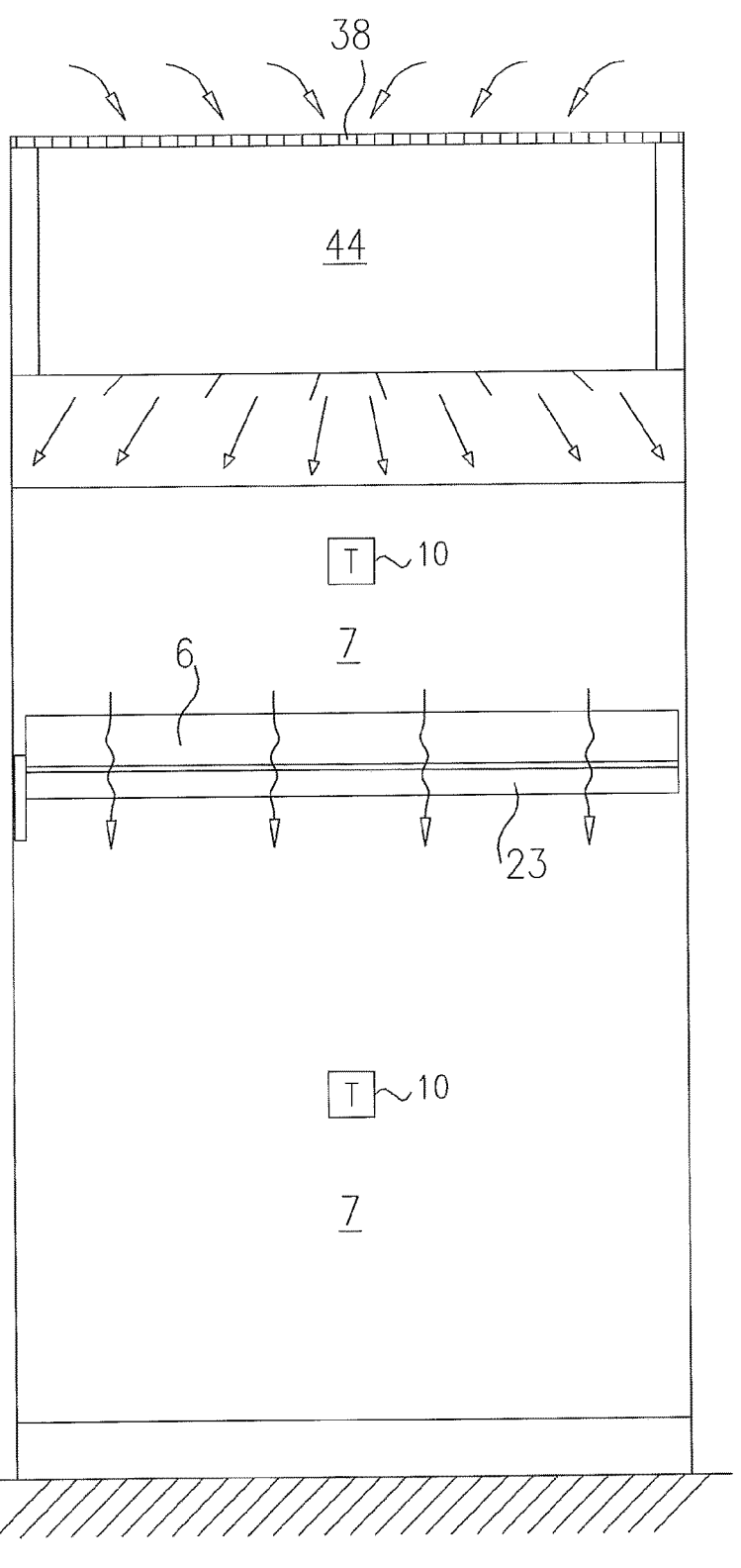
Figure 95:
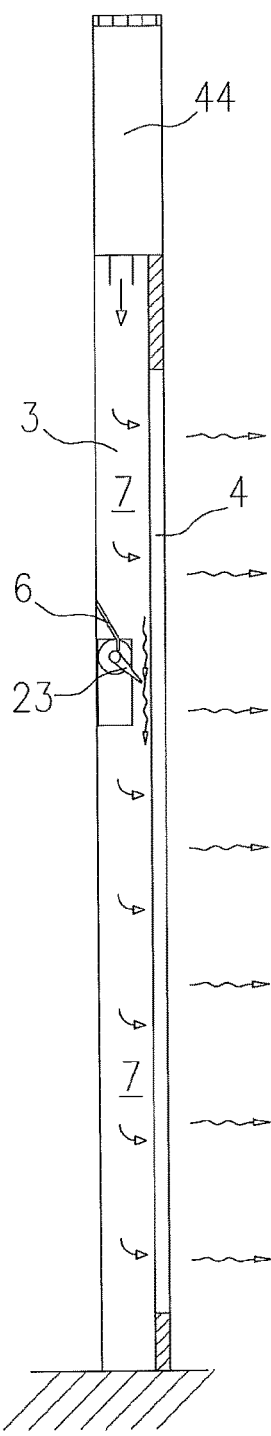

In FIGS. 94-95, the fan coil components are housed in the compartment 44 extending vertically, located at the top of the plenum 3 of the apparatus. The fan coil sucks air from the room through the grille 38 provided with a filter, treats the air and introduces it vertically downwards directly into the plenum 3.

Figure 63:
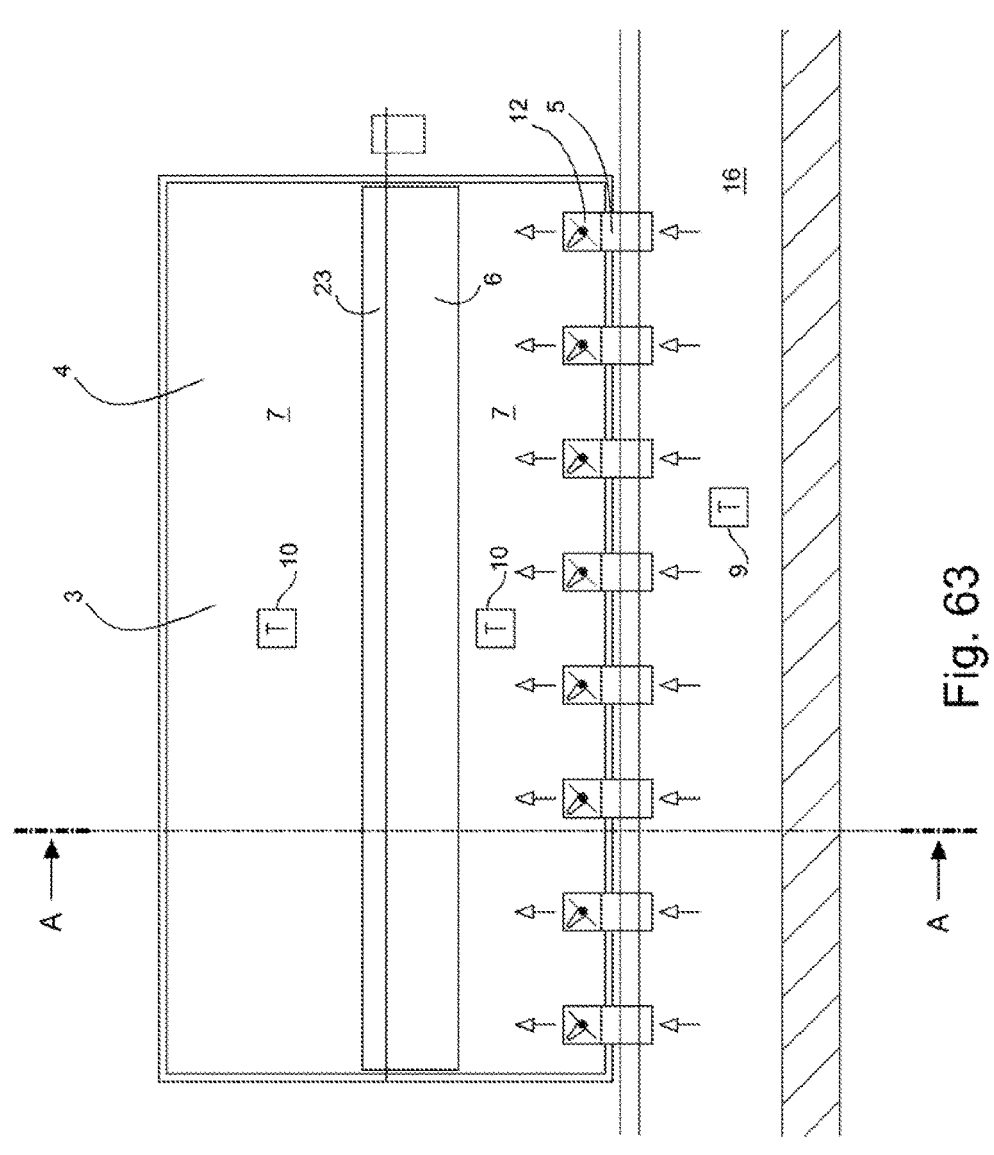

This version of the multifunction apparatus follows the concepts of the version shown in FIG. 63, which was previously explained in the chapter concerning the vertical versions with modulation damper 23 arranged inside the plenum, where it was specified that the relative versions could also be with air supply from above.

The plenum 3 is divided in height into two portions 7 by means of the partitioning wall 6 at which a fin 23 with a variable opening is positioned. The colder the air exiting the fan coil, the more the fin 23 closes to limit the air flow towards the lower portion of the plenum, in order to compensate for the tendency of the air to mainly exit from the lower part of the terminal element 4 and to evenly distribute the air exiting from the entire surface of the terminal element itself. Conversely, the hotter the air is, the more the fin 23 must open to compensate for the tendency of the hot air to mainly exit from the top of the terminal element.

Figures 96, 97:
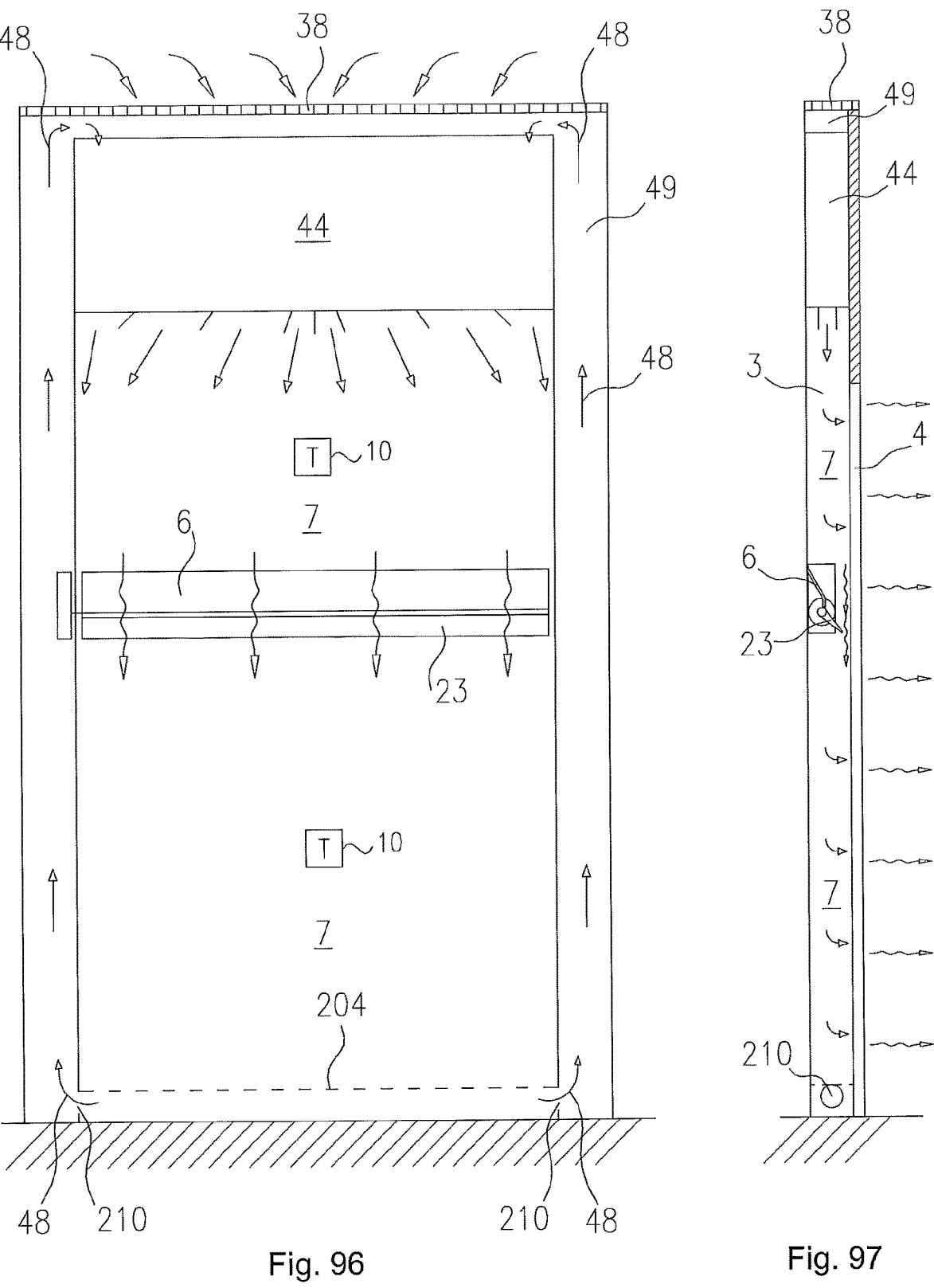

FIGS. 96-97 refer to a variant of the version described above related to FIGS. 94-95, where the function, already mentioned in other versions of possible embodiments, of partial air recirculation 48 in the plenum 3 has been added, which contributes to maintaining a suitable temperature uniformity and an effective radiant effect of the terminal elements 4, reducing the amount of air exiting towards the room, without reducing the amount of supply air introduced by the plenum.

In this case, following the flows indicated by the number 48, a predetermined part of the supply air, after having exchanged heat with the inner surface of the terminal element 4, is sucked back from by the fan coil 44, through the orifices 210 and the lateral ducts 49, without having exited from the terminal element 4 towards the room. In some cases, especially when the apparatus is more than one metre wide, it is advisable to insert the perforated equalisation sheet 204.

The orifices 210 and/or the perforated sheet 204, which are fixed calibrations, can be replaced by an adjustable opening damper (not depicted in the figure), in order to vary the flow rate of recirculated air.

Figures 98, 99:
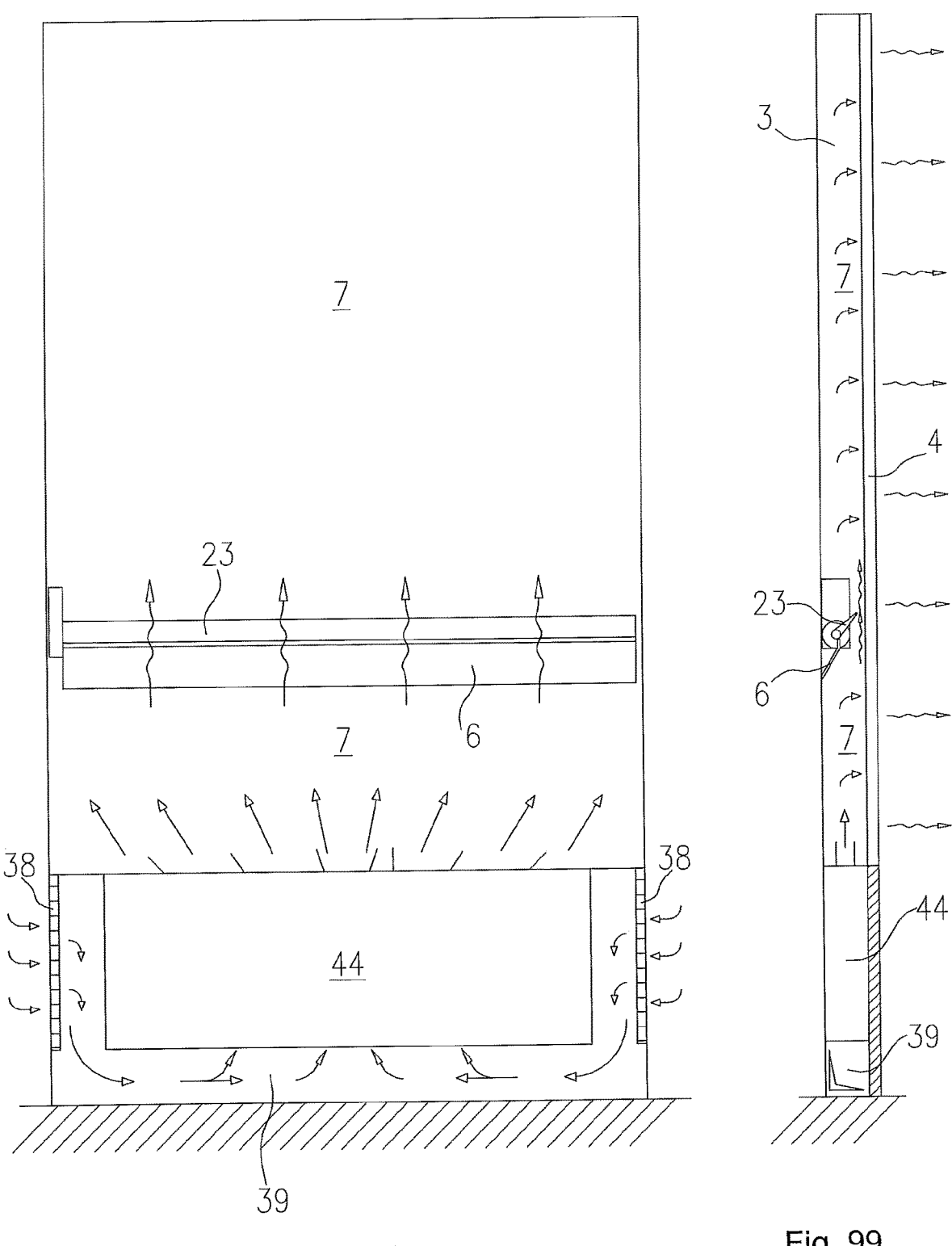

In FIGS. 98-99 the fan coil components are housed in the compartment 44 extending vertically located at the base of the plenum 3 of the apparatus.

This version of the multifunction apparatus also follows the concepts of the version shown in FIG. 63, already explained in the chapter related to the vertical versions with modulation damper 23 arranged inside the plenum. The only substantial difference with respect to the version referred to in FIGS. 94-95 is that the suction of the air taken in from the room occurs from both sides through the grilles 38. The air sucked by the fan coil crosses the grilles 38 provided with filters and enters the fan coil below through the ducts 39, which after having treated it introduces it in the lower part of the plenum 3, portioned into two parts in height by the partitioning wall 6 equipped with the variable opening fin 23.

The colder the air exiting the fan coil, the more the fin 23 must open to facilitate the flow of air to the upper portion of the plenum, in order to compensate for the tendency of the cold air to mainly exit from the lower part of the terminal element 4 and to evenly distribute the air exiting from the entire surface of the terminal element itself.

Conversely, the hotter the air is, the more the fin 23 must close to compensate for the tendency of the hot air to mainly exit from the top of the terminal element.

FIGS. 100-101 refer to a variant of the version described above related to FIGS. 98-99, where the function, already mentioned in other versions of possible embodiments, of partial air recirculation 48 in the plenum 3 has been added, which contributes to maintaining a suitable temperature uniformity and an effective radiant effect of the terminal elements 4, reducing the amount of air exiting towards the room, without reducing the amount of supply air introduced by the plenum.

Also in this case, following the flows indicated by the number 48, a predetermined part of the supply air, after having exchanged heat with the inner surface of the terminal element 4, is sucked back from by the fan coil 44, through the orifices 210 and the lateral ducts 49, without having exited from the terminal element 4 towards the room. In some cases, especially when the apparatus is more than one metre wide, it is advisable to insert the perforated equalisation sheet 204. The orifices 210 and/or the perforated sheet 204, which are fixed calibrations, can be replaced by an adjustable opening damper (not depicted in the figure), in order to vary the flow rate of recirculated air.

Figures 102, 103:
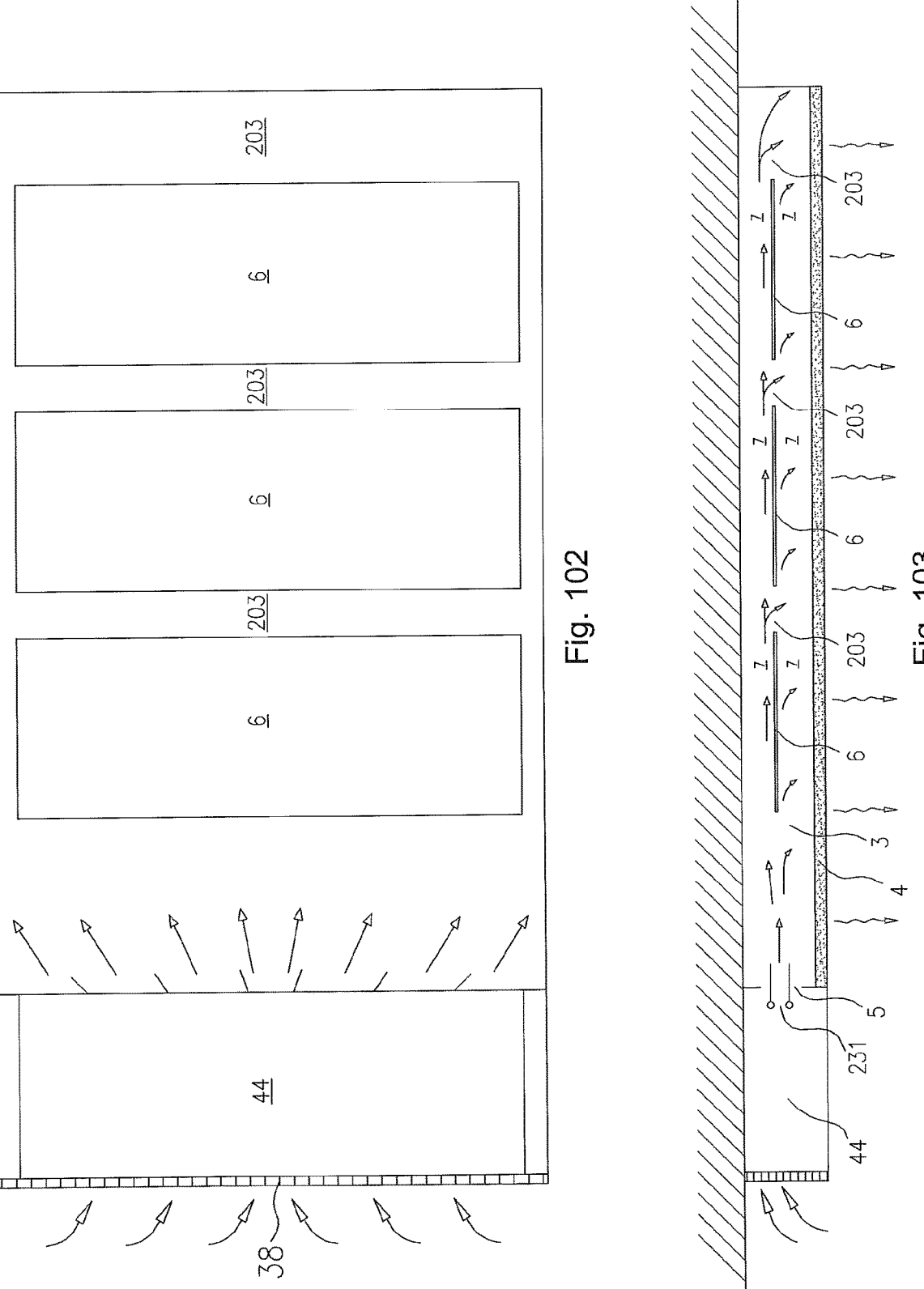

FIGS. 102-103 relate to a horizontally extending embodiment, mounted in adherence to a ceiling, of which FIG. 102 is a section in plan view and FIG. 103 is the cross section.

The system follows the concepts of the horizontal version referred to in FIGS. 80-81 already explained in chapter 6.6), multifunction apparatuses with horizontal extension.

The fan coil components are housed in the compartment 44 extending horizontally.

The air inlet opening is equipped with one or more adjustable deflecting fins 231.

The fan coil sucks the air from the grille 38 equipped with a filter and after having treated it, introduces it directly into the plenum 3. Depending on the length of the plenum, one or more partitioning walls 6 may be necessary to divide the plenum into two portions in height. The partitioning walls are positioned spaced apart so as to have intervals 203 through which air passes from one portion of the plenum to another; depending on the various dimensional shapes of the apparatus, the partitioning walls 6 can also have the surface perforated. The adjustable deflecting fins 231 deflect part of the supply air toward the upper or lower portion 7 of the plenum 3, to vary the height distribution thereof. The cooler the supply air, the more the fin 231 will be rotated to orient the air towards the high partition of the plenum, to compensate for the natural behaviour of the cold air to fall early along the longitudinal progress in the plenum. The air deflected towards the upper wall of the plenum, aided by the ceiling effect and the path channeled above the partitioning walls 6, will retain its progress until the end of the plenum, descending along the path through the open spaces 203, to feed the terminal element 4 together with the part of air not deflected towards the upper part of the plenum, which continues its longitudinal path in the lower portion 7 of the plenum 3 below the partitioning walls 6. Conversely, the warmer the supply air, the more the fin rotates to deflect the air towards the lower portion of the plenum, so as to compensate for the natural behaviour of hot air to adhere to the upper wall of the plenum and exit more at the end of the terminal element; in this case the partitioning walls 6 help the deflected air in the lower part to advance below the partitioning walls, thus near the internal surface of the terminal element. The regulation of the rotation of the fin 231 can also occur by means of automation. In the latter case, the regulation of the deflecting fin will occur according to the fan coil operating mode depending on whether it is cooling or heating, or preferably as a function of the temperature of the air exiting the fan coil and even better according to the temperature difference between the supply air and the room at a height representative of the area occupied by people. In the case of electronic regulation, it will also be possible to move the fin according to specific programs which can also envisage oscillatory movement in swing mode.

Figures 104, 105:
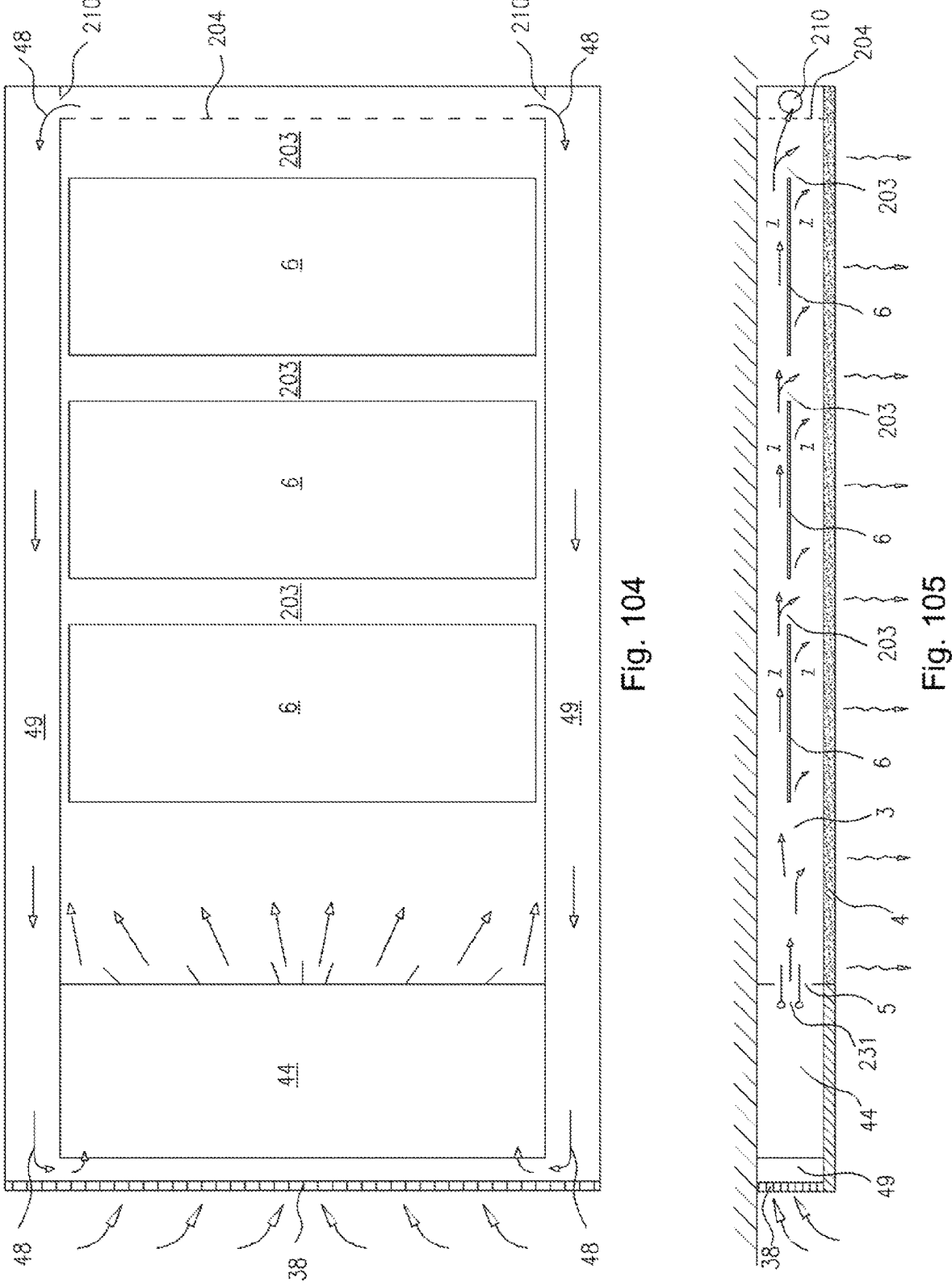

FIGS. 104-105 refer to a variant of the version described above related to FIGS. 102-103, where the function, already mentioned in other versions of possible embodiments, of partial air recirculation 48 in the plenum 3 has been added, which contributes to maintaining a suitable temperature uniformity and an effective radiant effect of the terminal elements 4, reducing the amount of air exiting towards the room, without reducing the amount of supply air introduced by the plenum.

Also in this case, following the flows indicated by the number 48, a predetermined part of the supply air, after having exchanged heat with the internal surface of the terminal element 4, is sucked back by the fan coil 44, through the orifices 210 and the lateral ducts 49, without having exited from the terminal element 4 towards the room. In some cases, especially when the apparatus is more than one metre wide, it is advisable to insert the perforated equalisation sheet 204. The orifices 210 and/or the perforated sheet 204, which are fixed calibrations, can be replaced by an adjustable opening damper (not depicted in the figure), in order to vary the flow rate of recirculated air.

7) General Note

The invention in all the embodiments described is susceptible to numerous modifications and variations, all falling within the inventive concept.

In addition, all the details can be replaced by other technically equivalent elements.

In practice, the materials employed, as well as the shapes and the dimensions, may be any according to requirements without thereby departing from the scope of protection of the following claims.

The invention claimed is:

1. An air conditioning system serving a room to be treated, comprising:
    a source of conditioned air;
    one or more multifunction apparatuses (1), said one or more multifunction apparatuses (1) being each equipped with a plenum (3), one or more air supply ducts (2, 16, 17, 19, 24, 25, 32) to feed said plenum (3) through one or more inlet openings (5, 22, 28*a*, 28*b*, 33), and a terminal element (4) for interfacing said one or more multifunction apparatuses (1) with the room to be treated,
    wherein said terminal element (4) comprises a surface permeable to air, so as to allow a passage of the conditioned air and perform heat exchanges by irradiation and/or convection with the room to be treated,
    wherein said plenums (3) of said multifunction apparatuses (1) extend vertically and are equipped with one or more partitioning walls or diaphragms (6, 53), said one or more partitioning walls or diaphragms (6, 53) dividing said plenums (3) into internal horizontal portions (7) of predetermined height, and
    wherein said multifunction apparatuses (1) comprise regulation systems (8, 12, 15, 15a, 15B, 23, 26, 27, 34,

50, 231) for varying a distribution of the conditioned air between the internal horizontal portions (7) of said apparatuses as a function of temperature and/or flow rate of the conditioned air, and/or a temperature difference between the conditioned air and the room to be treated.

2. The air conditioning system according to claim 1, wherein an upper portion of the one or more multifunction apparatuses (1) has a separate horizontal plenum, placed at a higher height and fed by a branch of the one or more air supply ducts (2, 16, 17, 19, 24, 25, 32) that also feeds the vertical plenums of the one or more multifunction apparatuses, and wherein said regulation systems (8, 12, 15, 15a, 15B, 23, 26, 27, 34, 50, 231) allow varying a distribution of the conditioned air between the portions with horizontal plenum and the vertical plenums of the one or more multifunction apparatuses as a function of the temperature and/or flow rate of the conditioned air and/or the temperature difference between the conditioned air and the room to be treated.

3. The air conditioning system according to claim 1, wherein said terminal element (4) is sound-absorbing and/or wherein a space between the plenum (3) of said multifunction apparatus (1) and the terminal element (4) constitutes a resonance chamber for an acoustic absorption of noise.

4. The air conditioning system according to claim 1, wherein said partitioning walls or diaphragms (6, 53) are constituted by porous or perforated materials or have a structure adapted to allow a controlled passage of the conditioned air between portions (7) of the plenum (3).

5. The air conditioning system according to claim 1, wherein the each of the one or more multifunction apparatuses (1) comprises a compartment (44) inside which components are incorporated usable by low-head fan-coils to introduce the conditioned air directly into the plenum (3).

6. The air conditioning system according to the claim 5, further comprising a partial recirculation device (48) equipped with orifices (210) and lateral ducts (49), which allows a predetermined part of the conditioned air, after exchanging heat with an internal surface of the terminal element (4), to be sucked back inside the compartment (44), through the orifices (210) and the lateral ducts (49), without having to come out of the terminal element (4) into the room to be treated.

7. The air conditioning system according to claim 1, wherein said terminal element (4) comprises panels and/or elements in wool, wood fibers, hemp, and/or vegetable, mineral, or plastic materials, pressed and/or mineralized, or treated with resins, or wherein said terminal element comprises panels or elements in modified porous concrete, or panels with a honeycomb internal structure, or a structure creating internal divisions, an air-permeable plaster, and/or an air permeable coating.

8. The air conditioning system according to claim 1, wherein said one or more multifunction apparatuses (1) comprises devices for sanitizing and/or disinfecting the conditioned air of the room to be treated, said devices for sanitizing and/or disinfecting comprising one of the following:

(a) UVC ray systems obtained with UVC lamps placed inside the plenum (3);

(b) UVC ray systems obtained with UVC lamps arranged inside the plenum (3) and coatings containing Titanium Dioxide (TiO$_2$) of internal surfaces of the one or more multifunction apparatuses (1), said coatings being activated by exposure to UVC rays emitted by said UVC lamps so as to obtain air sanitation processes of a PCO (photocatalytic oxidation) type, i.e., photocatalytic oxidation;

(c) UVC ray systems obtained with UVC lamps arranged inside the plenum (3) and coatings containing Titanium Dioxide (TiO$_2$) of the internal surfaces of the one or more multifunction apparatuses (1), said coatings being activated by exposure to the UVC rays emitted by said UVC lamps so as to obtain air sanitation processes of a PCO (photocatalytic oxidation) type, said sanitation processes comprising photocatalytic oxidation and UVV ray systems obtained with UVV lamps arranged inside the plenum (3) for production of ozone, said UVV ray systems being adapted for a disinfection of surfaces and rooms while not occupied by people; or (d) ionizing devices equipped with polarizing electrodes that generate an electric field which produces and determines an emission of positive or negative ions from air molecules present in a plasma state, the air molecules binding to airborne particles that are present, making the airborne particles aggregate with each other, which, once the aggregated airborne particles have reached a sufficient mass, precipitate or electrostatically adhere to surfaces having opposite or neutral charge.

9. The air conditioning system according to claim 1, wherein the one or more multifunction apparatuses (1), or the terminal element (4), are made of materials with an areal weight of at least 12 kg/m$^2$ for having a mass acting as a thermal flywheel.

10. The air conditioning system according to claim 1, wherein said one or more multifunction apparatuses (1) comprises lighting devices and said terminal element (4) is transparent to light.

11. The air conditioning system according to claim 1, wherein a front surface of the terminal element (4) have a minimum surface area for each m$^3$/h of an air flow that passes through the terminal element to be introduced into the room, the front surface varying according to rooms in which it is located, equal to at least 500 cm$^2$ per m$^3$/h in rooms with a low air flow demand, at least 250 cm$^2$ per m$^3$/h for rooms with an average air flow demand, at least 100 cm$^2$ per m$^3$/h for rooms with medium-high air flow demand, at least 50 cm$^2$ per m$^3$/h for rooms with high air flow demand, at least 40 cm$^2$ per m$^3$/h for rooms with very high air flow demand, so as to obtain an average radiant temperature of the surfaces of the room which is conducive to well-being, and/or to have an effective sound-absorbing surface for an acoustic improvement of the room, while maintaining a desired distribution of the conditioned air within the plenums (3) and related partitions (7), as well as a desired introduction of the conditioned air into the room and a maximum efficiency and effectiveness of the air conditioning system in all system operating conditions.

12. The air conditioning system according to claim 11, wherein the one or more multifunction apparatuses (1) have a static operating pressures which varies depending on a type of rooms in which the one or more multifunction apparatuses are located, less than 15 Pa for rooms with low air flow demand, less than 20 Pa for rooms with medium air flow demand, less than 35 Pa for rooms with medium-high air flow demand, less than 45 Pa for rooms with high air flow demand, and 55 Pa for rooms with very high air flow demand.

13. An air conditioning system serving a room to be treated, comprising:
    a source of conditioned air;

one or more multifunction apparatuses (1) each equipped
with a plenum (3);
one or more air supply ducts (2, 16, 17, 19, 24, 25, 32),
to feed said plenum (3) through one or more inlet
openings (5); and
a terminal element (4) for interfacing said one or more
multifunction apparatuses (1) with the room to be
treated,
wherein said terminal element (4) comprises a perforated
sheet or a surface permeable to air to allow a passage
of the conditioned air and to perform thermal
exchanges by irradiation and/or convection with the
room to be treated,
wherein said plenums (3) of said one or more multifunc-
tion apparatuses (1) extend horizontally and comprise
one or more partitioning walls (6) which divide said
plenums (3) into at least one upper internal portion (7)
and at least one lower internal portion (7) of said
plenums (3),
wherein said partitioning walls (6) are provided with
openings (203) for a controlled passage of the condi-
tioned air between the upper and the lower portions (7)
of the plenums (3).
14. The air conditioning system according to claim 13,
wherein said plenums (3) of said multifunction apparatuses
(1) comprise a movable deflecting fin (231), arranged on a
corresponding air inlet opening (5) to deflect part of the
conditioned air towards the upper or the lower portions (7)
of a corresponding plenum (3) as a function of temperature
and/or flow rate of the conditioned air and/or a temperature
difference between the conditioned air and the room to be
treated.
15. The air conditioning system according to claim 13,
wherein said terminal element (4) is sound-absorbing and/or
wherein a space between the plenum (3) of said multifunc-
tion apparatus (1) and the terminal element (4) constitutes a
resonance chamber for an acoustic absorption of noise.
16. The air conditioning system according to claim 13,
wherein said partitioning walls or diaphragms (6, 53) are
constituted by porous or perforated materials or have a
structure adapted to allow a controlled passage of the
conditioned air between portions (7) of the plenum (3).
17. The air conditioning system according to claim 13,
wherein the each of the one or more multifunction appara-
tuses (1) comprises a compartment (44) inside which com-
ponents are incorporated usable by low-head fan-coils to
introduce the conditioned air directly into the plenum (3).
18. The air conditioning system according to the claim 17,
further comprising a partial recirculation device (48)
equipped with orifices (210) and lateral ducts (49), which
allows a predetermined part of the conditioned air, after
exchanging heat with an internal surface of the terminal
element (4), to be sucked back inside the compartment (44),
through the orifices (210) and the lateral ducts (49), without
having to come out of the terminal element (4) into the room
to be treated.
19. The air conditioning system according to claim 13,
wherein said terminal element (4) comprises panels and/or
elements in wool, wood fibers, hemp, and/or vegetable,
mineral, or plastic materials, pressed and/or mineralized, or
treated with resins, or wherein said terminal element com-
prises panels or elements in modified porous concrete, or
panels with a honeycomb internal structure, or a structure
creating internal divisions, an air-permeable plaster, and/or
an air permeable coating.
20. The air conditioning system according to claim 13,
wherein said one or more multifunction apparatuses (1) comprises devices for sanitizing and/or disinfecting the
conditioned air of the room to be treated, said devices for
sanitizing and/or disinfecting comprising one of the follow-
ing:
(a) UVC ray systems obtained with UVC lamps placed
inside the plenum (3);
(b) UVC ray systems obtained with UVC lamps arranged
inside the plenum (3) and coatings containing Titanium
Dioxide ($TiO_2$) of internal surfaces of the one or more
multifunction apparatuses (1), said coatings being acti-
vated by exposure to UVC rays emitted by said UVC
lamps so as to obtain air sanitation processes of a PCO
(photocatalytic oxidation) type, i.e., photocatalytic oxi-
dation;
(c) UVC ray systems obtained with UVC lamps arranged
inside the plenum (3) and coatings containing Titanium
Dioxide ($TiO_2$) of the internal surfaces of the one or
more multifunction apparatuses (1), said coatings being
activated by exposure to the UVC rays emitted by said
UVC lamps so as to obtain air sanitation processes of
a PCO (photocatalytic oxidation) type, said sanitation
processes comprising photocatalytic oxidation and
UVV ray systems obtained with UVV lamps arranged
inside the plenum (3) for production of ozone, said
UVV ray systems being adapted for a disinfection of
surfaces and rooms while not occupied by people; or
(d) ionizing devices equipped with polarizing elec-
trodes that generate an electric field which produces
and determines an emission of positive or negative ions
from air molecules present in a plasma state, the air
molecules binding to airborne particles that are present,
making the airborne particles aggregate with each
other, which, once the aggregated airborne particles
have reached a sufficient mass, precipitate or electro-
statically adhere to surfaces having opposite or neutral
charge.
21. The air conditioning system according to claim 13,
wherein the one or more multifunction apparatuses (1), or
the terminal element (4), are made of materials with an areal
weight of at least 12 kg/m$^2$ for having a mass acting as a
thermal flywheel.
22. The air conditioning system according to claim 13,
wherein said one or more multifunction apparatuses (1)
comprises lighting devices and said terminal element (4) is
transparent to light.
23. The air conditioning system according to claim 13,
wherein a front surface of the terminal element (4) have a
minimum surface area for each m$^3$/h of the air flow that
passes through the terminal element to be introduced into the
room, the front surface varying according to rooms in which
it is located, equal to at least 500 cm$^2$ per m$^3$/h in rooms with
a low air flow demand, at least 250 cm$^2$ per m$^3$/h for rooms
with an average air flow demand, at least 100 cm$^2$ per m$^3$/h
for rooms with medium-high air flow demand, at least 50
cm$^2$ per m$^3$/h for rooms with high air flow demand, at least
40 cm$^2$ per m$^3$/h for rooms with very high air flow demand,
so as to obtain an average radiant temperature of the surfaces
of the room which is conducive to well-being, and/or to have
an effective sound-absorbing surface for an acoustic
improvement of the room, while maintaining a desired
distribution of the conditioned air within the plenums (3)
and related partitions (7), as well as a desired introduction of
the conditioned air into the room and a maximum efficiency
and effectiveness of the air conditioning system in all system
operating conditions.
24. The air conditioning system according to claim 23,
wherein the one or more multifunction apparatuses (1) have a static operating pressures which varies depending on a type of rooms in which the one or more multifunction apparatuses are located, less than 15 Pa for rooms with low air flow demand, less than 20 Pa for rooms with medium air flow demand, less than 35 Pa for rooms with medium-high air flow demand, less than 45 Pa for rooms with high air flow demand, and 55 Pa for rooms with very high air flow demand.

25. The air conditioning systems according to claim 1, wherein said plenums (3) of said multifunction apparatuses (1) are equipped with said one or more partitioning walls or diaphragms (6, 53), and wherein said partitioning walls or diaphragms (6, 53) comprise openings (203) for a controlled passage of the conditioned air between the internal horizontal portions (7) of said plenums (3).

* * * * *